United States Patent
Harris et al.

(10) Patent No.: US 8,801,732 B2
(45) Date of Patent: Aug. 12, 2014

(54) SURGICAL STAPLER TO SECURE A TISSUE FOLD

(75) Inventors: Jason L. Harris, Mason, OH (US); Lawrence Crainich, Charlestown, NH (US); Michael J. Stokes, Cincinnati, OH (US); Mark S. Zeiner, Mason, OH (US); Daniel E. Alesi, Lebanon, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 503 days.

(21) Appl. No.: 12/359,357

(22) Filed: Jan. 26, 2009

(65) Prior Publication Data

US 2010/0191258 A1      Jul. 29, 2010

(51) Int. Cl.
*A61B 17/08*       (2006.01)

(52) U.S. Cl.
USPC .................. 606/151; 606/219; 227/175.1

(58) Field of Classification Search
USPC .................. 606/75, 151, 219–221; 227/175.1–182.1
See application file for complete search history.

(56) References Cited

U.S. PATENT DOCUMENTS

| | | |
|---|---|---|
| 2,185,518 A | 1/1940 | Posnack |
| 3,638,847 A | 2/1972 | Noiles et al. |
| 3,740,994 A | 6/1973 | DeCarlo, Jr. |
| 3,819,100 A | 6/1974 | Noiles et al. |
| 4,086,926 A | 5/1978 | Green et al. |
| 4,396,139 A | 8/1983 | Hall et al. |
| 4,407,286 A | 10/1983 | Noiles et al. |
| 4,489,875 A | 12/1984 | Crawford et al. |
| 4,505,273 A | 3/1985 | Braun et al. |
| 4,509,518 A | 4/1985 | McGarry et al. |
| 4,624,254 A | 11/1986 | McGarry et al. |
| 4,648,542 A | 3/1987 | Fox et al. |
| 4,669,647 A | 6/1987 | Storace |
| 4,874,122 A | 10/1989 | Froelich et al. |
| 4,899,745 A | 2/1990 | Laboureau et al. |
| 5,032,127 A | 7/1991 | Frazee et al. |
| 5,156,609 A | 10/1992 | Nakao et al. |
| 5,242,457 A | 9/1993 | Akopov et al. |
| 5,333,772 A | 8/1994 | Rothfuss et al. |
| 5,350,400 A | 9/1994 | Esposito et al. |
| 5,392,978 A | 2/1995 | Velez et al. |
| 5,413,584 A | 5/1995 | Schulze |

(Continued)

FOREIGN PATENT DOCUMENTS

| | | |
|---|---|---|
| DE | 2348670 A1 | 4/1974 |
| DE | 29720952 U1 | 1/1998 |

(Continued)

OTHER PUBLICATIONS

Talebpour M, Amoli BS. Laparoscopic Total Gastric Vertical Plication in Morbid Obesity. Journal of Laparoendosc Adv Surg Tech A 2007;17:793-8.

(Continued)

*Primary Examiner* — Melanie Tyson

(57) ABSTRACT

A method of deploying a surgical fastener using the steps of introducing a fastener into a body of a patient while the fastener is in a first shape forming a first loop. Moving end segments of the fastener away from each other substantially along an entire length thereof. And forming the fastener into a second loop having a width greater than a width of the first loop.

11 Claims, 45 Drawing Sheets

(56) References Cited

U.S. PATENT DOCUMENTS

| | | | |
|---|---|---|---|
| 5,439,468 | A | 8/1995 | Schulze et al. |
| 5,544,802 | A | 8/1996 | Crainich |
| 5,626,585 | A | 5/1997 | Mittelstadt et al. |
| 5,645,567 | A * | 7/1997 | Crainich ............... 606/219 |
| 5,715,987 | A | 2/1998 | Kelley et al. |
| 5,725,554 | A | 3/1998 | Simon et al. |
| 5,732,871 | A | 3/1998 | Clark et al. |
| 5,829,662 | A | 11/1998 | Allen et al. |
| 6,228,098 | B1 | 5/2001 | Kayan et al. |
| 6,277,131 | B1 | 8/2001 | Kalikow |
| 6,306,149 | B1 | 10/2001 | Meade |
| 6,330,964 | B1 | 12/2001 | Kayan et al. |
| 6,352,541 | B1 | 3/2002 | Kienzle et al. |
| 6,450,391 | B1 | 9/2002 | Kayan et al. |
| 6,530,933 | B1 | 3/2003 | Yeung et al. |
| 6,695,854 | B1 | 2/2004 | Kayan et al. |
| 6,726,705 | B2 | 4/2004 | Peterson et al. |
| 6,767,356 | B2 | 7/2004 | Kanner et al. |
| 6,837,895 | B2 | 1/2005 | Mayenberger |
| 6,915,937 | B2 | 7/2005 | Lat et al. |
| 6,957,756 | B2 | 10/2005 | Lat et al. |
| 7,056,330 | B2 | 6/2006 | Gayton |
| 7,059,509 | B2 | 6/2006 | Brown |
| 7,112,214 | B2 * | 9/2006 | Peterson et al. ............ 606/220 |
| 7,179,265 | B2 | 2/2007 | Manetakis et al. |
| 7,320,692 | B1 | 1/2008 | Bender et al. |
| 7,344,544 | B2 | 3/2008 | Bender et al. |
| 7,458,978 | B1 | 12/2008 | Bender et al. |
| 7,473,258 | B2 | 1/2009 | Clauson et al. |
| 7,533,790 | B1 | 5/2009 | Knodel et al. |
| 7,556,647 | B2 * | 7/2009 | Drews et al. ................ 623/2.11 |
| 7,741,520 | B2 | 6/2010 | Brueggemeier et al. |
| 7,744,613 | B2 | 6/2010 | Ewers et al. |
| 7,753,250 | B2 | 7/2010 | Clauson et al. |
| 7,753,870 | B2 | 7/2010 | Demarais et al. |
| 7,887,553 | B2 | 2/2011 | Lehman et al. |
| 8,066,720 | B2 | 11/2011 | Knodel et al. |
| 8,142,450 | B2 | 3/2012 | Harris et al. |
| 2006/0020276 | A1 | 1/2006 | Saadat et al. |
| 2007/0185504 | A1 | 8/2007 | Manetakis et al. |
| 2008/0319455 | A1 | 12/2008 | Harris et al. |
| 2009/0112233 | A1 | 4/2009 | Xiao |
| 2009/0206127 | A1 * | 8/2009 | Danielson et al. ......... 227/175.1 |
| 2009/0318936 | A1 | 12/2009 | Harris et al. |
| 2010/0187283 | A1 | 7/2010 | Crainich et al. |
| 2010/0191255 | A1 | 7/2010 | Crainich et al. |

FOREIGN PATENT DOCUMENTS

| | | |
|---|---|---|
| EP | 0068046 B1 | 5/1988 |
| EP | 0864297 B1 | 6/2007 |
| EP | 1908423 B1 | 1/2011 |
| JP | 2004-520154 A | 7/2004 |
| JP | 2005-530567 A | 10/2005 |
| WO | WO 01/76489 A1 | 10/2001 |
| WO | 02/098302 A1 | 12/2002 |
| WO | WO 2008/109876 A1 | 9/2008 |
| WO | WO 2008/112942 A2 | 9/2008 |
| WO | WO 2008/118928 A2 | 10/2008 |
| WO | WO 2009/137517 A1 | 11/2009 |
| WO | WO 2012/103286 A1 | 8/2012 |
| WO | WO 2012/103291 A1 | 8/2012 |

OTHER PUBLICATIONS

Sales Puccini, CE. Surset Gástrico de Sales: Una Alternative Para Cirugía Bariátrica Restrictive. Rev Colomb Cir 2008;23(3):131-5.

Fusco PEB, Poggetti RS, Younes RN, Fontes B, Birolini D. Evaluation of Gastric Greater Curvature Invagination for Weight Loss in Rats. Obes Surg 2006;16:172.

Fusco PEB, Poggetti RS, Younes RN, Fontes B, Birolini D. Comparison of Anterior Gastric Wall and Greater Gastric Curvature Invaginations for Weight Loss in Rats. Obes Surg 2007;17:1340-5.

Brethauer SA, Harris JL, Chand B, Kroh M, Rogula T, Schauer PR. Initial Results of Vertical Gastric Plication for Severe Obesity. Society of American Gastrointestinal and Endoscopic Surgeons. Phoenix, Arizona. Apr. 22-25, 2009.

Ramos AC, Galvao M, Behrens E, Montufar F, Zundel N. Tubular Sleeve Gastroplasty (TSG) as a New Approach to Bariatric Treatment. 14th World Congress of the International Federation for the Surgery of Obesity—Paris, France—Aug. 26-29, 2009.

International Search Report dated Jun. 1, 2010 (PCT/US2010/021929).

International Search Report dated Aug. 13, 2010 (PCT/US2010/021953).

International Search Report dated Apr. 7, 2011 (PCT/US2011/020472).

International Search Report dated Apr. 5, 2011 (PCT/US2011/020476).

International Search Report dated Apr. 10, 2012 (PCT/US2012/022656).

International Search Report dated Apr. 10, 2012 (PCT/US2012/022651).

European Search Report, dated Oct. 1, 2012, Application No. 12172811.7.

European Search Report, dated Oct. 1, 2012, Application No. 12172808.3.

European Search Report, dated Oct. 1, 2012, Application No. 12172816.6.

Co-pending U.S. Appl. No. 12/359,351, filed Jan. 26, 2009, first named inventor Jason L. Harris.

Co-pending U.S. Appl. No. 12/359,354, filed Jan. 26, 2009, first named inventor Jason L. Harris.

Co-pending U.S. Appl. No. 12/608,860, filed Oct. 29, 2009, first named inventor Jason L. Harris.

Co-pending U.S. Appl. No. 12/609,336, filed Oct. 30, 2009, first named inventor Lawrence Crainich.

Co-pending U.S. Appl. No. 12/690,285, filed Jan. 20, 2010, first named inventor Lawrence Crainich.

Co-pending U.S. Appl. No. 13/015,966, filed Jan. 28, 2011, first named inventor Matthew D. Holcomb.

Co-pending U.S. Appl. No. 13/015,977, filed Jan. 28, 2011, first named inventor Matthew D. Holcomb.

Co-pending U.S. Appl. No. 13/164,949, filed Jun. 21, 2011, first named inventor Matthew D. Holcomb.

Co-pending U.S. Appl. No. 13/164,954, filed Jun. 21, 2011, first named inventor Matthew D. Holcomb.

Co-pending U.S. Appl. No. 13/164,960, filed Jun. 21, 2011, first named inventor Matthew D. Holcomb.

Co-pending U.S. Appl. No. 13/164,963, filed Jun. 21, 2011, first named inventor Jason L. Harris.

Co-pending U.S. Appl. No. 13/362,172, filed Jan. 31, 2012, first named inventor Jason L. Harris.

Co-pending U.S. Appl. No. 13/371,678, filed Feb. 13, 2012, first named inventor Matthew D. Holcomb.

Co-pending U.S. Appl. No. 13/371,684, filed Feb. 13, 2012, first named inventor Matthew D. Holcomb.

* cited by examiner

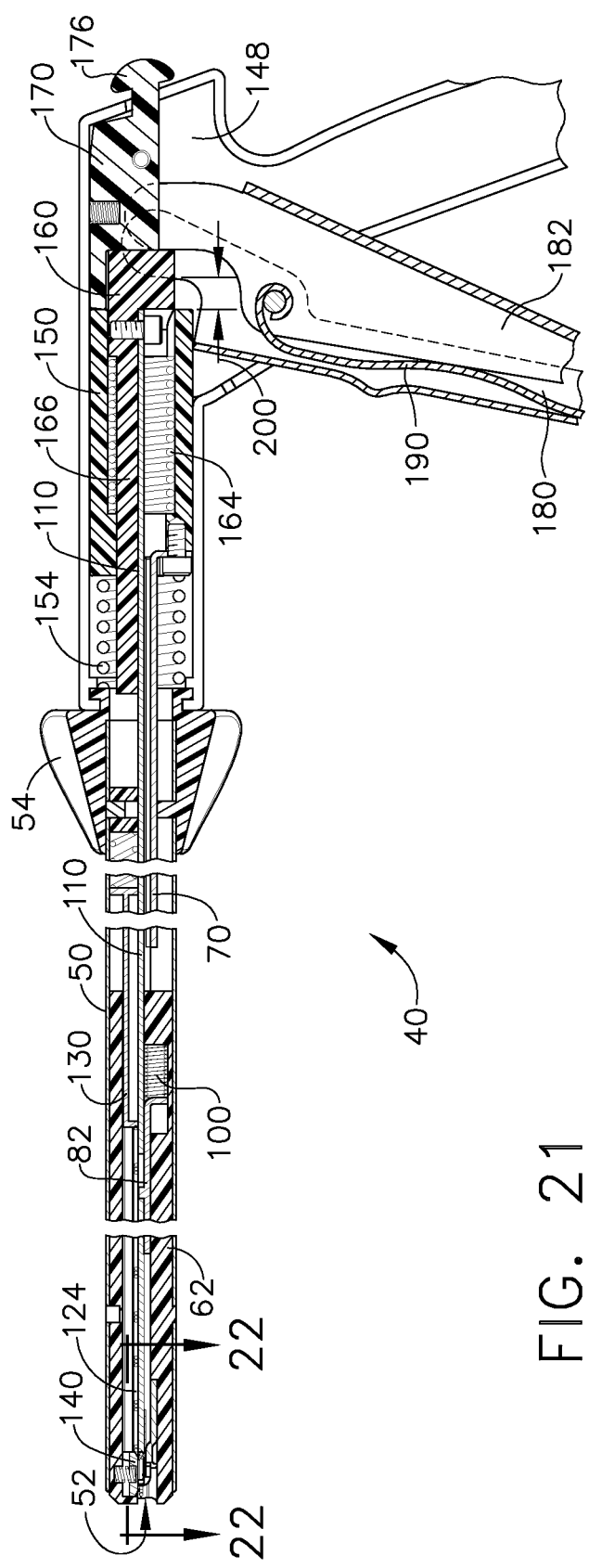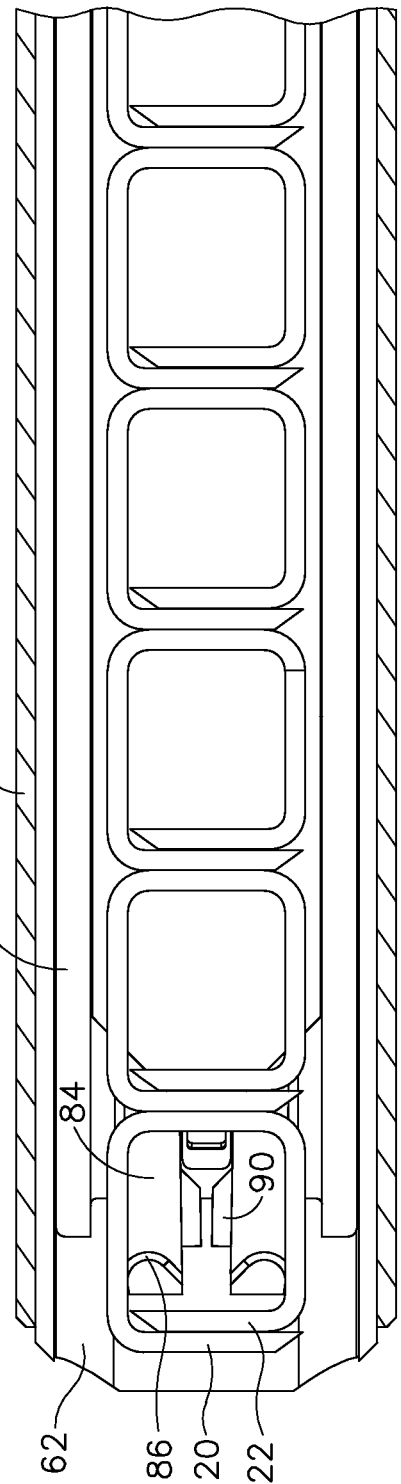
FIG. 21
FIG. 22

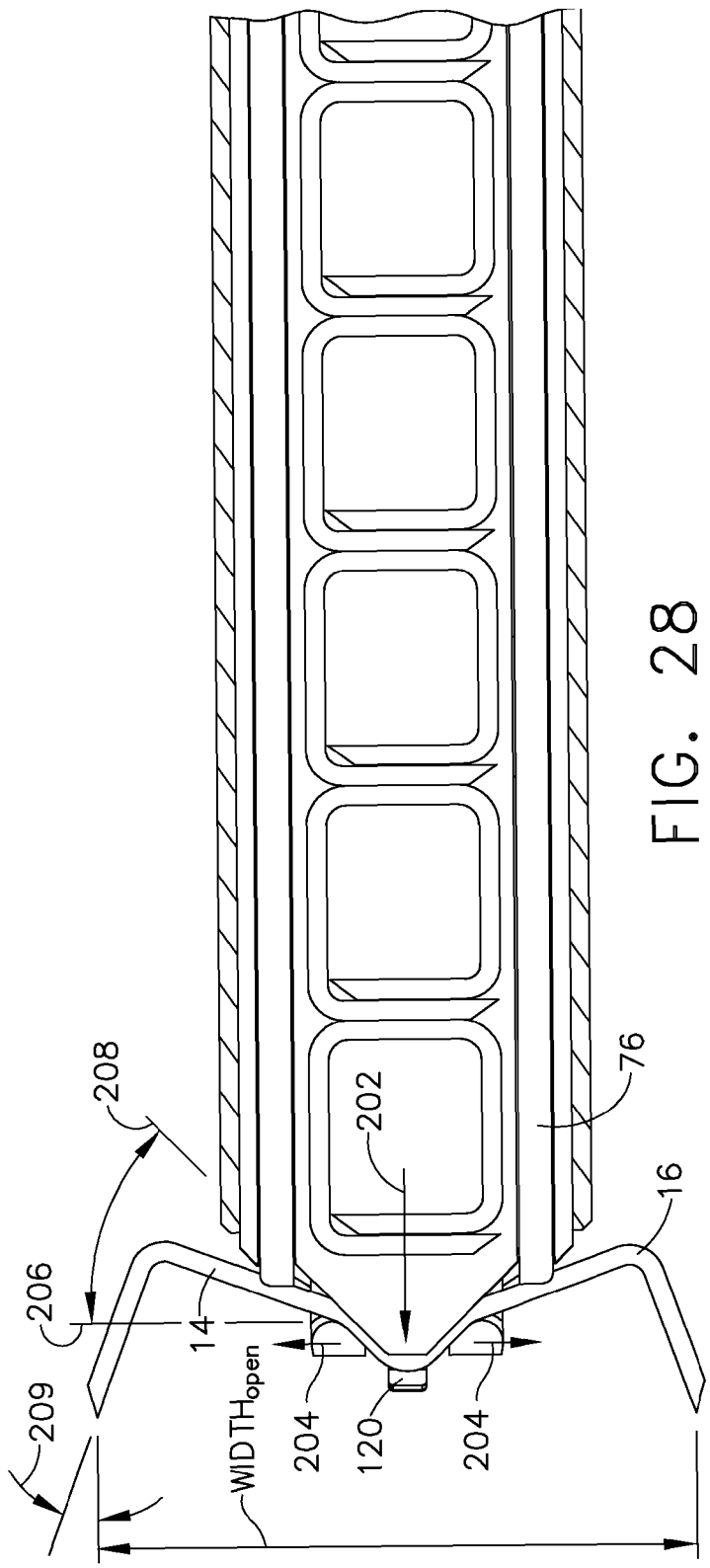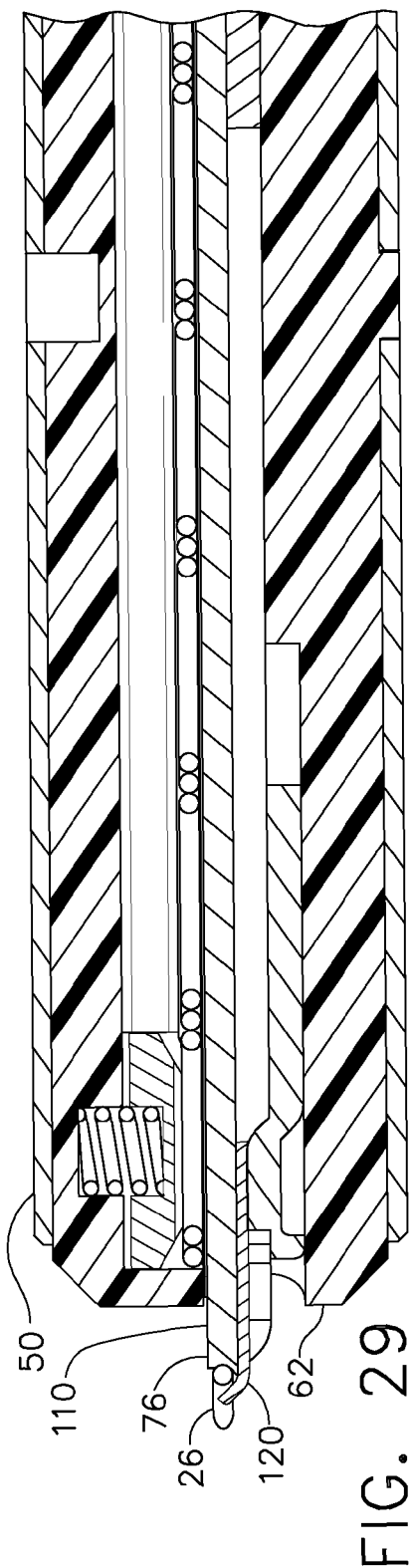

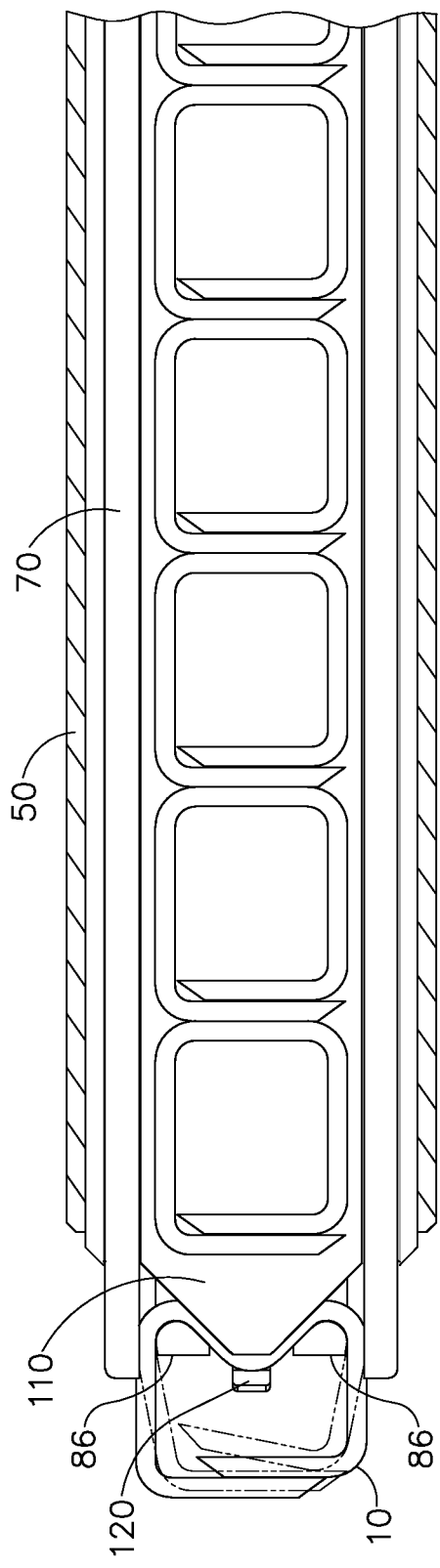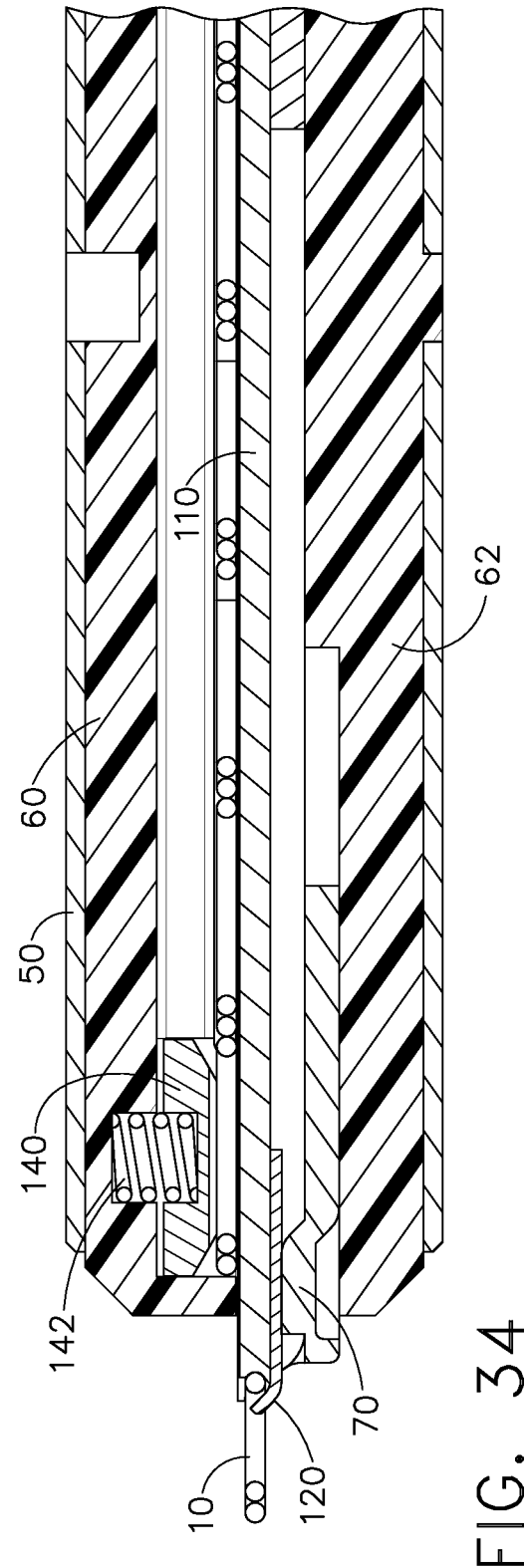
FIG. 33
FIG. 34

US 8,801,732 B2

SURGICAL STAPLER TO SECURE A TISSUE FOLD

FIELD OF THE INVENTION

The present invention relates in general to the joining of cavity wall tissue with a surgical stapler and, more particularly, to a low profile stapler for delivering multiple large-sized box staples to a body cavity through a small delivery port. The low profile stapler enables large areas of tissue to be joined together inside a body cavity through a small access port. The present invention also pertains to methods of using the low profile stapler to approximate tissue within a body cavity during a minimally invasive surgical procedure, such as a gastric volume reduction procedure. The present invention also pertains to the closure of defects on or within the body through secure tissue apposition. The present invention also pertains to the reinforcement of fastened tissues through imbrication of the fastened region secured with the low profile stapler. The present invention also pertains to the attachment of prosthetics to tissue, such as mesh for the repair of a hernia.

BACKGROUND OF THE INVENTION

Obesity is a medical condition affecting more than 30% of the population in the United States. Obesity affects an individual's quality of life and contributes significantly to morbidity and mortality. Obesity is most commonly defined by body mass index (BMI), a measure which takes into account a person's weight and height to gauge total body fat. It is a simple, rapid, and inexpensive measure that correlates both with morbidity and mortality. Overweight is defined as a BMI of 25 to 29.9 kg/m2 and obesity as a BMI of 30 kg/m2. Morbid obesity is defined as BMI ≥40 kg/m2 or being 100 lbs. overweight. Obesity and its co-morbidities are estimated to cost an excess of $100 billion dollars annually in direct and indirect health care costs. Among the co-morbid conditions which have been associated with obesity are type 2 diabetes mellitus, cardiovascular disease, hypertension, dyslipidemias, gastroesophageal reflux disease, obstructive sleep apnea, urinary incontinence, infertility, osteoarthritis of the weight-bearing joints, and some cancers. These complications can affect all systems of the body, and dispel the misconception that obesity is merely a cosmetic problem. Studies have shown that conservative treatment with diet and exercise alone may be ineffective for reducing excess body weight in many patients.

A surgical procedure has been developed for involuting the gastric cavity wall to reduce stomach volume as a treatment for obesity. In the gastric volume reduction (GVR) procedure (e.g., reduction gastroplasty), multiple pairs of suture anchoring devices, such as T-Tag anchors, are deployed through the gastric cavity wall. Preferably, the suture anchors are deployed through a small diameter port in a minimally invasive surgical procedure to reduce trauma to the patient. Following deployment of the T-Tag anchors, the suture attached to each individual pair of anchors is cinched to approximate the tissue and secured to involute the cavity wall between the anchors. This procedure is described in greater detail in co-pending U.S. patent application Ser. Nos. 11/779,314 and 11/779,322, which are hereby incorporated herein by reference in their entirety. Procedure variations of particular interest include the case where the involution occurs about the midline of the anterior surface of the stomach, the case where the involution occurs about the greater curvature of the stomach following the removal or relaxing of attachment points along the greater curve (e.g., dissection of the omentum from the gastric wall), and combinations of these (e.g., the involution begins at the apex of the fundus about the greater curve and transitions to the anterior surface near the incisura angularis). One effect of the procedure is to more rapidly induce feelings of satiation defined herein as achieving a level of fullness during a meal that helps regulate the amount of food consumed. Another effect of this procedure is to prolong the effect of satiety which is defined herein as delaying the onset of hunger after a meal which in turn regulates the frequency of eating. By way of a non-limiting list of examples, positive impacts on satiation and satiety may be achieved by a GVR procedure through one or more of the following mechanisms: reduction of stomach capacity, rapid engagement of stretch receptors, alterations in gastric motility, pressure induced alteration in gut hormone levels, and alterations to the flow of food either into or out of the stomach. As an example, a stomach with a reduced capacity will distend more quickly for a given volume of food. This distension of the stomach may trigger stretch receptors which in turn trigger a sense of satiation. In another example, the procedure will limit the stomach's ability to expand, effectively reducing its capacity or fill volume. Additionally, the procedure may induce a beneficial hormonal effect due either to the more rapid triggering of stretch receptors in certain regions of the stomach or the prevention of hormone release by eliminating triggering mechanisms from being engaged in the infolded region that no longer experiences stretch in the same manner. In yet another example, the procedure may alter gastric emptying by preventing efficient antral contractions. Additionally, the infolded region may provide a restrictive inlet into the stomach just distal to the esophagogastric junction. The GVR procedures described in these applications require individual placement of each suture anchor pair into the cavity wall tissue, and subsequent tensioning of the suture between the anchor pairs in order to involute the tissue. This individual placement of the T-Tag anchors and manual suture tensioning is time intensive; increasing the duration, complexity and cost of the GVR procedure. Accordingly, it is desirable to have a simpler, less expensive means for forming a tissue fold within the peritoneal cavity.

It is known to use surgical staples for binding and holding body tissues together following an anastomosis, skin closure, or other surgical procedure. Traditionally, these staples have had a wide U-shape in the undeformed state, requiring a large incision site or wide diameter trocar cannula to accommodate the staples and stapler. Staples and staplers having a lower profile have been developed for use in smaller diameter (i.e. 5 mm or 10 mm) trocars. However, these devices suffer from a number of deficiencies which make them impractical for use in the GVR procedure. In particular, one such stapler requires bending the staple a full 180° from the predeployment, stacked condition in the stapler to the closed, deployed condition in the tissue. Obtaining this degree of plastic deformation requires that the staple be composed of a soft, ductile material, such as soft titanium. However, the use of a soft ductile material decreases the strength and holding power of the formed staple, thus making the staple unsuitable for the pressures associated with involuting the gastric cavity wall. Staples having a triangular prefiring configuration have also been developed for deployment through a low profile stapler. However, the triangular shape of these staples prevents the staples from being stacked and fed longitudinally through the stapler shaft. Instead, the staples are stacked and fed vertically within the stapler, which reduces the number of staples that can be deployed from the stapler while still maintaining a low profile diameter. Since some versions of the GVR procedure may require a large number of staples to involute the cavity wall, vertical stacking would necessitate using more than one stapler to complete a procedure. Additionally, previous staplers have bent staples at three or fewer points during formation and deployment, which reduces the amount of work hardening and, thus, strengthening within the formed staple.

Accordingly, to facilitate the GVR procedure it is desirable to have an improved surgical staple and deploying stapler for fastening layers of tissue within the peritoneal cavity. It is desirable that the stapler has a low profile for use through a small diameter laparoscopic port or endoscope, yet be capable of deploying staples with a large tissue purchase. Further, it is desirable that the staples have a folded, box shape, and that a large quantity of the staples be deliverable by a single stapler during a procedure. Additionally, it is desirable to have a stapler which alters the configuration of a staple from a low profile, reduced width prior to deployment to a wider, operable width following deployment. Furthermore, it is desirable that the staple be comprised of a strong material having a high yield stress, and that the forming process includes greater than 3 bending points to increase the strength of the formed staple. The present invention provides a surgical staple and stapler which achieves these objectives.

BRIEF DESCRIPTION OF THE DRAWINGS

FIG. 21 is a side sectional view of the stapler of FIG. 7, showing the stapler components in the initial, predeployment condition;

FIG. 22 is a distal end sectional view taken along line 22-22 of FIG. 21;

FIG. 28 is a distal end sectional view taken along line 28-28 of FIG. 27;

FIG. 29 is a side sectional view of the distal end of the stapler, showing an expanded staple held outside the open stapler end by the anvils, spreader and former during the deployment sequence;

FIG. 33 is a distal end sectional view taken along line 33-33 of FIG. 31;

FIG. 34 is a side sectional view of the distal end of the stapler, showing a closed, formed staple held outside the distal stapler end;

DETAILED DESCRIPTION OF THE INVENTION

Figure 1:
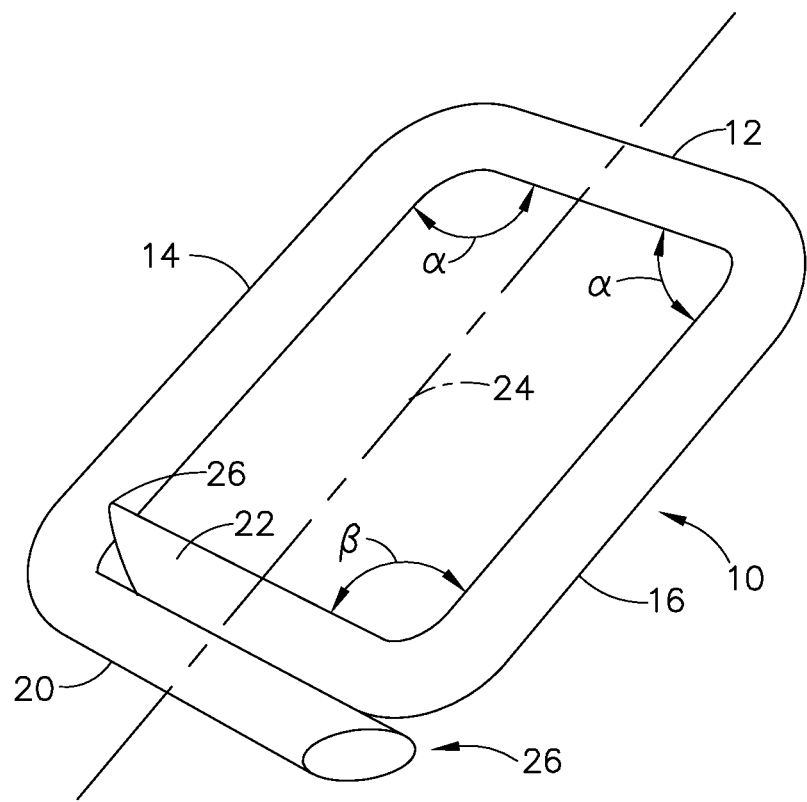
FIG. 1 is an isometric view of a first embodiment of a staple of the present invention shown in an initial, undeployed condition.

Referring now to the drawing figures, in which like numerals indicate like elements throughout the views, FIG. 1 illustrates a first exemplary fastener or staple 10 of the present invention in an initial, undeployed configuration. As shown in FIG. 1, staple 10 comprises a length of wire having a cylindrical cross-section. The cross-sectional shape of the wire may have other shapes (e.g., rectangular, elliptical, etc.) to provide optimal strength for the application and may or may not be uniform along the length of the wire. Staple 10 is formed into a base segment 12 and first and second leg portions 14, 16 that intersect with opposite ends of the base segment. Leg portions 14, 16 intersect with base segment 12 at an angle α of approximately 90°, and extend in a substantially parallel fashion forward of the base segment. In an embodiment wherein the device contains multiple staples, substantially parallel leg portions are able to slide through a channel of uniform rectangular cross section while strictly maintaining their orientation allowing for repeatable firing of the device without jamming. Leg portions 14, 16 need not be straight for leg portions to be substantially parallel. The distance between staples legs 14, 16 describes an initial width dimension for the staple 10. Opposite base segment 12, leg portions 14, 16 bend inward towards a centerline 24 of the staple, at an angle β of approximately 90°, to form staple end segments 20, 22. When the angle β is approximately 90° between leg portions 14, 16, and end segments 20, 22, the end segments are substantially parallel. In an initial configuration (for feeding), the staple may have a closed-form, loop shape, with each side of the loop having at least one portion of the length of wire forming the shape. In a loop shape, two lengths of wire may be disposed across one side of the shape to enclose the shape, as demonstrated by the end segments 20, 22 of FIGS. 1-4B. The tips of end segments 20, 22 are angled to form sharp prongs 26 for piercing tissue. Prongs 26 may be formed on end segments 20, 22 in any desired manner and may have features incorporated to aid in penetration or to aid in hooking (e.g., barbed, etc.) tissue that has been penetrated. However, it is preferable that prongs 26 be formed by a sloping surface tapering inward from an outer edge of the end segment towards an inner edge thereof.

Figure 4A:
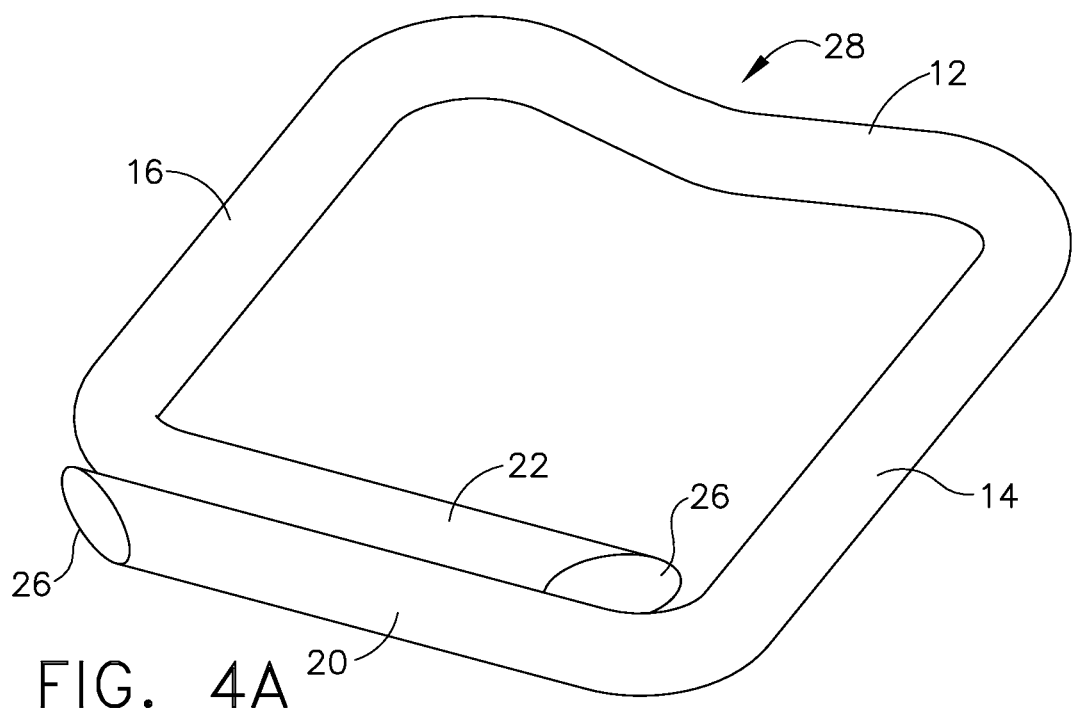
FIG. 4A is an isometric view of a third embodiment of a staple of the present invention shown in an initial, undeployed condition.
Figure 4B:
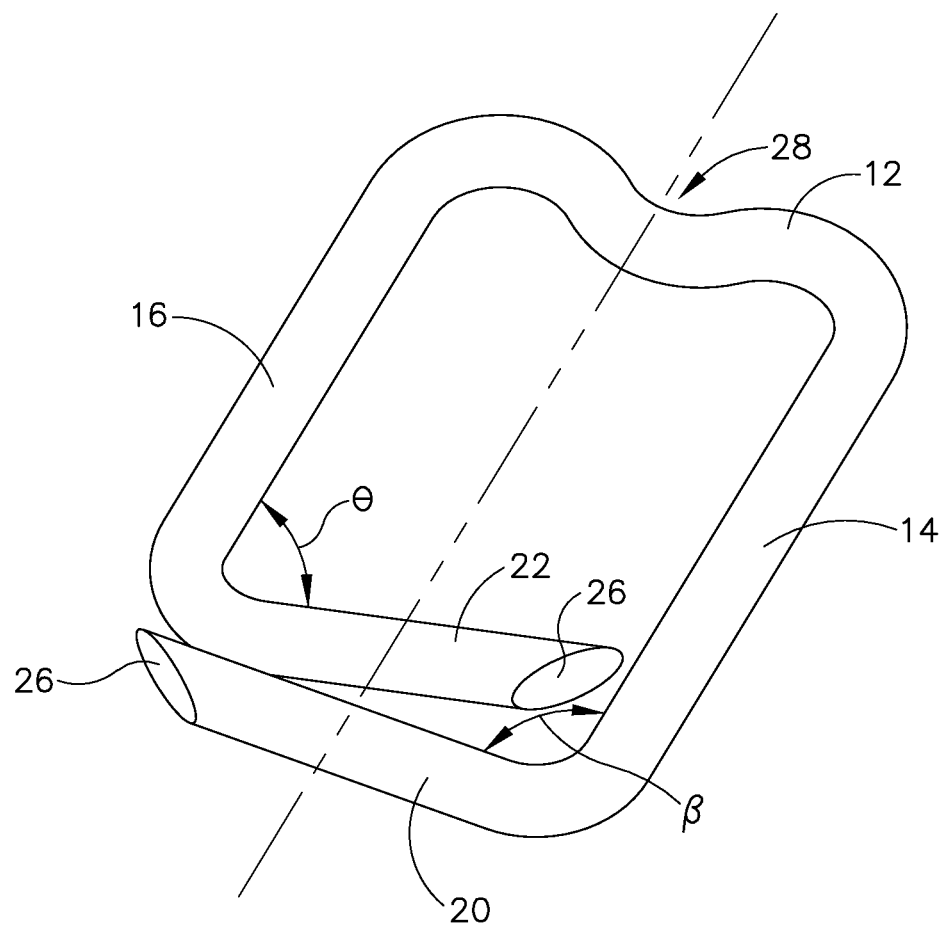
FIG. 4B is an isometric view of a fourth embodiment of a staple of the present invention shown in an initial, undeployed condition.

Staple legs portions 14, 16 are bent at end segments 20, 22 to make one of the leg portions at least one wire diameter longer in length than the other leg portion. The longer length of one leg portion (i.e. staple leg 14 in FIG. 1) enables the end segments 20, 22 to lie in an abutting, parallel position coplanar with base segment 12. Lengthening one staple leg portion relative to the other staple leg portion minimizes the vertical profile of the staple in the undeployed condition, thus allowing the staples to be fed through a smaller area within a stapler. In the undeployed condition, end segments 20, 22 are bent to a length that is less than or equal to the length of base segment 12. In FIG. 1 and FIG. 4A, end segments 20, 22 are of different lengths resulting in a staple that is asymmetrical in shape. At this length, prong tips 26 point in opposite directions and lie within the profile of staple legs 14, 16 to provide a closed-form, substantially rectangular shape for staple 10. In FIG. 4B the length of the end segments 20, 22 are made equal by changing the angle θ defined by leg portion 16 and end segment 22 to less than 90° while keeping end segment 22 substantially straight. In an alternative embodiment (not shown), this is accomplished by providing a curve or bend to end segment 22. Both of these configurations still maintain the closed-form shape and are asymmetric. A staple of this shape could have benefits for engaging tissue which will be described below in further detail. Further, the angulation of end segment 22 may help prevent rotation of the staple once implanted in tissue. In yet another alternative embodiment, staple leg portions 14, 16 may also be slightly curved or bowed in the outward direction so that in its final formed position the tissue tension generally will keep the base segment 12 of the staple parallel to the fastened tissue. In some applications, this may be advantageous to help secure the staple and keep the leg from rotating out of the fastened tissue.

Figure 2:
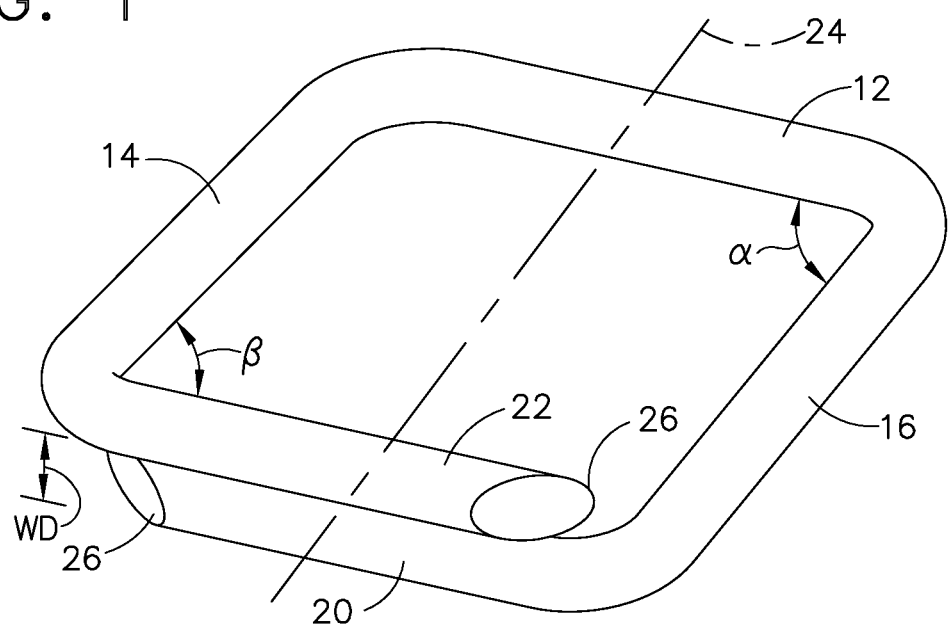
FIG. 2 is an isometric view of a second embodiment of a staple of the present invention shown in an initial, undeployed condition.
Figure 3:
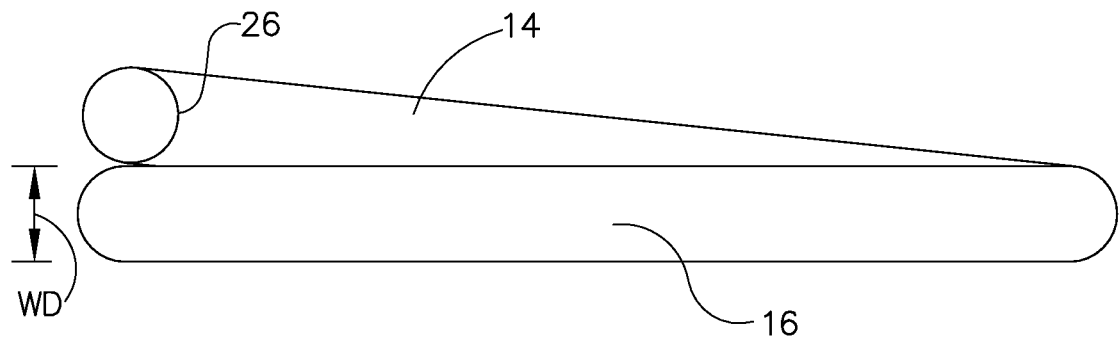
FIG. 3 is side view of the staple shown in FIG. 2.

FIGS. 2 and 3 show an alternative embodiment for staple 10 in which staple leg portions 14, 16 extend forward of base segment 12 a substantially equal length. End segments 20, 22 again bend inwardly at an angle β from staple legs 14, 16, so that prongs 26 point in opposite directions. In this embodiment, the equal length of staple legs 14, 16 enables parallel end segments 20, 22 to overlie one another in a direction normal to the direction of the staple legs. One of the staple legs (leg 14 in FIG. 2) inclines upwardly the distance of one wire diameter (WD) between base segment 12 and the end segment (end 22 in FIG. 2), to enable the end segment to overlie the opposite end segment. This embodiment enables staple legs 14, 16 to have a substantially equal length. Additionally, overlapping end segments 20, 22 provides a larger area of contact between the staples and an end stop when the staples are stacked inside the stapler aiding the reliable feeding of staples.

FIG. 4A shows a third embodiment for staple 10 in which leg portions 14, 16 and end segments 20, 22 have the same initial, unformed condition as the staple shown in FIG. 1. In the third embodiment, however, base segment 12 is modified to include a shallow "V"-shaped depression, identified by reference number 28, at a midpoint of the segment. Depression 28 assists in aligning the staple with the staple spreader during the deployment sequence. One skilled in the art will recognize that other features may be added to aid in feeding and alignment without departing from the spirit of this invention. Exemplary non-limiting examples of closed-form staples with substantially parallel leg portions and end segments are shown in FIGS. 1-4B.

Staples used in this application are preferably biocompatible, implantable, and may optionally be absorbable. A non-limiting list of candidate materials includes: metals such as titanium and its numerous alloys, stainless steel, nitinol, magnesium, and iron; plastics such as PEEK, Prolene™; absorbable materials such as PDS™, Vicryl™, and polylactic acid (PLA); and combinations of these classes of materials. Further, these fasteners may contain therapeutic agents that are selectively or immediately released over time to aid in healing, prevent infection (e.g., triclosan), reduce swelling or edema, etc.

Figure 5:
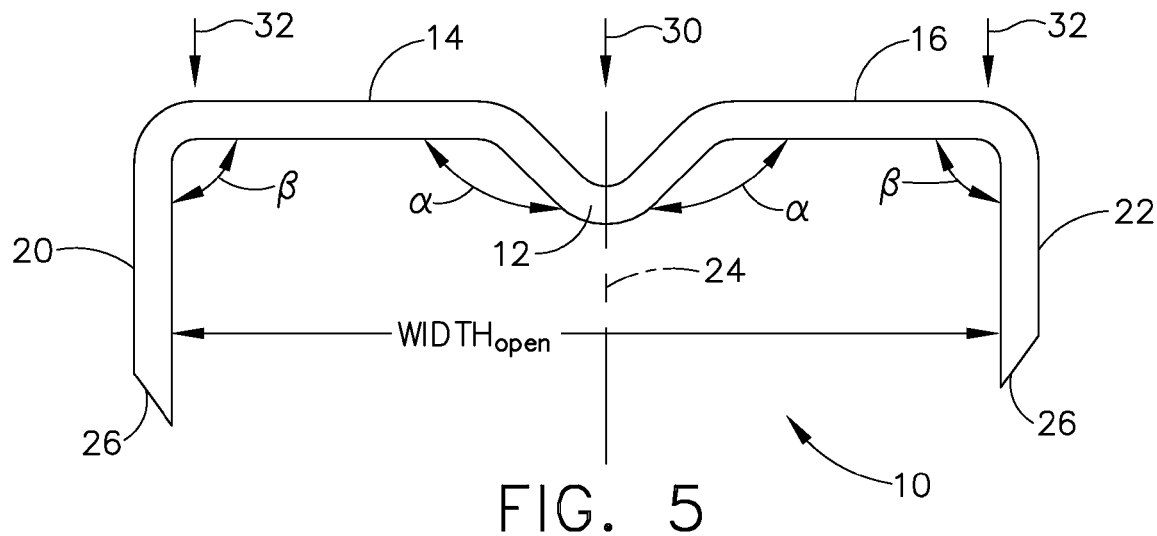
FIG. 5 is an top view of the staple of FIG. 1 shown in an intermediate deployment condition.

FIG. 5 shows staple 10 in a second, intermediate deploying condition. In this intermediate state, staple legs portions 14, 16 are bent outward from centerline 24 to describe a maximum width dimension ($WIDTH_{open}$) between the distal tips of the staple legs. In FIG. 5, staple legs 14, 16 are shown expanded open 180° into lateral alignment with the initial base segment position, with end segments 20, 22 projecting distally in parallel. In this second position, end segments 20, 22 are spaced apart along substantially the entire length of the segments. However, it should be understood that staple legs 14, 16 can be expanded open to an angle less than or greater than 180°, with a maximum bending position occurring when staple legs 14, 16 extend proximal of base segment 12 in alignment with the angled spreader tip, as will be described in more detail below. Staple legs 14, 16 are bent outward by applying an initial deploying force (indicated by arrow 30 in FIG. 5) to a midsection of base segment 12, while the inside of the base segment is held fixed at the intersections between the base segment and the staple legs. The application of force 30 against the opposite fixed forces at the leg intersections, pulls staple legs 14, 16 outward, increasing angle α, while substantially simultaneously indenting the center region of base segment 12. The outward bending of staple legs 14, 16 creates an enlarged opening into the staple 10 that is preferably in the range of twice the width of the stapler housing. Note that staples starting in an asymmetric configuration (e.g., staples depicted in FIG. 1, FIG. 4A, and FIG. 4B) will be transformed into a similarly asymmetric shape depicted in FIG. 5.

Figure 6:
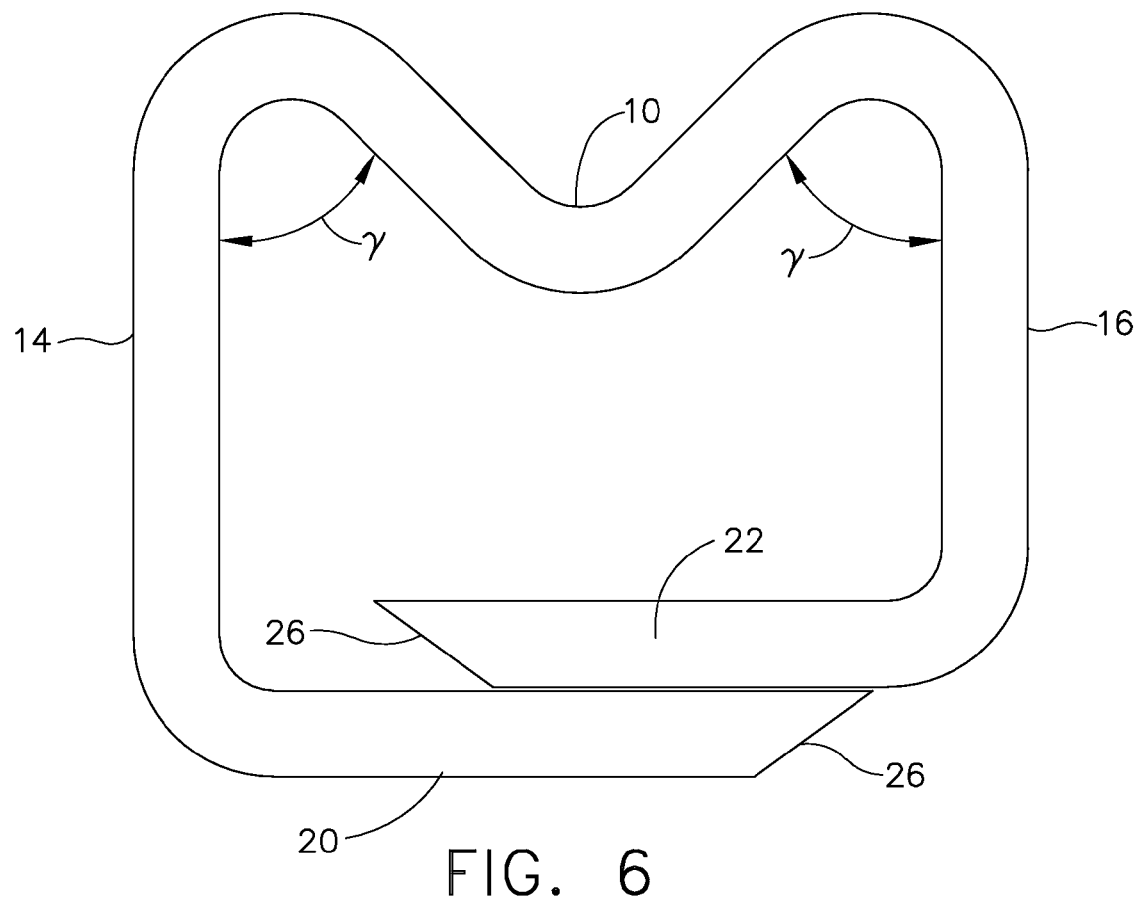
FIG. 6 is an top view of the staple of FIG. 1, showing the staple in a final, deployed condition.

Staple 10 is transformed to a third, fully deployed condition, shown in FIG. 6, by the application of force to laterally spaced points along staple leg portions 14, 16. This force application is indicated by arrows 32 in FIG. 5. It will be appreciated that the force application points in transitioning from the intermediate to fully deployed conditions differ from the force application points in transitioning from the initial to intermediate deployment conditions. The separate force application or bending points in the deployment sequence increase length of wire subject to work hardening increasing the strength of the staple. In the final deployment condition, staple leg portions 14, 16 are drawn back into a substantially parallel position, with prongs 26 again pointing inward through the intervening tissue (not shown) to penetrate and hold the tissue. The length of staple 10 decreases between the initial and final deployment conditions, with an ensuing increase in the staple width, so that the final width dimension of the formed staple (described by the distance between staple legs 14, 16) is greater than the initial width dimension. During deployment, staple 10 transitions between the initial, intermediate and final conditions in a series of steps which may be substantially simultaneous, but which are preferably carried out sequentially so as to first open staple 10 to the intermediate condition of FIG. 5, and then bend each of the staple legs 14, 16 back around into the final condition shown in FIG. 6. In the final, deployed condition, staple legs 14, 16 bend forward of base segment 12 at an internal angle γ of less than 90°, due to base segment 12 projecting into the interior of the closed staple. The inward projection of base segment 12 results from the transitioning of staple legs 14, 16, and has little effect on the volume of tissue which can be held within staple 10, but can help compress materials together within the final substantially closed-form shape of the staple which can improve apposition. Note that staples starting in an asymmetric configuration (e.g., staples depicted in FIG. 1, FIG. 4A, and FIG. 4B) will be transformed into a similarly asymmetric shape depicted in FIG. 6.

Figure 7:
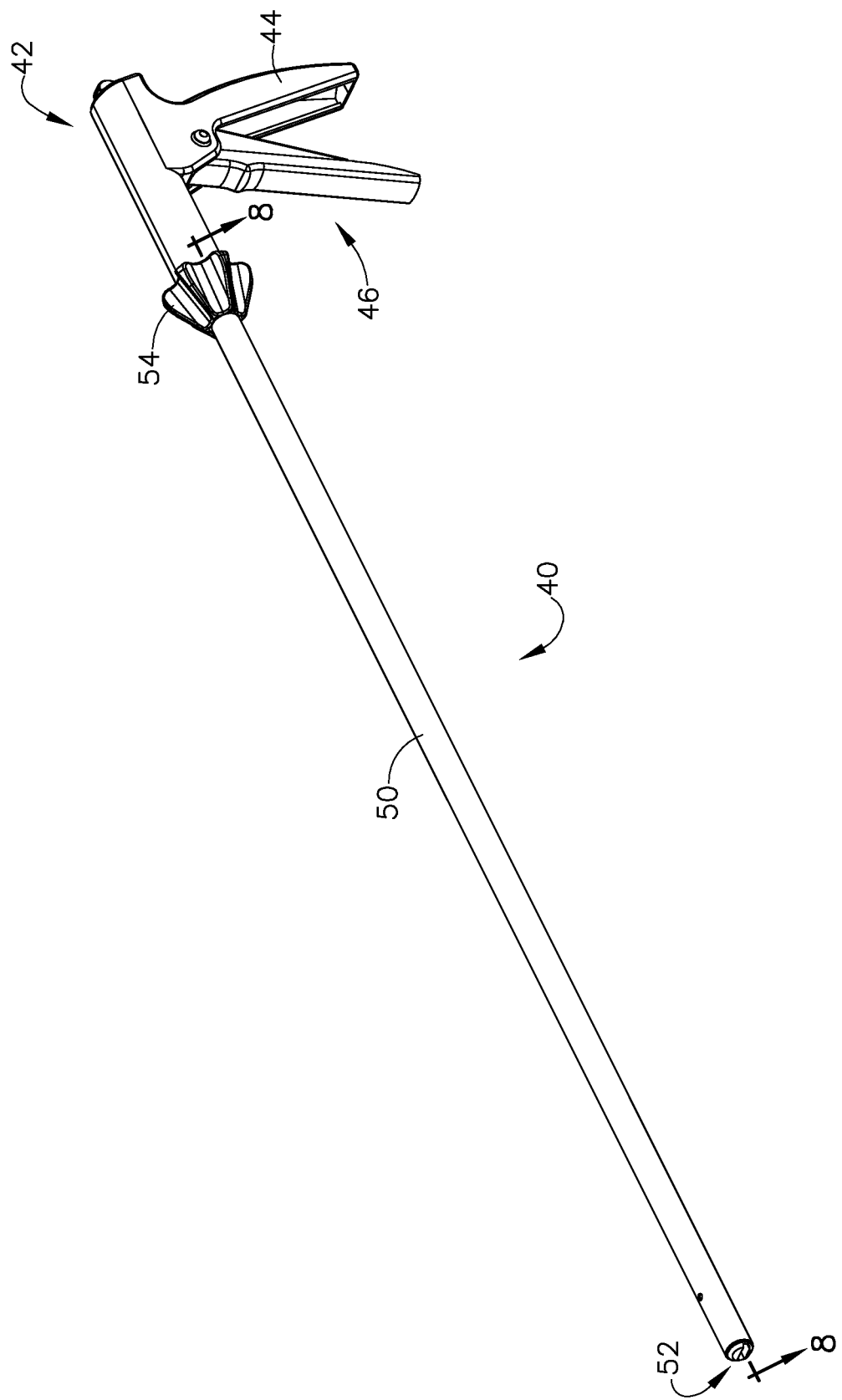
FIG. 7 is an isometric view of an exemplary low profile surgical stapler of the present invention.

Turning now to FIG. 7, which shows an exemplary low profile stapler 40 for deploying staples 10 in accordance with the invention. As shown in FIG. 7, stapler 40 includes a handle 42 having a pistol grip 44 shaped for grasping by a surgeon. An actuator assembly 46 is movably coupled to handle 42 to be drawn towards the pistol grip 44 during staple deployment. An elongated, tubular fastener housing 50 extends distally from handle 42. Housing 50 has sufficient length (on the order of 18") to enable use within an obese patient at numerous trocar access sites. Likewise, housing 50 is sized to allow for passage through a small (3-5 mm) diameter trocar although functional devices of a larger diameter are also possible without departing from the overall scope of the invention. A staple deploying assembly, described below, is disposed within the interior of housing 50 for discharging staples from a distal deployment opening 52 of the housing. Actuator assembly 46 facilitates both the advancement of staples 10 through housing 50, as well as the deployment of the staples from the distal housing end 52. Alternatively, separate actuating mechanisms may be incorporated into stapler 40 for conveying staples to the distal end of housing 50 and deploying the staples externally from the housing into adjacent tissue.

Figure 8:
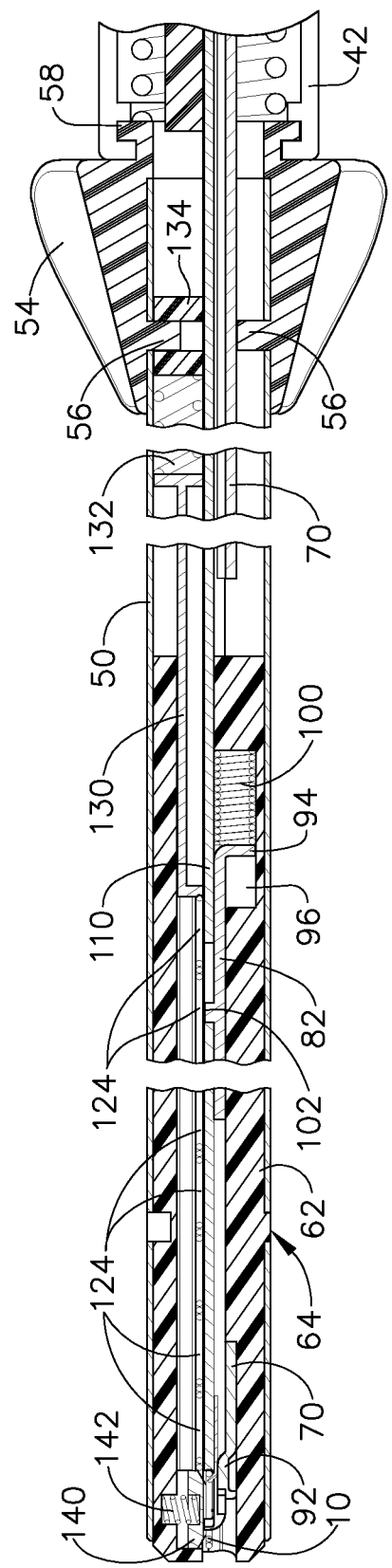
FIG. 8 is a side sectional view taken along line 8-8 of FIG. 7, showing the distal end of the stapler.

In a surgical application, stapler 40 is manipulated through a trocar (in a laparoscopic procedure) or endoscope (in natural orifice, endoluminal or transluminal procedures) so that deployment opening 52 is adjacent the tissue area to be fastened. To properly orientate staple 10 against a selected tissue area, a rotating knob 54 may be provided on handle assembly 42. As shown in FIG. 8, knob 54 includes a flange 58 which rotates within a circular slot at the distal end of handle 42 to rotate the knob relative to the handle. Additionally, knob pins 56 extend into the inner bore of knob 54 and engage an opening in the wall of housing 50. As knob 54 is rotated, housing 50 is in turn rotated by the interaction of pins 56 with the housing. It will be appreciated that a connection also exists between rotating knob 54 and the staple deploying assembly inside of housing 50, so that rotation of the knob also produces rotation of the staple deploying assembly about the longitudinal housing axis. Accordingly, as housing 50 rotates, the legs of staple 10 rotate relative to the surrounding tissue, thereby altering the position at which the staple prongs will pierce the tissue during deployment. Stapler 40 is depicted as having a rigid housing 50 for open surgical applications or laparoscopic applications using trocars. In an alternative embodiment for open surgical applications or laparoscopic applications using trocars, housing 50 is substantially rigid, but has at least one articulation joint allowing housing 50 to deflect in a controlled manner from the primary axis of housing 50 increasing the operable range of the stapler without departing from the scope of the invention. In yet another alternative, housing 50 is substantially flexible and of an increased length allowing for less invasive, natural orifice (e.g., transoral, etc.) access to regions of the patient requiring a treatment (e.g., within the peritoneal cavity of the patient).

Figure 9:
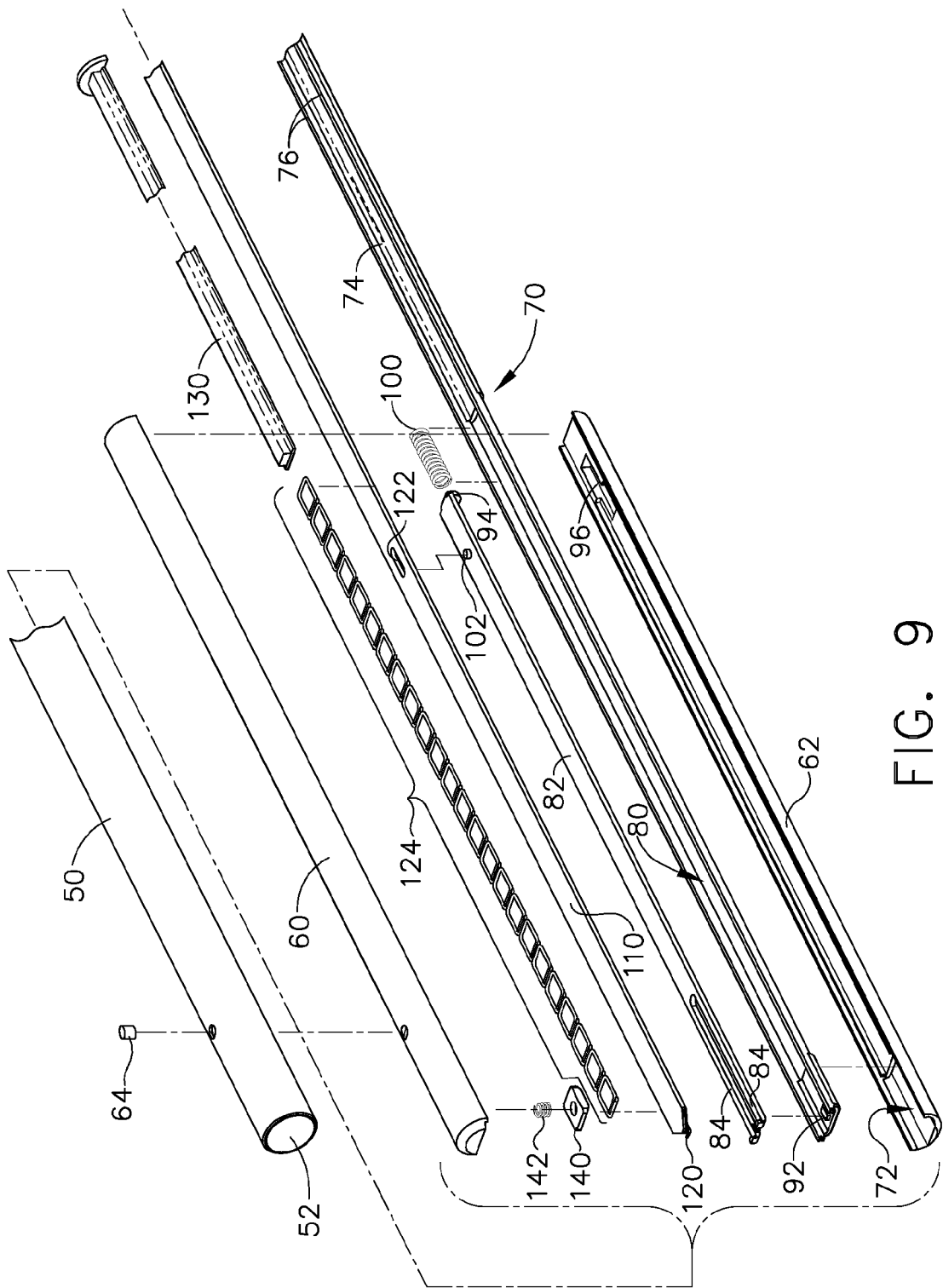
FIG. 9 is an exploded isometric view of the distal end of the stapler of FIG. 7.
Figure 10:
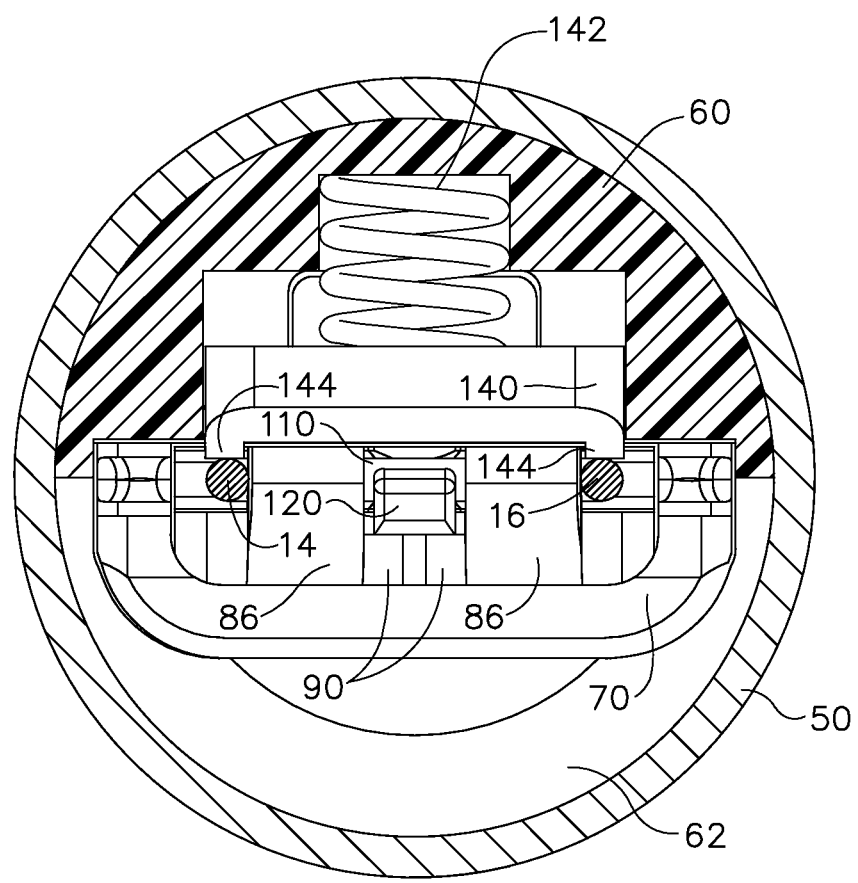
FIG. 10 is a distal end view, partially in section, of the stapler of FIG. 7.

FIGS. 8 through 10 show different views of the distal portion of the staple deploying assembly within housing 50. As shown in these views, the staple deploying assembly includes a staple guide 60 and a base guide 62 each having a semicircular outer perimeter. The staple and base guides 60, 62 join along a diametrical centerline and together extend concentrically within housing 50. Both guides 60, 62 include at least one retaining pin, indicated by reference number 64, for fixing the position of the guides within the housing. A staple former 70 extends through housing 50 along the inner surface of base guide 62. Former 70 comprises a center section 74 bounded by parallel sidewalls 76. The distal ends of sidewalls 76 preferably include a concave radius. A longitudinally extending opening 80 is provided in center section 74 to enable base guide 62 to extend partially through the former. Distal of opening 80, former 70 reciprocates within a trough 72 shaped into base guide 62. The distal edge of former opening 80 contacts the proximal end of base guide trough 72 during staple deployment to provide a proximal stop for the retracting former 70 (as shown in FIG. 9). Likewise, the proximal edge of former opening 80 contacts the proximal end of base guide 62 to provide a distal stop for the advancing former 70. A recessed area 96 is provided near the proximal end of base guide 62 for receiving an anvil base tab, as will be described below.

Figure 11:
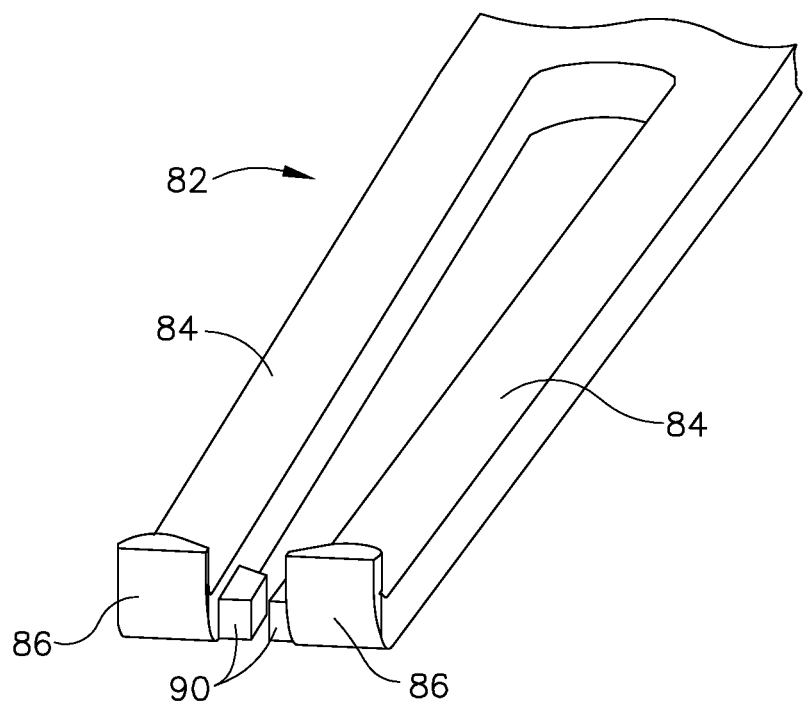
FIG. 11 is a fragmentary, isometric view of the distal end of the anvil base of FIG. 9.

An anvil base 82 extends longitudinally along the surface of former 70 on the side opposite base guide 62. Former sidewalls 76 provide a track along which the anvil base 82 slides relative to the former 70. As shown in greater detail in FIG. 11, the distal end of anvil base 82 is forked into a pair of longitudinally extending anvil spring arms 84 having an inward bias, whereby the gap between the anvil arms is smaller at the distal end of the arms than at the forking point. Each of the arms 84 terminates in an upwardly curved, staple holding anvil 86. Anvils 86 extend substantially perpendicular to the longitudinal length of arms 84. The proximal face of each anvil 86 preferably has a radius formed therein (not shown), and is rounded about the outer edge and angled distally inward towards the longitudinal centerline of the anvil. The radius formed on the proximal face of each anvil 86 helps to securely hold the staple in place during the deployment process. An anvil boss 90 is attached to each anvil arm 84 adjacent the anvil 86. In an alternative embodiment, the anvil boss 90 is attached to each anvil arm 84, but proximal to the anvil 86. Anvil bosses 90 project towards each other into the gap between the arms 84. The proximal face of each anvil boss 90 is preferably angled distally inward towards the longitudinal centerline of the anvil.

Figure 12A:
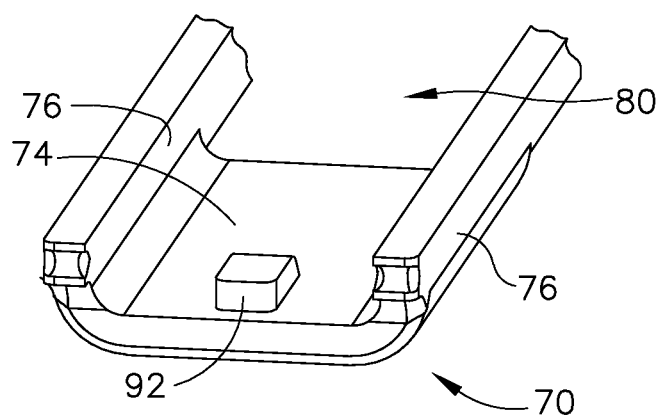
FIG. 12A is a fragmentary, isometric view of the distal end of the staple former of FIG. 9.
Figure 12B:
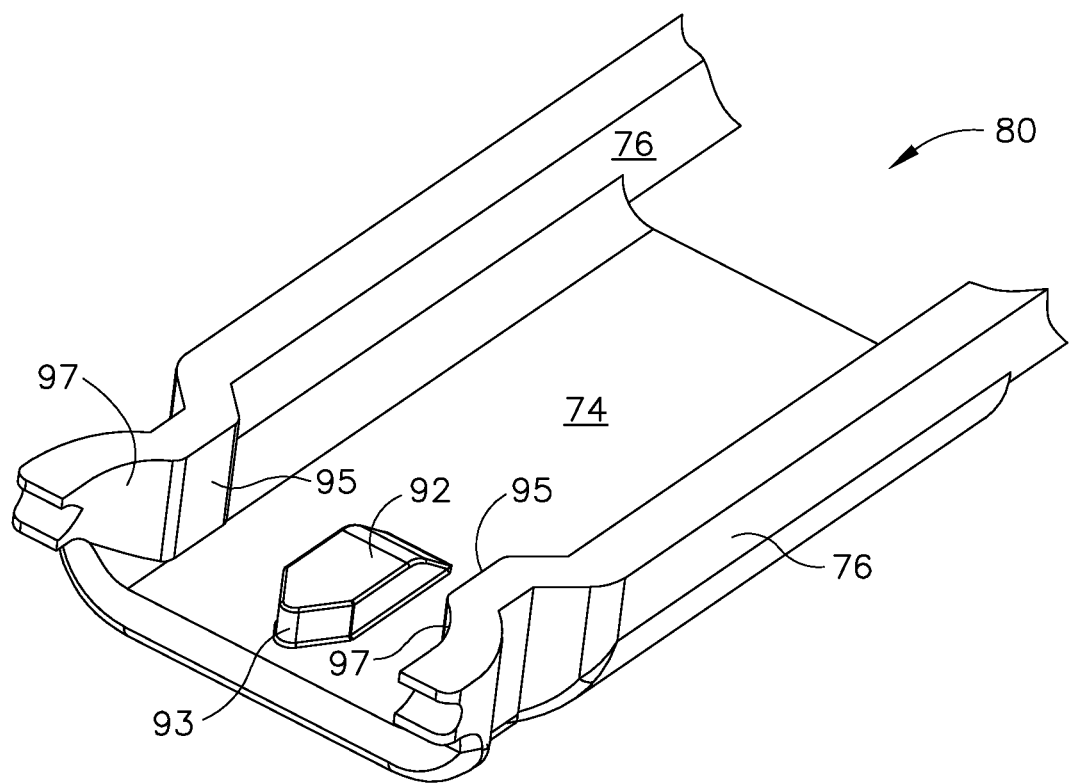
FIG. 12B is a fragmentary, isometric view of the distal end of a second embodiment of the former of FIG. 9.

As shown in FIG. 12A, an anvil arm stop 92 extends upward from the surface of former 70 adjacent the distal former end. Arm stop 92 is centered between sidewalls 76 to project upward into the gap between the anvil arms 84 during or before former 70 advances to close a staple 10 during the deployment sequence. In a preferred embodiment, arm stop 92 provides a support to maintain anvil arms 84 in an outward, spread position as the former 70 advances to close a staple 10 during the deployment sequence. FIG. 12B shows an alternative embodiment wherein arm stop 92 has a narrow distal edge 93 that increases in width in the proximal direction. Narrow edge 93 is sized to freely pass between anvil bosses 90 as former 70 is advanced and then deflects anvil arms 84 in an outward, spread position as the former 70 advances further. Arm stop 92 then again provides a support to maintain anvil arms 84 in an outward, spread position as the former 70 advances to close a staple 10 during the deployment sequence. In this alternative embodiment, anvil bosses 90 may be adjacent to anvils 86, or may be proximal to anvils 86 while attached to each anvil arm 84. Returning to FIGS. 8 and 9, the proximal end of anvil base 82 is bent downward to form a tab 94. Anvil base tab 94 passes through former opening 80 and into the recess 96 in base guide 62. A spring 100 is attached to the proximal face of anvil base tab 94 and extends between the tab and the proximal edge of recess 96 to bias the anvil base into a retracted, proximal position (as shown in FIG. 8). An anvil peg 102 projects upward from the longitudinal surface of anvil base 82. Anvil peg 102 serves to advance anvil base 82 in conjunction with the other moving components of the staple deploying assembly during the deployment sequence, as will be described in more detail below.

Figure 13:
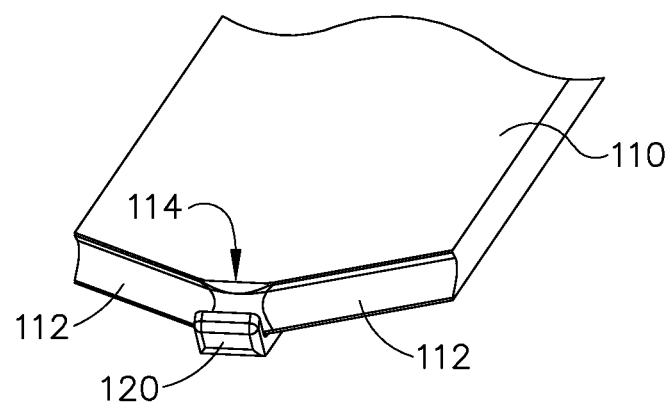
FIG. 13 is a fragmentary, isometric view of the distal end of the spreader of FIG. 9.

A spreader 110 extends longitudinally through the length of housing 50. Spreader 110 is sized to slide between former sidewalls 76 along the upper surface of anvil base 82. As shown in FIG. 13, the distal end of spreader 110 is inwardly angled, as indicated at 112, towards a center apex 114. The distal spreader end 112 and apex 114 include an inward radius to aid in holding the staple legs 14, 16 and base segment 12 against the spreader 110 as the staple is opened during the deployment sequence. While the radius may be located on the center of distal spreader end 112, in a preferred embodiment, the center of the radius is offset from the center of the end 112 in the direction of anvil base 82 to aid in staple retention. A staple retaining hook 120 is attached to the lower surface of spreader 110 and extends forward of apex 114 a distance slightly greater than the diameter of a staple 10. Hook 120 can aid in retaining the base segment 12 of a staple 10 at the distal end of spreader 110 as the staple is opened and formed during deployment. Hook 120 helps eject the deformed staple as spreader 110 is retracted at the conclusion of the deployment cycle. This is described in greater detail below. As shown in FIGS. 8 and 9, a slot 122 is formed in spreader 110 above anvil peg 102. Slot 122 has a length that is substantially equal to the distance of relative movement between the anvil base 82 and spreader 110. Anvil peg 102 moves from the distal end of slot 122 to the proximal end of the slot as spreader 110 is advanced distally during the initial stages of the deployment sequence.

Figure 14:
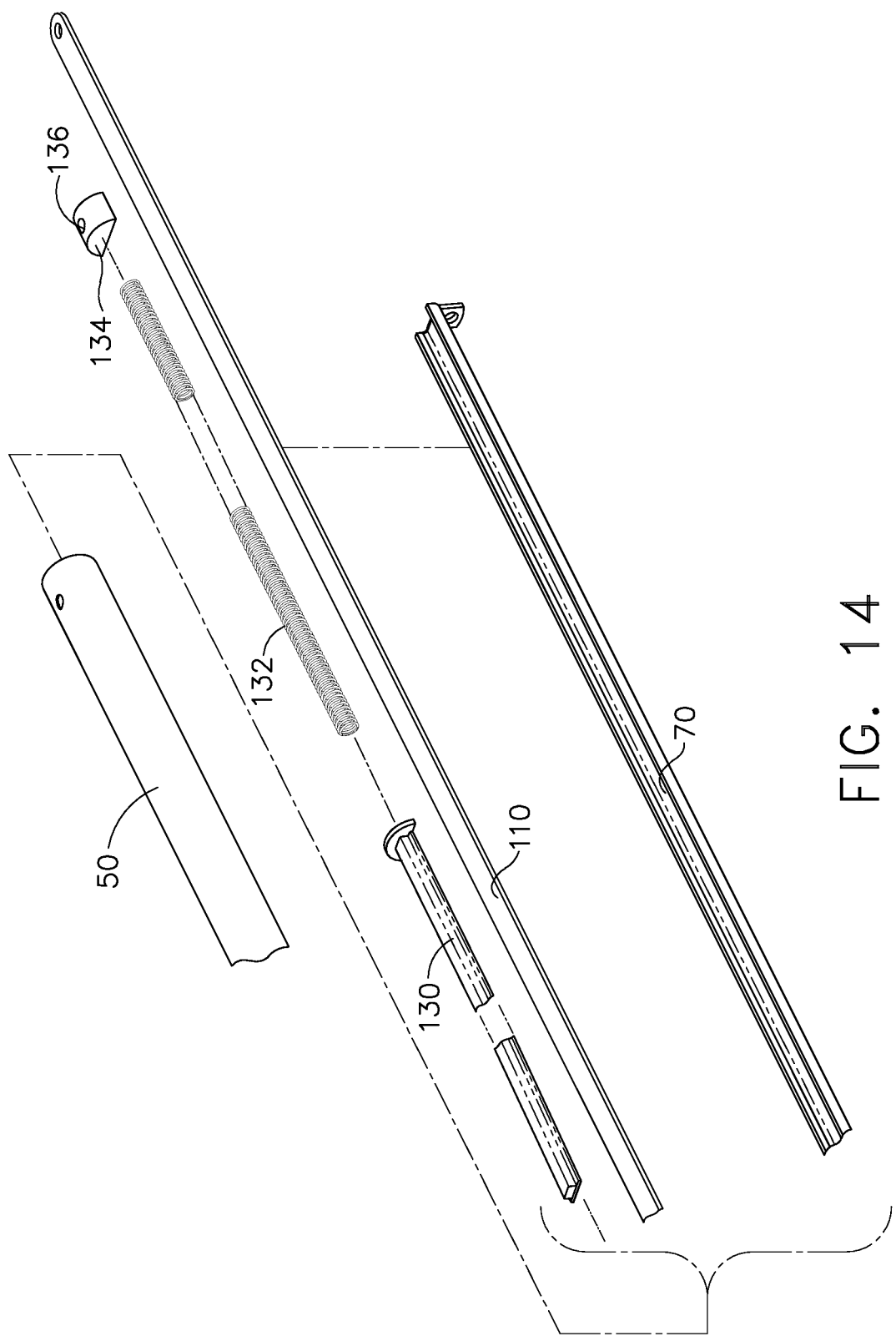
FIG. 14 is an exploded, isometric view of the proximal end of the stapler housing.
Figure 16:
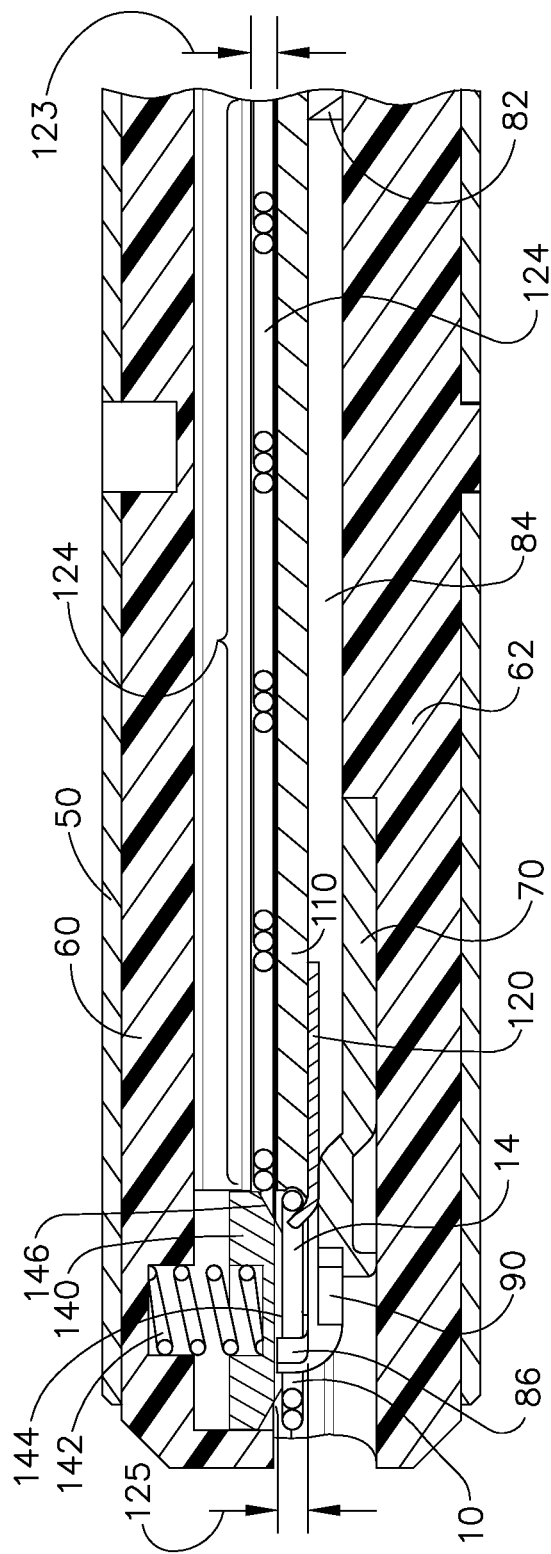
FIG. 16 is a side sectional view of the distal end of the stapler, shown in an initial, predeployment condition.

As shown in FIG. 16, a channel 123 is formed between spreader 110 and staple guide 60 for a longitudinally extending magazine stack 124 of staples 10. Staples 10 are conveyed within stack 124 to the open distal end 52 of the stapler prior to deployment. As shown in FIG. 9, within stack 124 each of the staples 10 is oriented such that the abutting end segments 20, 22 of the staple are positioned nearest the open stapler end 52. The base segment 12 of the distal-most staple abuts the end segments 20, 22 of the second staple, the base segment of the second staple abuts the end segments of the third staple, and so forth through the length of the stack 124. Within stack 124, the leg portions 14, 16 of each staple 10 are aligned substantially parallel to and in contact with the walls of staple guide 60 to maintain the forward orientation of the staples. A plurality of staples 10 can be included within the magazine stack 124, with the preferred stapler embodiment capable of holding 20 or more staples. A staple pusher 130 is located at the proximal end of the magazine stack 124 for advancing the stack through channel 123, towards the distal end of housing 50. As shown in FIG. 14, a staple advancing spring 132 is located between staple pusher 130 and a fixed spring stop 134 for biasing the staple pusher distally. Spring stop 134 includes a radial opening 136 for receiving rotating knob pin 56, to enable the staple advancing assembly to rotate with knob 54.

Figure 15:
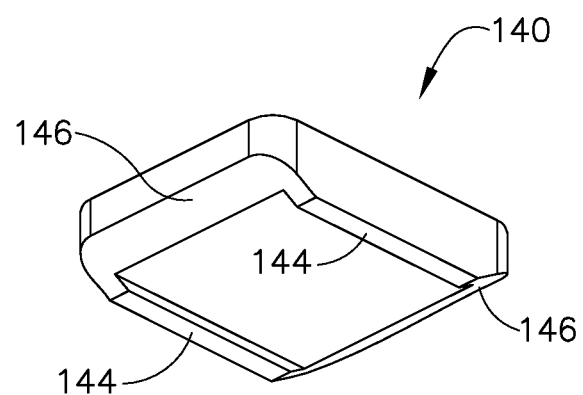
FIG. 15 is an isometric, bottom view of the shoe of FIG. 9.

As shown in FIGS. 8 through 10, a shoe 140 is provided between spreader 110 and staple guide 60, adjacent the distal end of the guide. Shoe 140 individually indexes staples 10 from stack 124. Shoe 140 moves the staples 10 from stack 124 (residing within channel 123) into a staging position within a second discharge channel 125, as shown in FIG. 16. A load spring 142 is connected between shoe 140 and staple guide 60. Load spring 142 biases shoe 140 downward, away from staple guide 60 and towards anvil arms 84 and spreader 110. Second channel 125 includes the area between shoe 140 (in a downward state) and anvil arms 84, with anvils 86 residing within the channel. As shown in greater detail in FIG. 15, shoe 140 includes a pair of downwardly extending side rails 144. Side rails 144 are spaced apart a distance substantially equal to the distance between staple legs 14, 16 when staple 10 is in the initial loop shape. Between side rails 144, the body of shoe 140 is recessed upward to enable anvils 86 to pass between the side rails during staple deployment. The distal and proximal end faces of shoe 140 are beveled, as indicated by reference numeral 146, leading to side rails 144. When biased downward, the beveled shoe ends 146 extend across the path of spreader 110.

Figure 17:
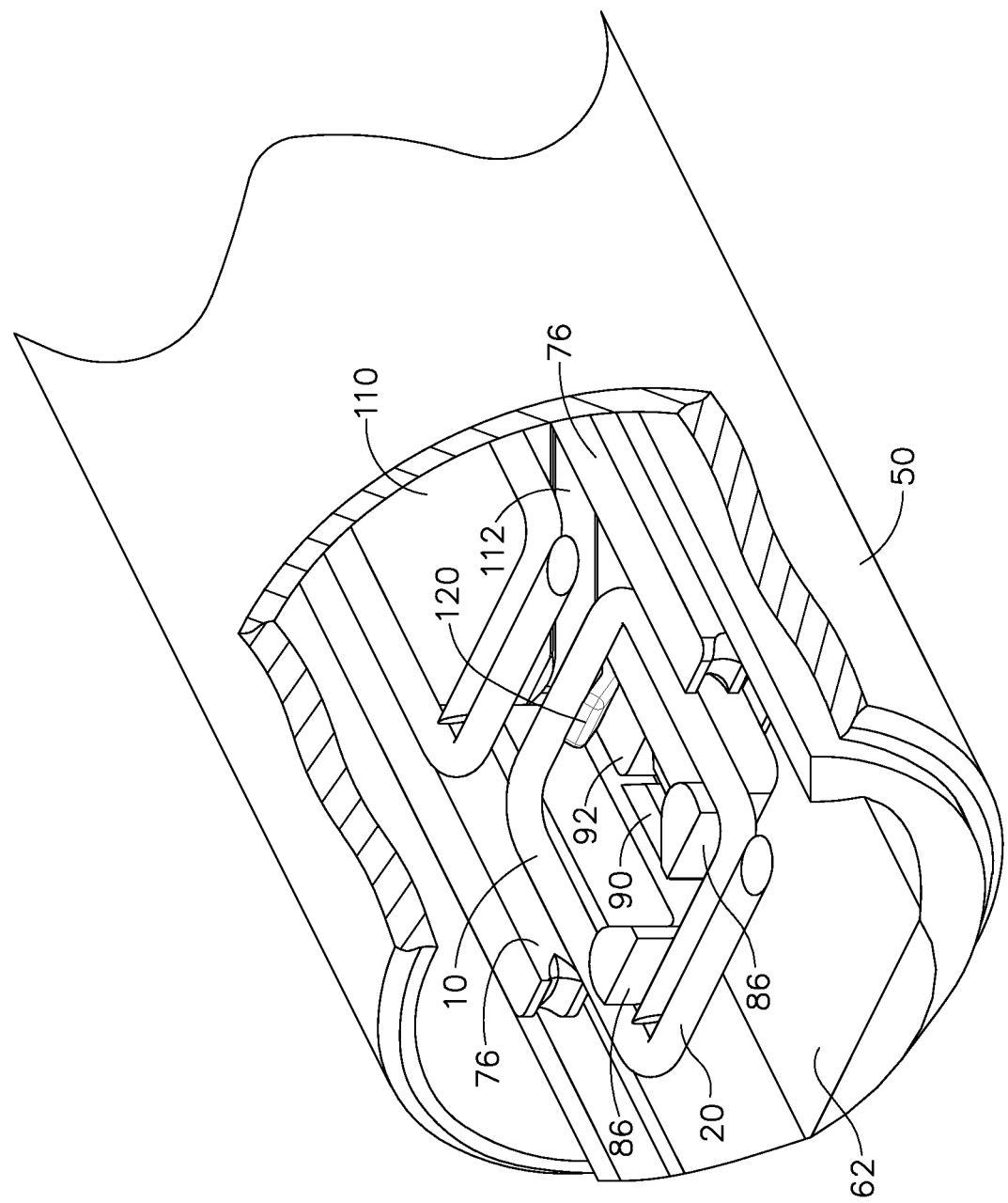
FIG. 17 is an isometric view of the distal end of the stapler in the initial, predeployment condition, shown with the staple guide, shoe and load spring removed, and the outer housing partially cut away for clarity.

In an initial, pre-fire position shown in FIG. 16, shoe 140 is just distal of the staple stack 124, and above the individual staple 10 staged within discharge channel 125. In this position, load spring 142 pushes shoe side rails 144 down onto legs 14, 16 of the staged staple to hold the staple in position. As shoe 140 pushes down on staple 10, anvils 86, which are in the initial, inwardly-biased position, and hook 120 extend up through the interior of the staple. FIG. 17 shows in greater detail a staged staple 10 held by anvils 86. In addition to applying a downward force on the staged staple, shoe 140 provides a distal stop for the staple stack 124, which is biased distally by staple pusher 130.

During the deployment sequence, spreader 110 moves distally through discharge channel 125, advancing the staged staple distally away from shoe 140. As spreader 110 advances, the proximal end of shoe 140 is lifted up against the force of load spring 142 by the contact between the advancing spreader and the proximal, beveled shoe end 146. The lifting of shoe 140 enables the distal most staple in stack 124 to move forward within channel 123, in response to the force of staple pusher 130, past beveled shoe end 146 and underneath the shoe. As the staple moves underneath shoe 140, the shoe side rails 144 push the staple legs 14, 16 down onto spreader 110. The staple remains in channel 123, between shoe 140 and spreader 110, during the deployment of the previous staple. As the distal-most staple moves under shoe 140, the remaining staple stack 124 advances distally one staple length within channel 123. When spreader 110 retracts following firing, shoe 140 pushes the staple downward into the discharge channel 125, and onto the retracting anvils 86, thereby staging the staple for the next deployment sequence.

Figure 18:
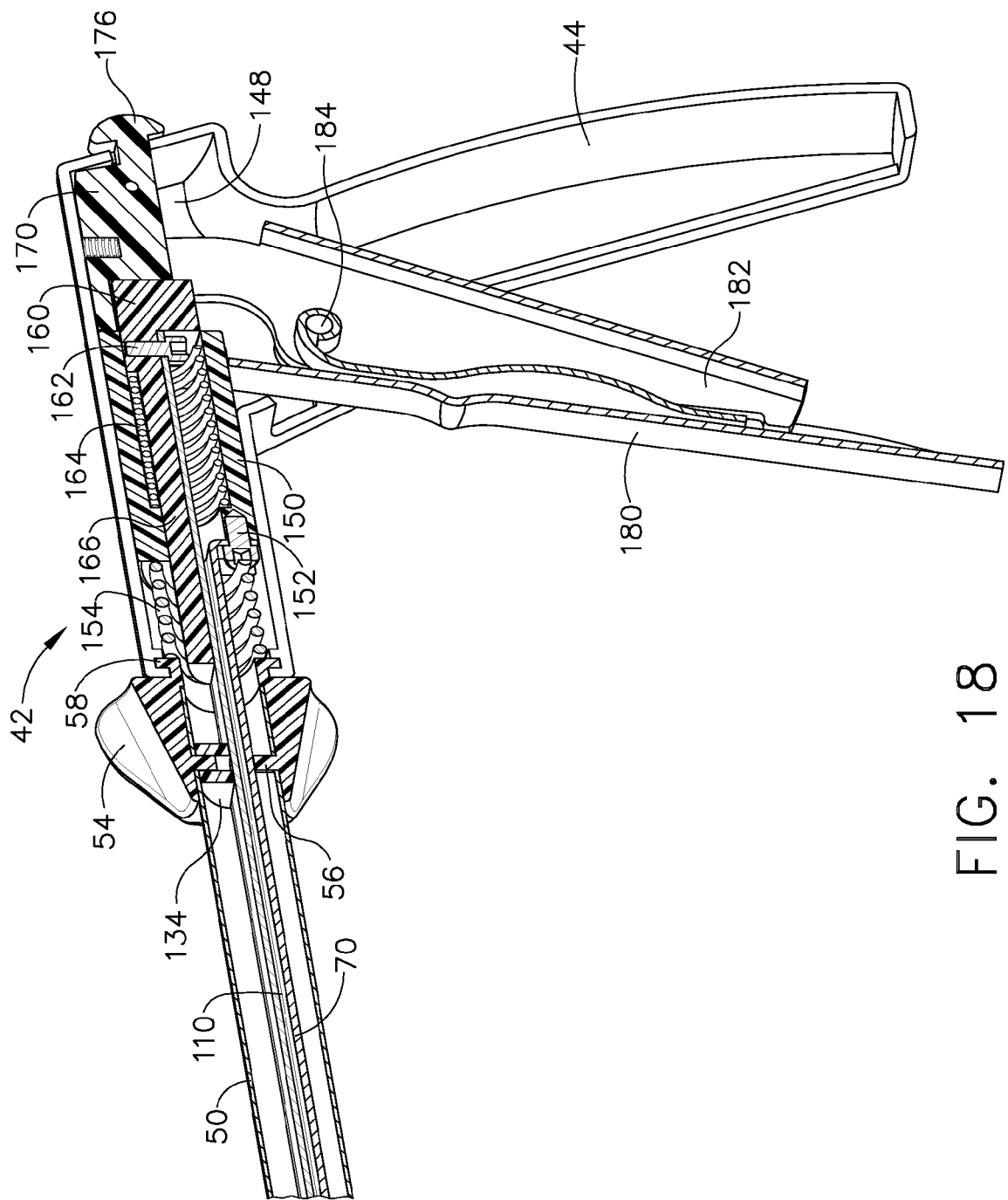
FIG. 18 is an isometric view in section of the proximal end of the stapler shown in FIG. 7.
Figure 19:
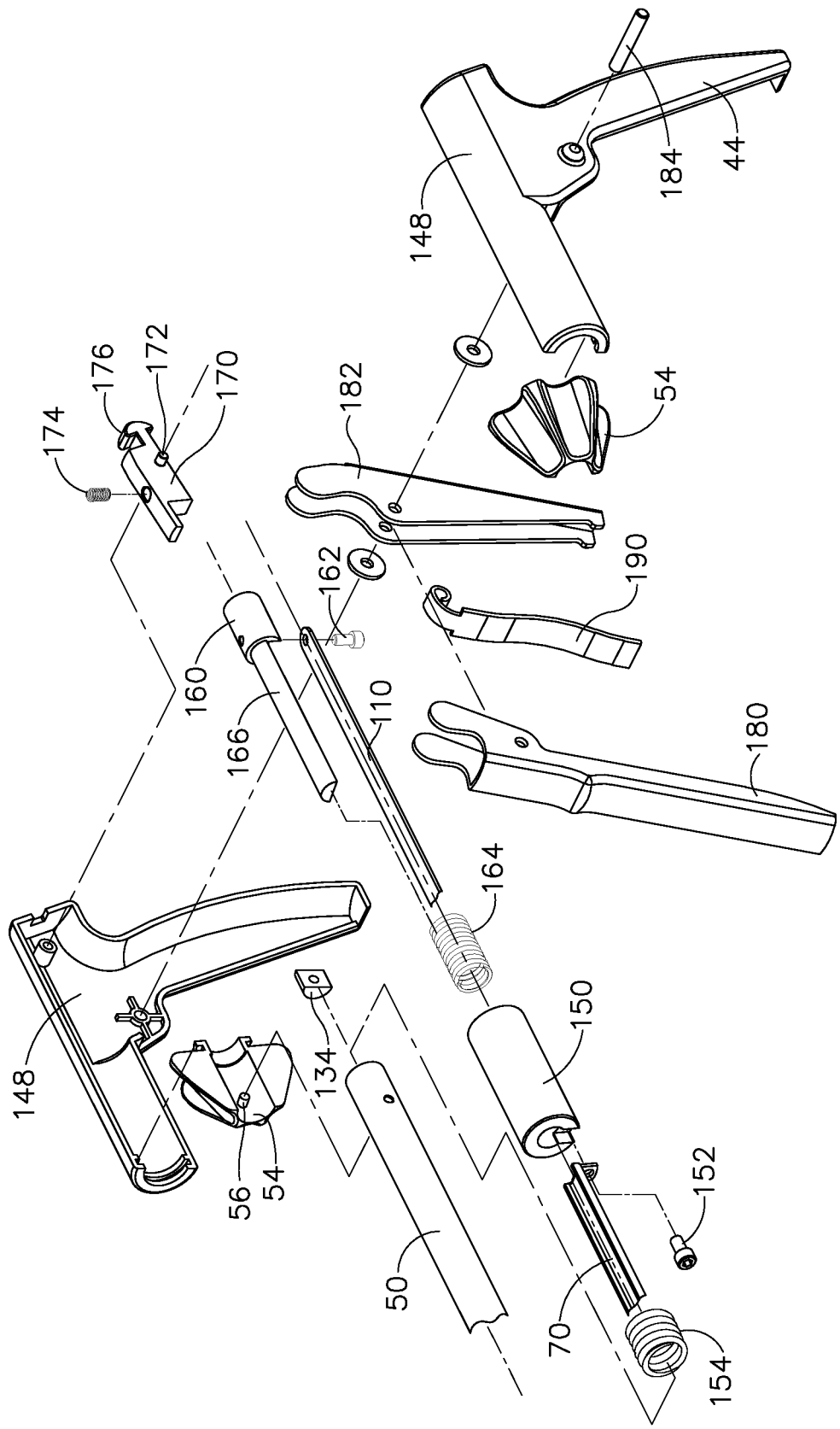
FIG. 19 is an exploded, isometric view of the proximal stapler end shown in FIG. 18, with the top portion of the rotation knob, staple spring stop, and outer tube rotated 90° for clarity.

Turning now to FIGS. 18 and 19, which show the proximal end of stapler 40 including handle 42. Handle 42 comprises a housing 148 formed in sections which are joined together during the manufacturing process by any of a number of suitable means known in the art. As mentioned above, rotating knob 54 is connected at the distal end of handle housing 148 for rotation relative to the handle. Fastener housing 50 extends proximally into the bore of rotating knob 54, with the housing end abutting against a stepped edge in the bore. In FIG. 19, rotating knob 54, staple pusher spring stop 134 and fastener housing 50 are rotated 90° relative to the other components to show the interior of the knob bore. The proximal end of former 70 extends through the open end of fastener housing 50 and into handle housing 148. Within handle housing 148, the former end is fixed to the distal end of a cylindrical, former bushing 150 by a screw 152 or other attachment means. A former spring 154 encircles former 70 and contacts the distal face of former bushing 150 for biasing the bushing into a proximal, retracted position. Spreader 110 extends through former spring 154 and former bushing 150 and is attached at the proximal end to a spreader driver 160 by a screw 162 or other attachment means. A spreader spring 164 encircles spreader 110 distal of driver 160. A spring guide 166 extends through spreader spring 164 for orienting the spring about the inner circumference of former bushing 150. As shown in FIG. 18, spreader spring 164 extends between a stepped edge inside former bushing 150 and spreader driver 160 to bias the driver into a proximal, retracted position.

A locking member 170 engages the proximal ends of former bushing 150 and spreader driver 160. A pivot pin 172 extends from both sides of locking member 170 to pivotably connect the locking member between the sides of handle housing 148. Pin 172 enables locking member 170 to pivot up and down within the handle housing 148. A lock spring 174 biases locking member 170 downward to move the distal tip of the locking member to the proximal end of spreader driver 160 as the spreader driver is advanced distally. A toggle button 176 extends from locking member 170 through an opening in the proximal end of handle housing 148. Button 176 enables manual resetting of locking member 170 at any time following staple opening.

Figure 20:
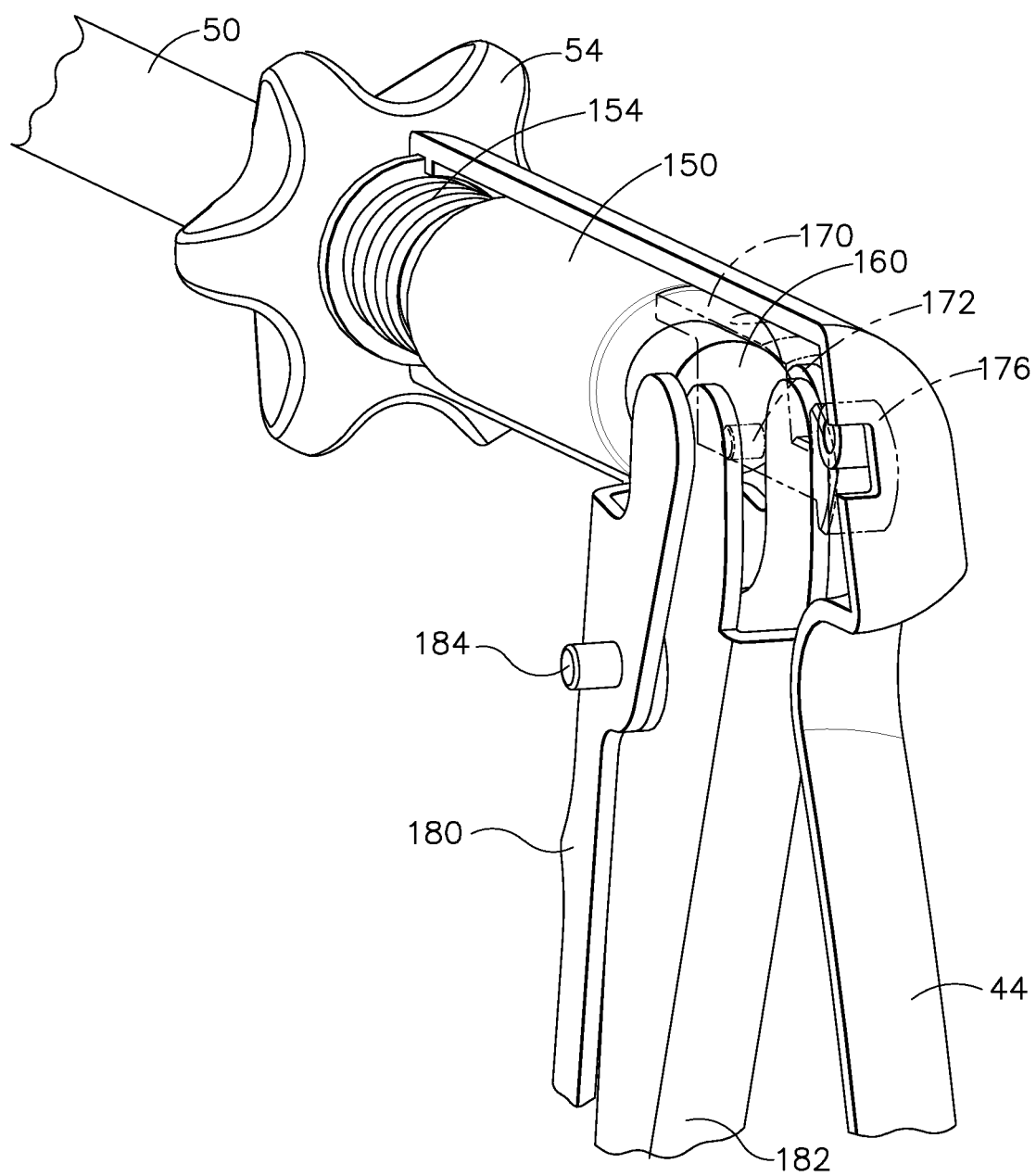
FIG. 20 is an isometric, proximal end view of the stapler of FIG. 18, shown with the left handle housing removed and the locking member in phantom for clarity.

Actuator assembly 46 includes a primary firing trigger 180 and a secondary firing trigger 182. Primary trigger 180 has a channel-shaped frame that opens proximally. Secondary trigger 182 also has a channel-shaped frame that is oriented to open distally. Secondary trigger 182 is sized to fit within the primary trigger 180 through the proximal open side of the trigger frame. The upper ends of primary trigger 180 and secondary trigger 182 are rounded and extend into handle housing 148. As shown in FIG. 20, the upper end of the secondary trigger 182 is initially positioned against the proximal end face of spreader driver 160, while the upper end of primary trigger 180 is positioned to the sides of the secondary trigger end, and aligned to contact the proximal end face of former bushing 150 when the upper trigger end is pivoted distally. A pivot pin 184 extends between the sides of handle housing 148 and through the primary and secondary triggers 180, 182, to connect the actuator assembly to the handle. Primary and secondary triggers 180, 182 pivot about pin 184 relative to the housing 148. As shown in FIGS. 18 and 19, pivot pin 184 also extends through the first end of a leaf spring 190 to attach the spring to the triggers 180, 182. Leaf spring 190 is located between the channel walls of secondary trigger 182. The second end of leaf spring 190 is lodged against the inner, proximal side of primary trigger 180 (as shown in FIG. 18). When the grip of primary trigger 180 is squeezed, the curved surface of leaf spring 190 transfers the squeezing force on the primary trigger to the secondary trigger 182 to pivot both triggers about pin 184 and, thereby, rotate the upper ends of the triggers distally within handle housing 148.

To deploy a staple 10, stapler 40 is inserted through a small diameter trocar port or endoscope to reach the desired tissue area inside a body cavity. At the appropriate tissue location, stapler end 52 is placed adjacent the tissue or tissue fold to be stapled, with rotating knob 54 being turned as necessary to position the staple prongs 26. When stapler 40 is appropriately aligned, primary trigger 180 is manually squeezed in the direction of pistol grip 44 to initiate staple deployment. In the initial deployment position shown in FIGS. 21 and 22, the upper lobes of secondary trigger 182 contact the proximal end of spreader driver 160, while the upper lobes of primary trigger 180 are spaced proximally from the end of former bushing 150 by a dwell gap, indicated by reference numeral 200. The dwell gap 200 allows spreader 110 and anvil base 82 to be advanced by secondary trigger 182 prior to the advancement of former 70 by primary trigger 180. At the initial squeezing of the actuator assembly, spreader 110 is in a proximal-most position, in which spreader hook 120 is just distal of the base segment of the staged staple 10, inside the open end of the stapler. Anvil base 82 is held in a retracted position by the placement of anvil peg 102 at the distal end of spreader slot 122. Anvils 86 extend up into the folded, staged staple 10. Former 70 is also in a proximal-most position, in which the distal edge of the former opening 80 abuts the proximal end of base guide trough 72.

Figure 23:
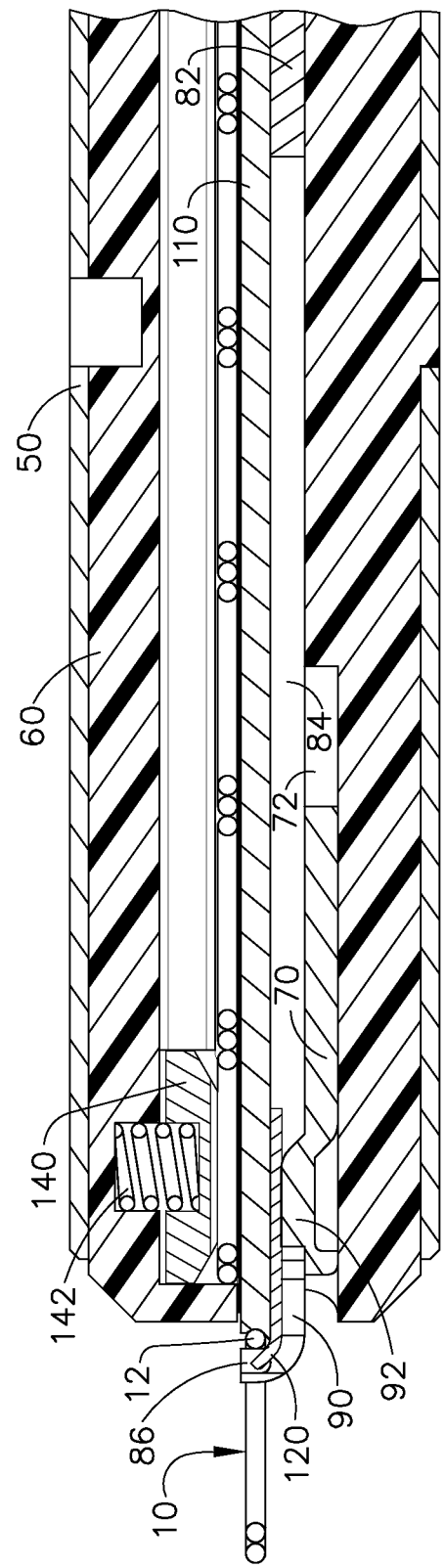
FIG. 23 is a side sectional view of the distal end of the stapler, showing a staple advanced outside the open stapler end during the deployment sequence.

As primary trigger 180 is squeezed, the trigger pivots about pin 184, as shown in FIG. 21, in turn pivoting secondary trigger 182 through the interaction of leaf spring 190. As secondary trigger 182 pivots, the upper lobes of the trigger apply pressure against spreader driver 160 to push the driver and, in turn spreader 110, distally within the stapler. Spreader driver 160 moves when the squeezing force on the actuator assembly exceeds the compression force of spreader spring 164. As spreader driver 160 moves distally, compressing spreader spring 164, spreader apex 114 engages the staged staple 10 and moves the staple distally within discharge channel 125, and through the open end 52 of the stapler. As spreader 110 is pushed distally, the spreader contacts the beveled, proximal end of shoe 140, lifting the shoe against the downward force of load spring 142. As shoe 140 is lifted, the distal-most staple in stack 124 advances forward and under the shoe. The staple moves under shoe 140 in response to the distally directed force of staple pusher 130. As shown in FIG. 23, when spreader 110 advances out the open housing end, the distal-most staple in stack 124 is held beneath shoe 140 by side rails 144, against the distal end of staple guide 60.

Figure 24:
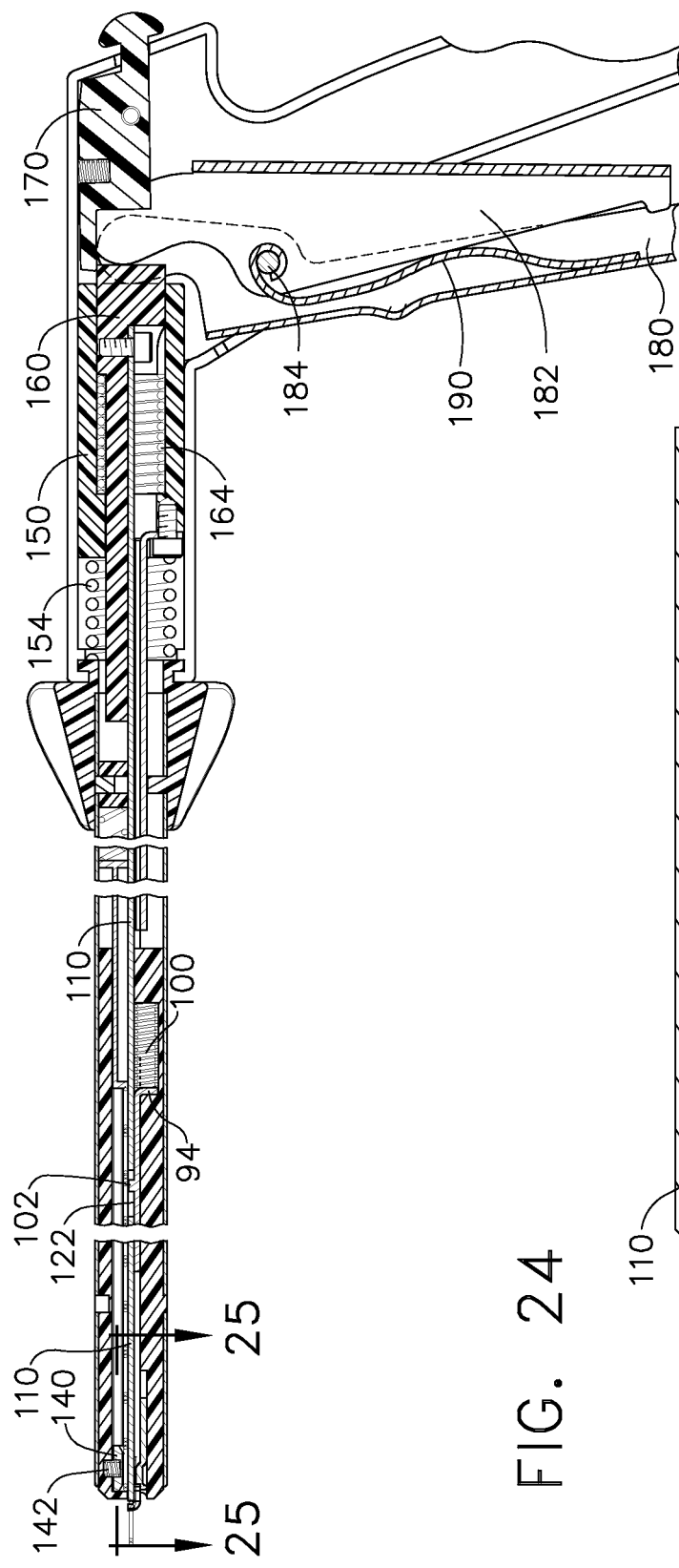
FIG. 24 is a side sectional view of the stapler showing the position of the stapler components when a staple is advanced outside the open stapler end, as shown in FIG. 23.
Figure 25:
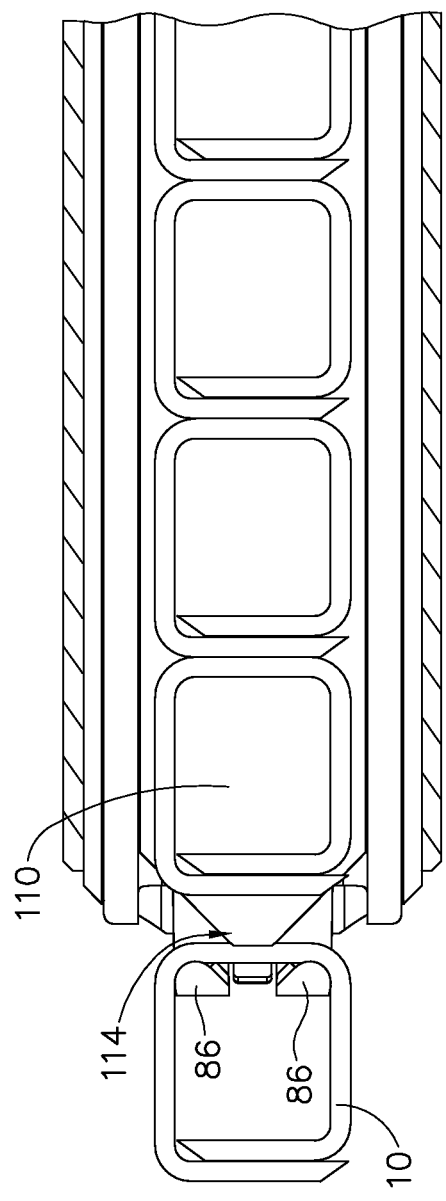
FIG. 25 is a distal end sectional view taken along line 25-25 of FIG. 24.
Figure 26:
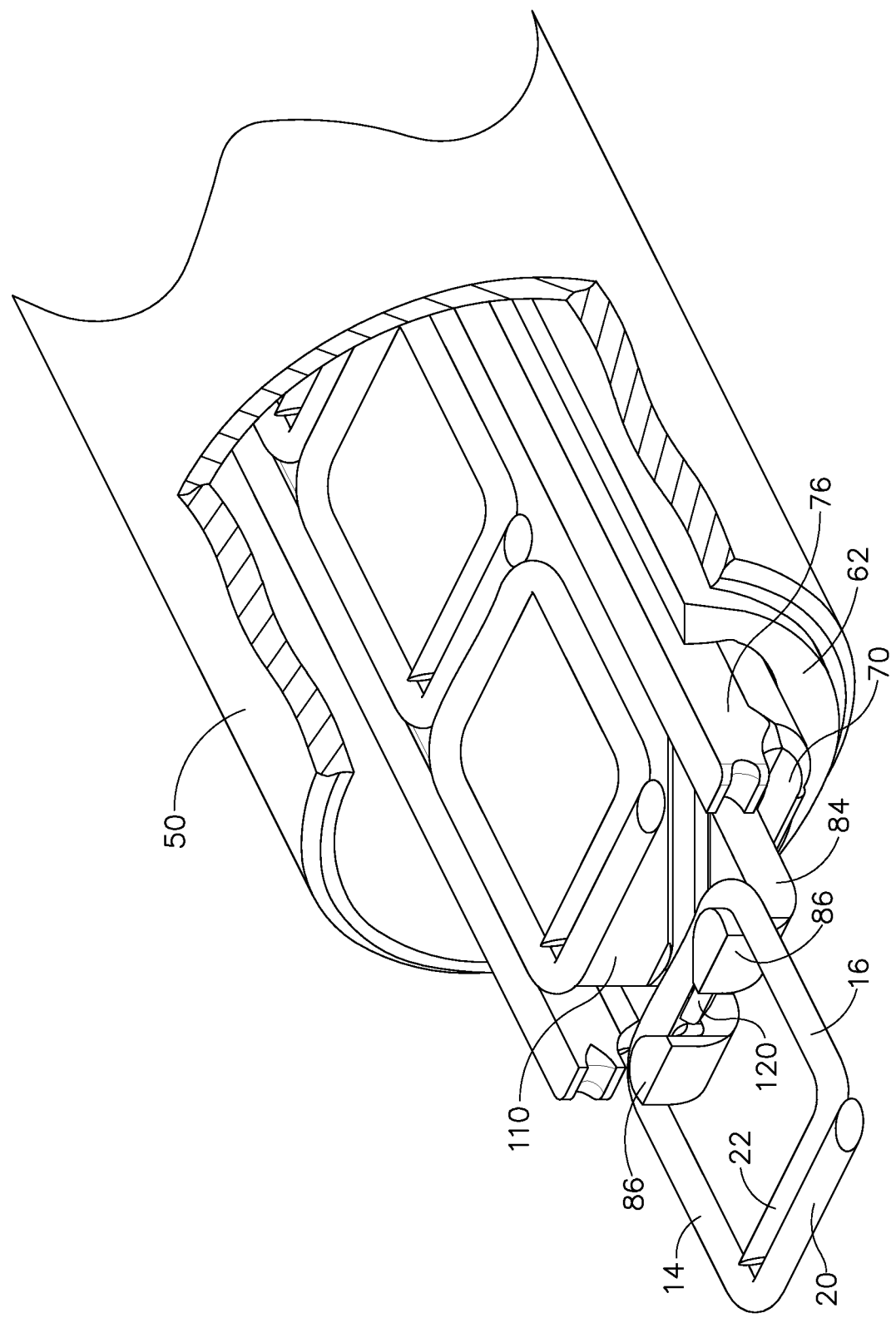
FIG. 26 is an isometric view of the distal end of the stapler, similar to FIG. 17, showing a staple held by the spreader and anvils in a fully advanced position outside the open stapler end.
Figure 27:
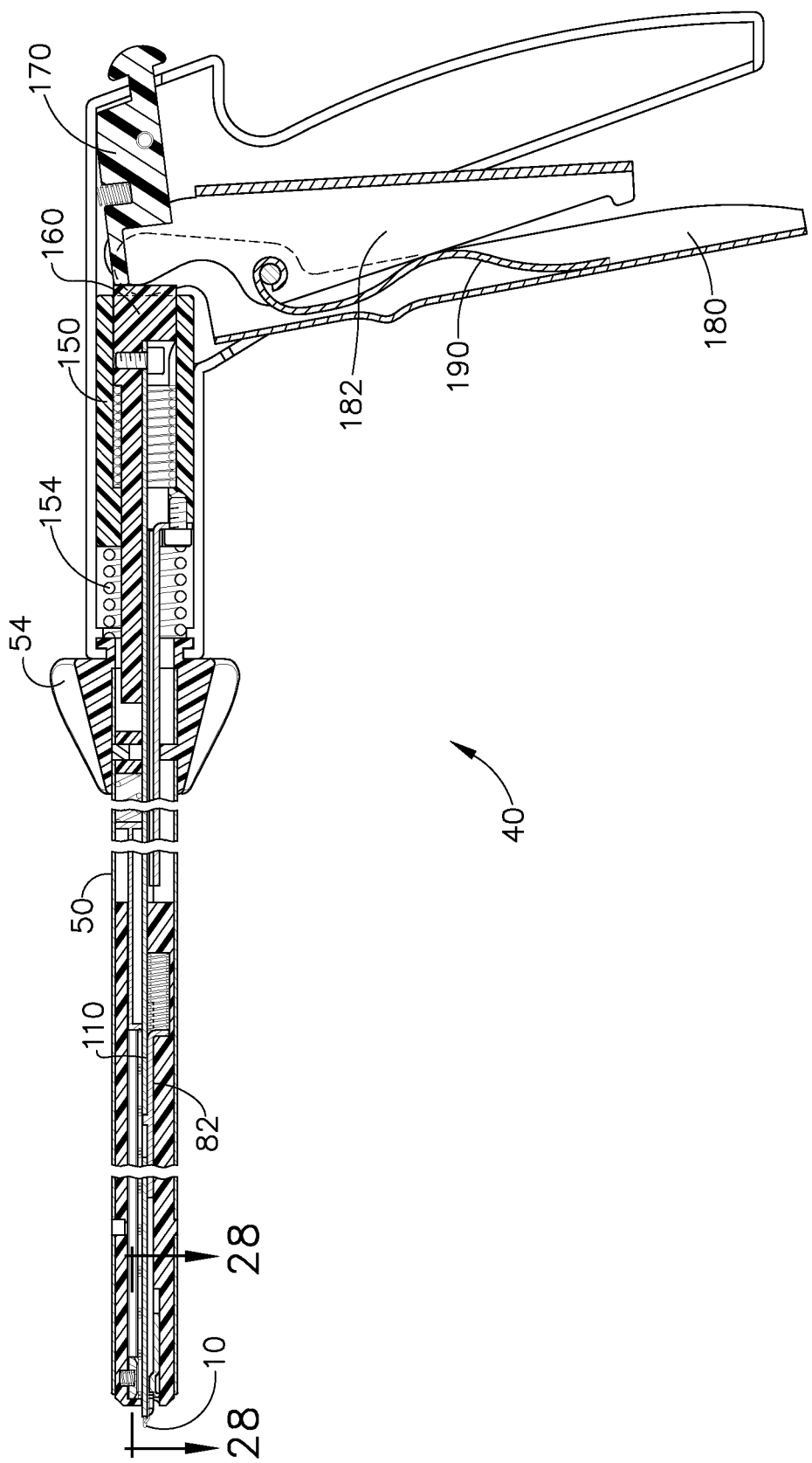
FIG. 27 is a side sectional view of the stapler, similar to FIG. 24, showing an intermediate deployment position in which the advanced staple is expanded open.

As spreader 110 moves distally, anvil peg 102 is released within slot 122, allowing anvil base 82 to also move distally under the force of anvil base spring 100, as shown in FIG. 24. As anvils 86 and the staged staple 10 progress through the distal stapler opening, the anvils remain inwardly biased, and move within the staple from adjacent the end segments 20, 22 (as shown in FIG. 22), to the intersection between the staple legs 14, 16 and base segment 12 (as shown in FIGS. 25 and 26). With staple 10 held outside the open end of the stapler between, spreader apex 114, and anvils 86, anvil base tab 94 bottoms out against the distal end of base guide recess 96, stopping further distal movement of the anvils. When anvil base 82 reaches its fully distal position, as shown in FIG. 27, the base segment of staple 10 is firmly held between the concave face of spreader apex 114 and the concave proximal face of anvils 86. After anvil base 82 reaches its distal stop, secondary trigger 182 continues advancing spreader 110 relative to the anvil base, as spreader slot 122 slides past anvil peg 102. As spreader 110 advances, spreader apex 114 moves between anvils 86, pushing the anvils outward against the staple. Anvils 86 push against the inside edges of staple 10 at the intersections between staple legs 14, 16 and base segment 12, thereby rigidly holding the staple in position on the anvils.

Figure 30:
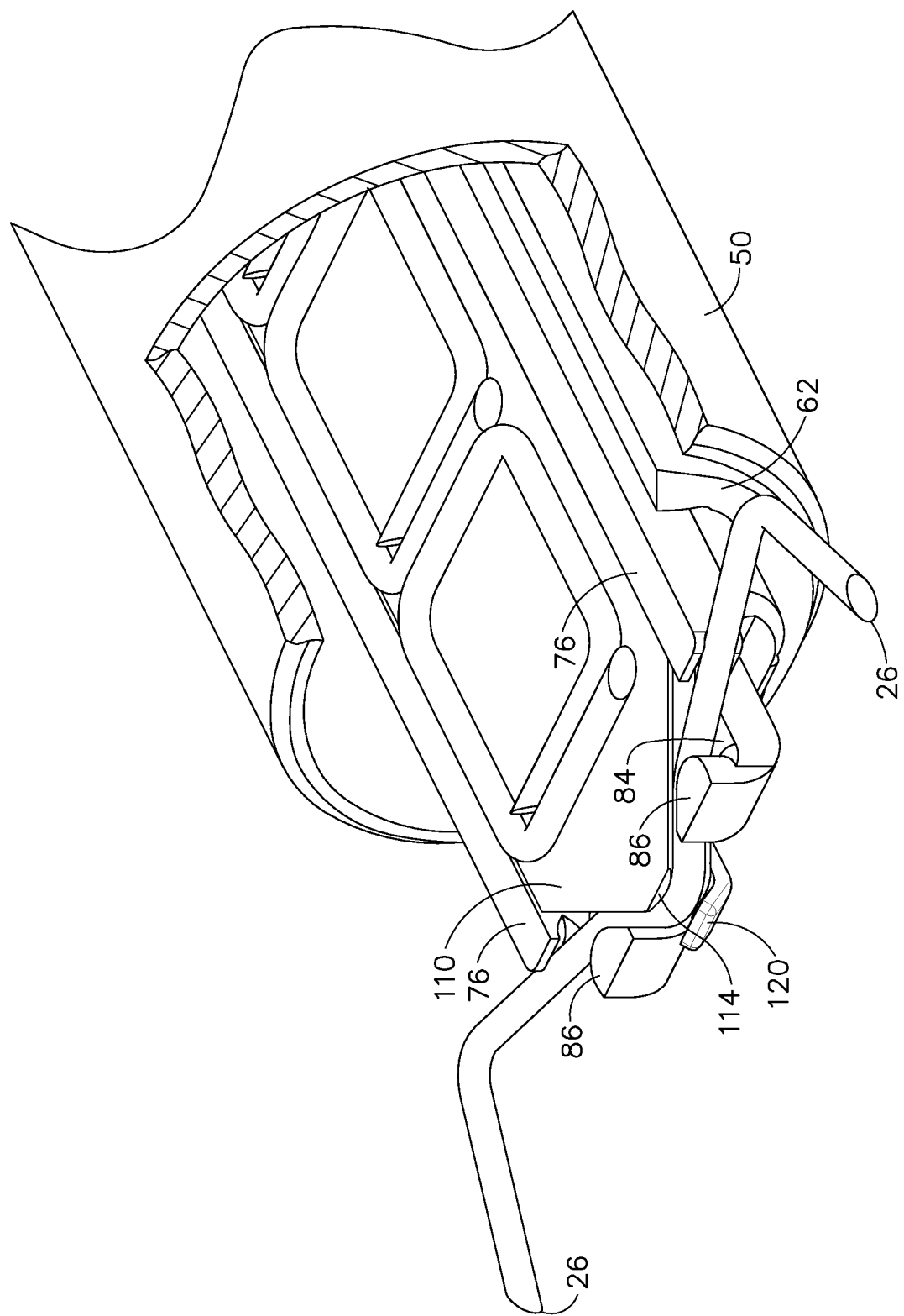
FIG. 30 is an isometric view of the distal end of the stapler, similar to FIG. 17, showing an advanced, expanded staple held outside the open stapler end by the anvils, spreader and former during the deployment sequence with the anvils spread to a full width.

While secondary trigger 182 is pushing spreader 110 distally, the upper lobes of primary trigger 180 pass through the dwell gap 200, and begin to push against former bushing 150. The force of primary trigger 180 on former bushing 150 drives former 70 distally about the bottom and sides of anvil base 82. Former 70 advances along the outside of anvil arms 84 as spreader apex 114 moves between anvils 86, allowing the former to stabilize and prevent over bending of the anvil arms during staple expansion. With base segment 12 of the staple held fixed at opposite ends within the proximal facing radius of anvils 86, as shown in FIG. 26, the advancing spreader apex 114 applies a distally directed force to the base segment between the anvils. As shown in FIGS. 28 through 30, the distally directed force of spreader apex 114 (indicated at numeral 202) drives anvil arms 84 out laterally, as indicated by arrows 204. As anvil arms 84 are moving laterally, staple legs 14, 16 are pulled open by the force of spreader apex 114 against the fixed staple back span. As staple 10 is expanding open, staple legs 14, 16 bend back against the distal ends of former sidewalls 76. The angle at which staple legs 14, 16 bend open against former 70 can vary, from approximately normal to the direction of the spreader force, as indicated by line 206, to the angle of the spreader tip, as indicated by line 208. The bend angle varies depending upon the position of the former 70 as the staple is expanded open. As the bend angle of the staple legs varies, the open angle of prongs 26 also varies, as indicated at 209. In a preferred embodiment, open angle 209 is approximately zero degrees. In an alternative embodiment, open angle 209 is greater than zero degrees.

Staple 10 bends open at two points along base segment 12, with both points occurring opposite the proximal faces of anvils 86, just inside of the intersections between the base segment and staple legs 14, 16. As staple 10 expands open from its initial closed-form shape, prong tips 26 move from an inward, overlapping position to the open, spread position described above, producing an increased width dimension in the staple. The substantial increase in width between the closed, folded staple condition and the open, expanded staple condition enables the staple to obtain a substantial tissue purchase while utilizing a small diameter delivery shaft. As staple legs 14, 16 expand open, the legs engage the radii at the distal ends of former sidewalls 76. Although not shown, two methods that can achieve this result are expanding the staple until the staple engages former sidewalls 76, or the staple can be expanded and former 70 advanced to engage the staple. In both cases, the sidewall radii serve to further laterally stabilize the expanded staple, so that the staple is held fixed between the sidewalls, anvils 86, and spreader apex 114. With staple 10 fully expanded and stabilized, and prongs 26 facing distally, the staple can be pushed forward by stapler 40 to pierce the intended tissue or material.

Figure 31:
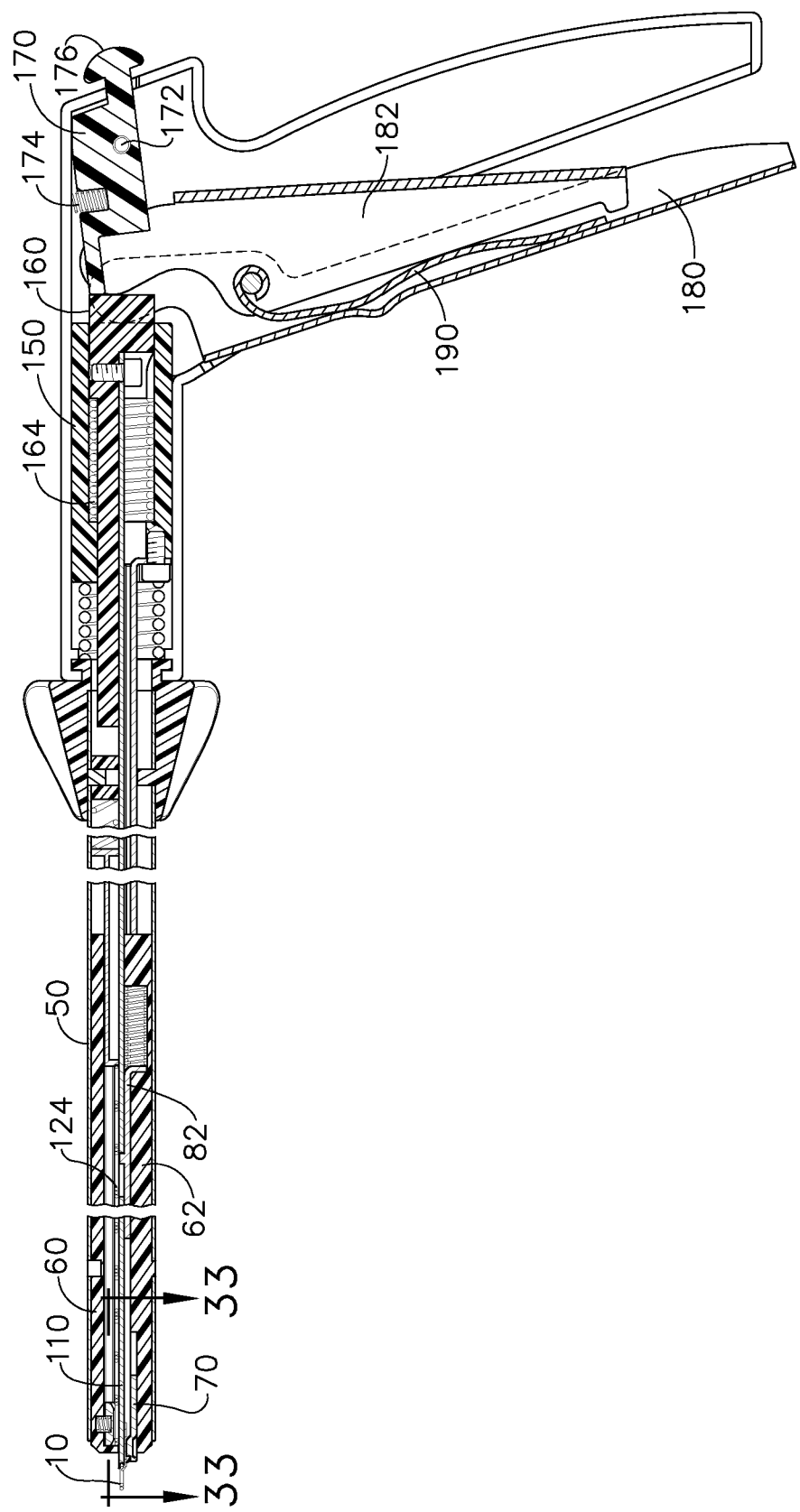
FIG. 31 is a side sectional view of the stapler, similar to FIG. 27, showing the former in a fully advanced position to fold the staple closed during the deployment sequence.

As spreader 110 expands staple 10 open, anvil peg 102 bottoms out against the proximal end of spreader slot 122, preventing further distal movement of the spreader. With spreader 110 at its fully distal position, the distal tip of locking member 170 is cleared to pivot down into contact with the proximal face of spreader driver 160, as shown in FIG. 31. The contact between locking member 170 and spreader driver 160 holds spreader 110 in the distal position, with the expanded staple exposed out the open end of the stapler. The engagement of locking member 170 with spreader driver 160 provides a pause in the deployment sequence for insertion of the expanded staple into tissue while allowing pressure on the primary trigger 180 to be relaxed. The movement of locking member 170 against spreader driver 160 can produce audible or tactile feedback informing the surgeon that the staple is expanded and ready for tissue insertion. Additional tactile feedback is also provided through an increase in squeezing resistance from the locked secondary trigger 182 and leaf spring 190.

Figure 32:
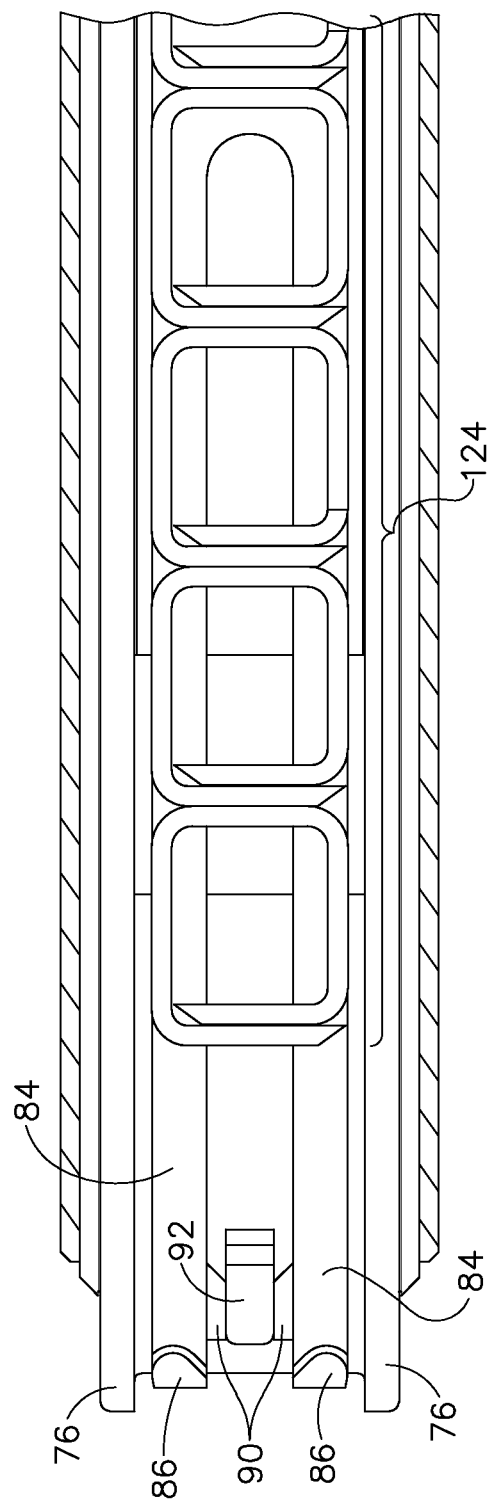
FIG. 32 is a distal end sectional view of the former and anvils, showing the relative locations of the anvil bosses and anvil stop when the former and anvils are both in a fully distal position.

To close the expanded staple, additional squeezing pressure is applied to primary trigger 180, to push the trigger lobes against former bushing 150, and advance former 70 further distally. As former 70 continues moving distally, anvil stop 92 on the former moves through the gap between anvil arms 84, and between anvil bosses 90, as shown in FIG. 32. The positioning of anvil stop 92 between anvil bosses 90 locks anvil arms 84 in the outward position, and prevents the arms from retracting inward as the staple is formed around the anvils. As former 70 advances distally, former sidewalls 76 push against expanded staple legs 14, 16, forcing the legs to bend distally about the fixed anvils 86. As staple legs 14, 16 are bending forward, prongs 26 are drawn back inward, grabbing onto the tissue in the spread between the prongs. As prongs 26 move inward, end segments 20, 22 traverse an arc through the tissue, drawing the tissue into the closing staple.

Figure 35:
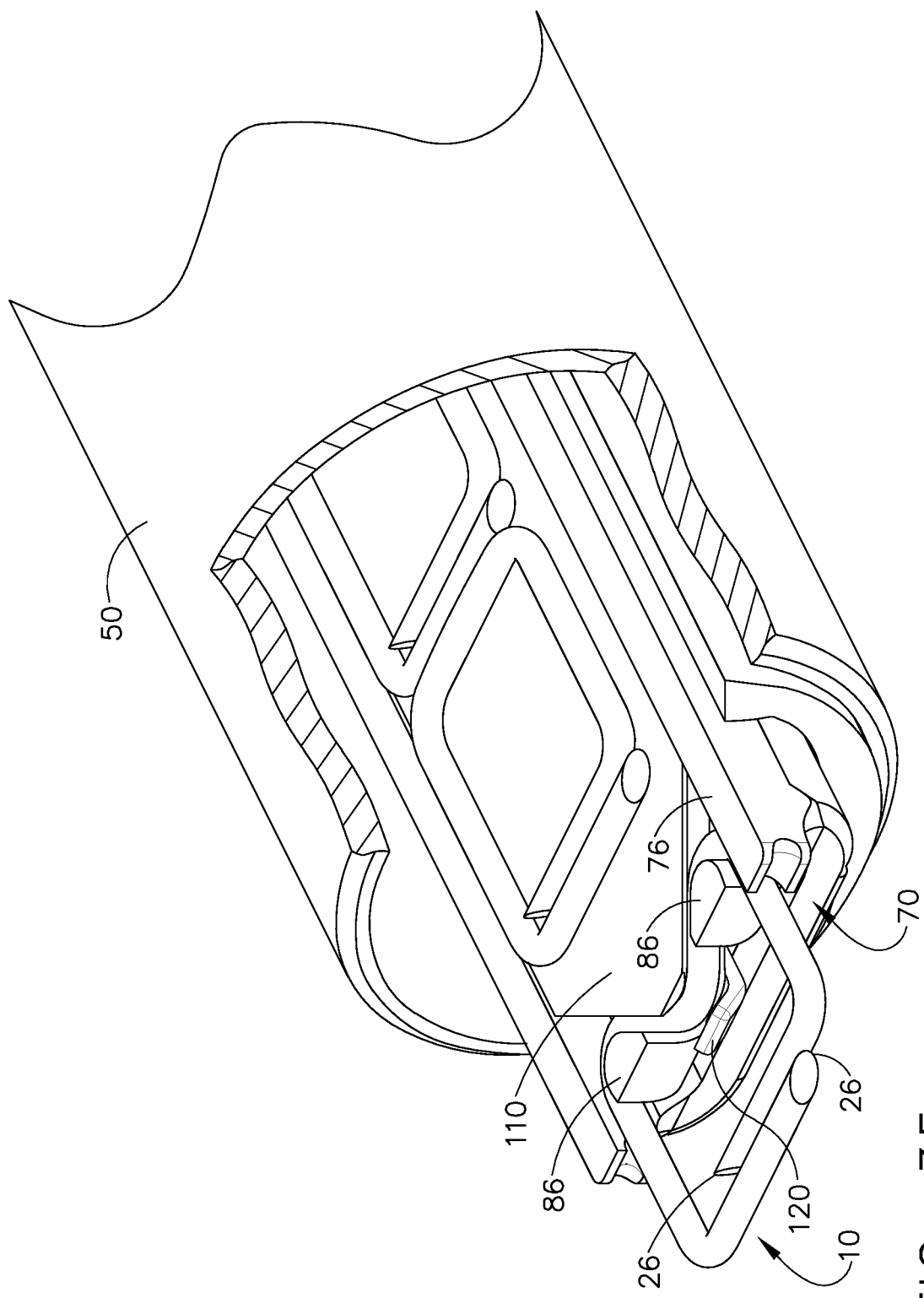
FIG. 35 is an isometric view of the distal end of the stapler, similar to FIG. 30, showing a closed, formed staple held outside the open stapler end by the anvils and spreader.
Figure 36:
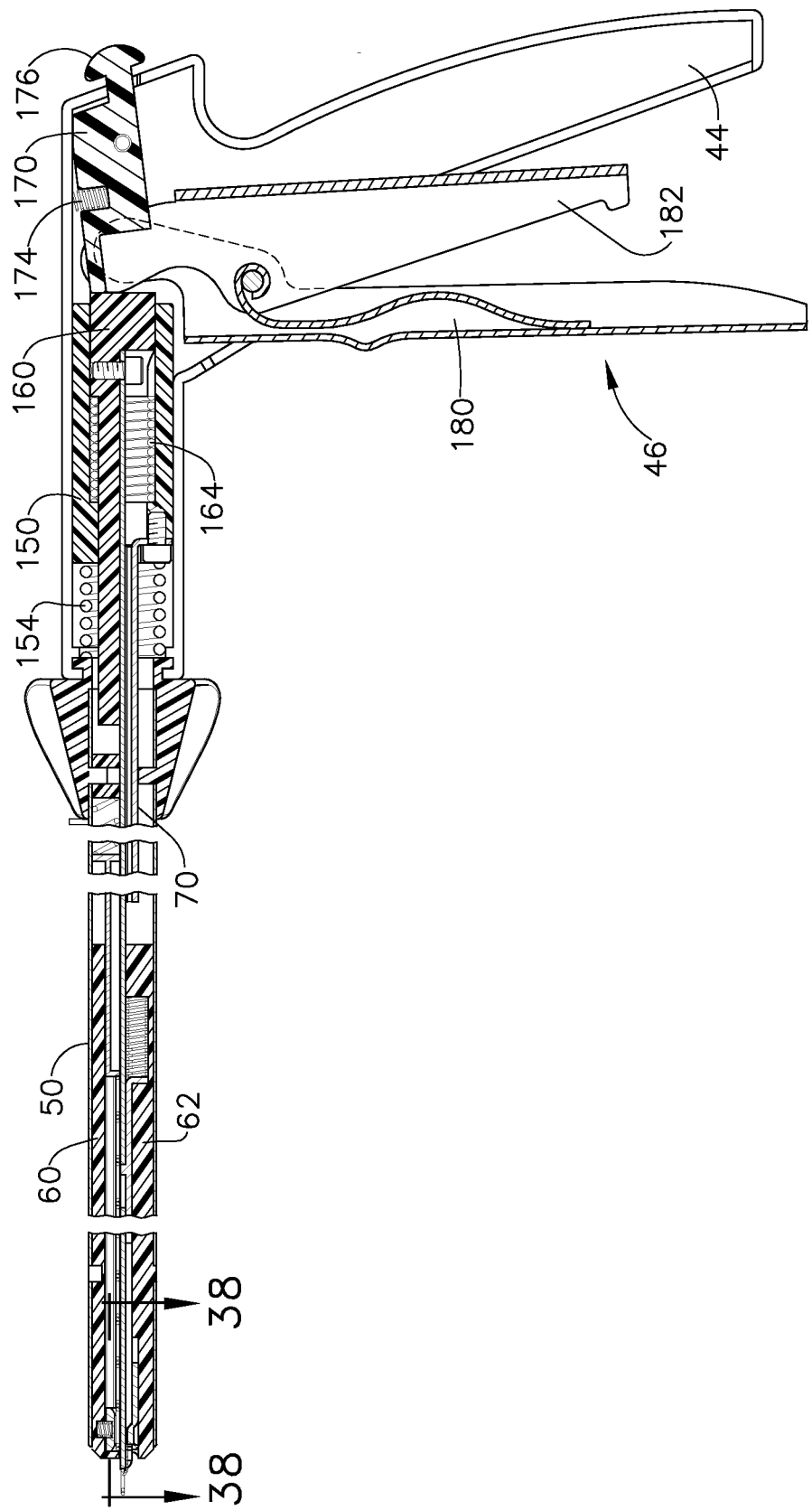
FIG. 36 is a side sectional view of the stapler, similar to FIG. 31, showing the stapler just prior to release of the formed staple.
Figure 37:
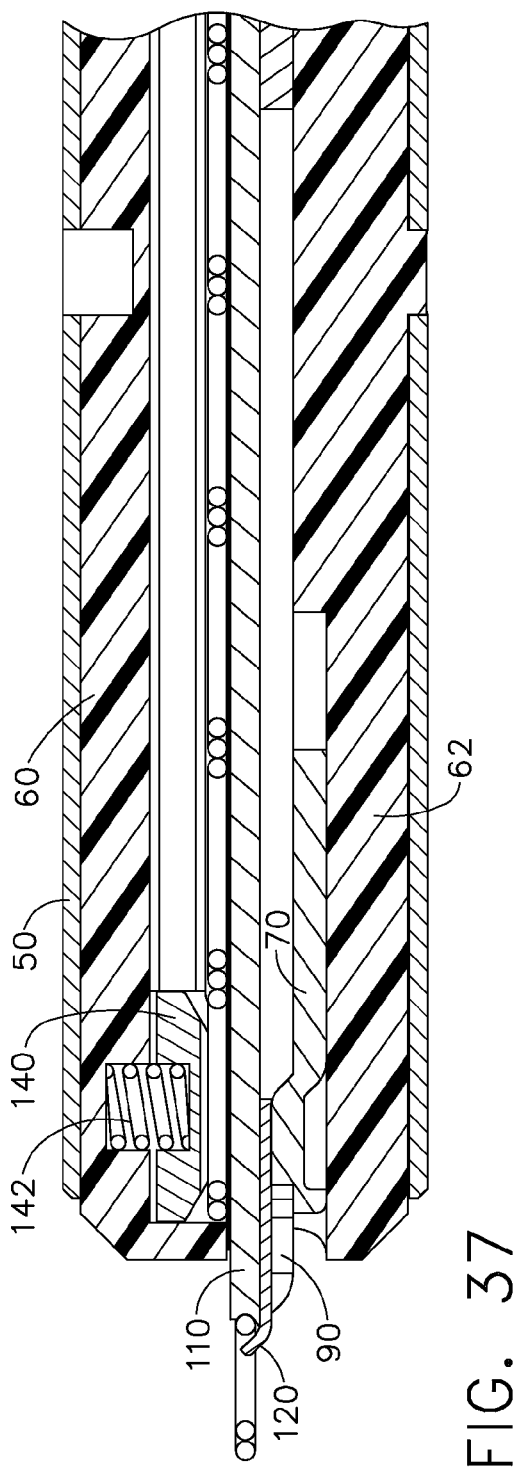
FIG. 37 is a side sectional view of the distal end of the stapler, showing the former retracted and the formed staple ready for release from the stapler.
Figure 38:
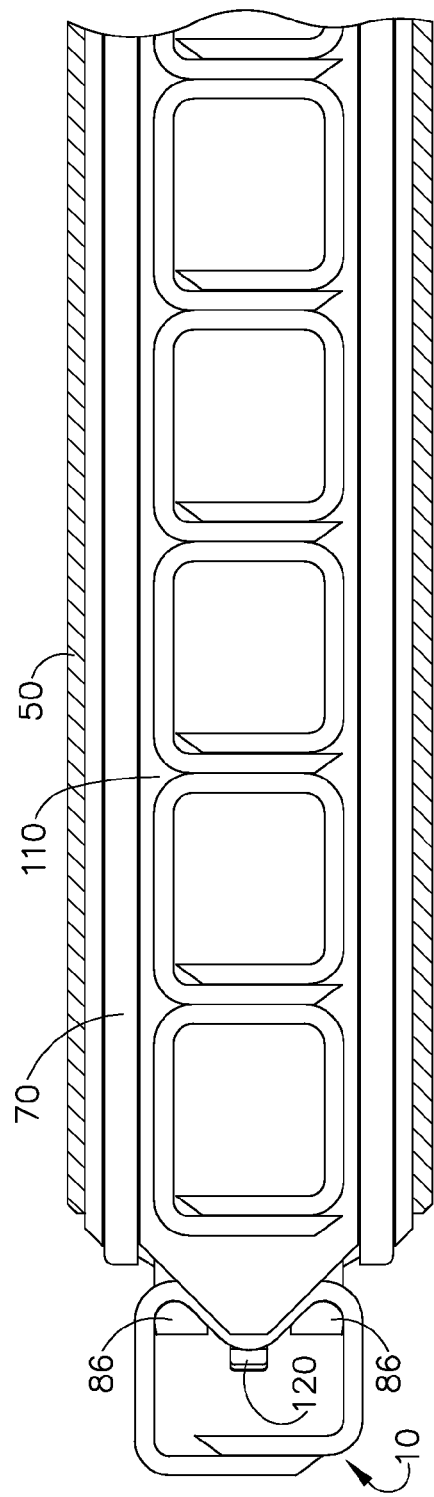
FIG. 38 is a distal end sectional view taken along line 38-38 of FIG. 36.
Figure 39:
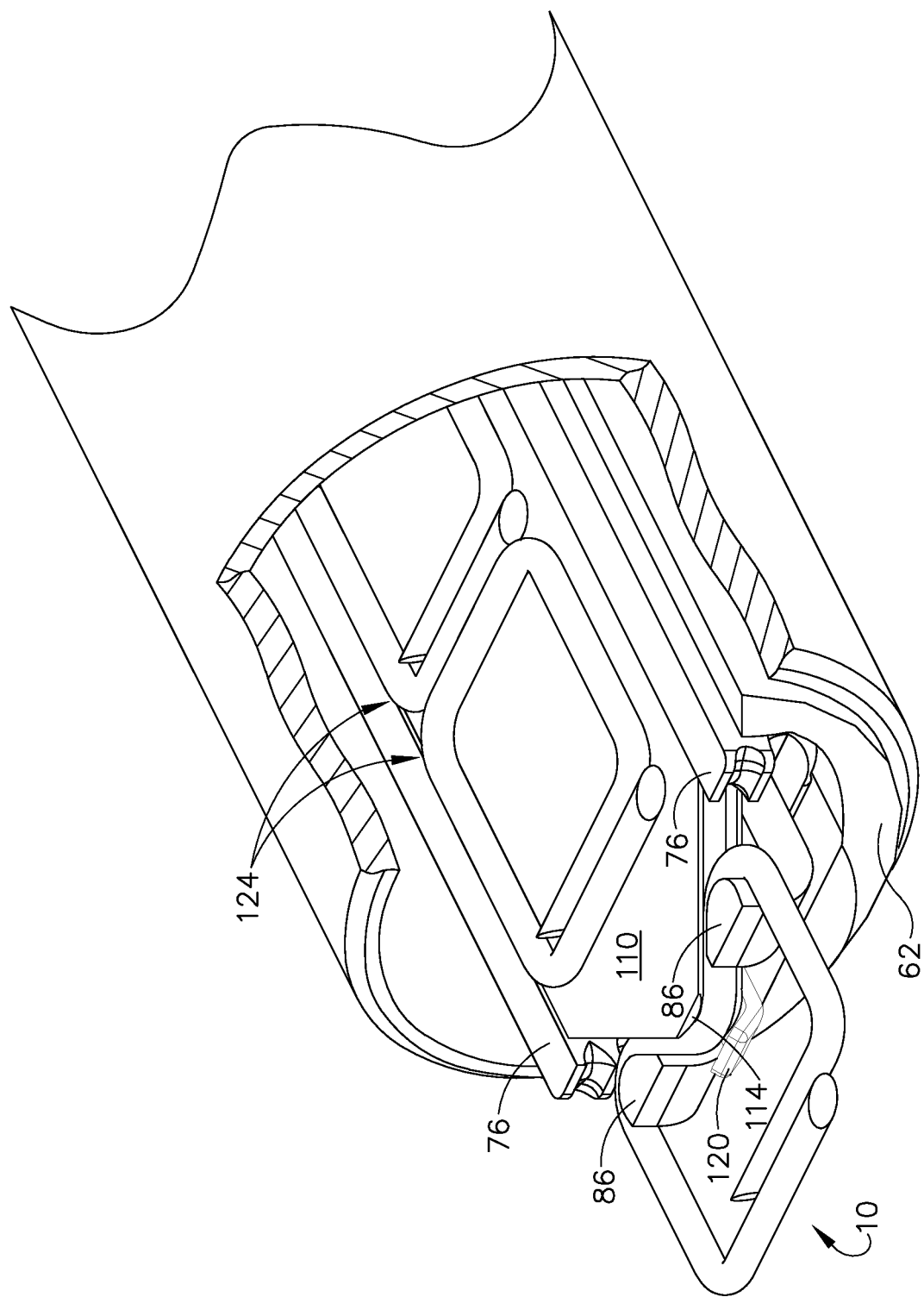
FIG. 39 is an isometric view of the distal end of the stapler, similar to FIG. 35, showing the stapler in a pre-release position, with the former retracted back from the closed, formed staple held outside the open stapler end.

It will be appreciated that the points at which staple legs 14, 16 bend in response to the force of former 70 are spaced laterally outward of the prior bending points for expanding the staple, resulting in additional work hardening along the back span of the formed staple. The additional work hardening increases the strength of the formed staple. The distance between the inner surfaces of former sidewalls 76 is slightly less than the combined width of the expanded anvil arms 84 and staple legs 14, 16, to produce an interference fit between the former sidewalls and staple legs as the former passes along the outside edges of the staple legs. The interference fit between former sidewalls 76 and staple legs 14, 16 initially causes an inward overbending of the staple, as indicated by the phantom lines in FIG. 33. The overbending of the staple during formation will typically be less than 10°, but is dependent on the materials characteristics of the staple. As former 70 retracts following staple formation, the staple springs back to a closed, substantially rectangular configuration in which the staple legs are again substantially parallel. The interference fit between the former and staple legs thus "stretches" staple 10 as the stapler is being closed, to produce a substantially rectangular, finished shape. In the finished, closed shape, the width of the staple is greater than the previous, undeployed width, due to the different bending points along the staple length. This change in staple width enables the staple to have a low profile during delivery and a larger profile when formed through tissue. As prongs 26 reach an inward, preferably overlapping position, in which the staple passes through the gripped tissue, staple former 70 reaches its distal-most position, at which the former bottoms out against the proximal end of base guide 62. At this point, shown in FIGS. 34 and 35, staple 10 is fully formed through the tissue (not shown), and further squeezing of the trigger assembly is prevented.

In metal forming, there are numerous methods to create a 90° bend in a piece of sheet metal. Examples and benefits are described in "Forming a 90 deg. Bend," *MetalForming Magazine*, August 1991, pp. 59-60, and "Fractures in Metal Stampings," *MetalForming Magazine*, November 1996, pp. 84-85, which are hereby incorporated herein by reference in their entirety. Techniques from this field may be applied in a novel way in the field of staple formation. In an alternative embodiment, former 70 contains indentations 95 with a setting radius 97 as shown in FIG. 12B. The primary function and motions of former 70 depicted in FIG. 12B are similar to that of the former depicted in 12A with one notable exception. As former 70 advances distally bending staple 10 into its final configuration created for fastening, setting radii 97 impact staple 10 plastically deforming the outer edges of the intersection between base 12 and staple legs 14, 16. This deformation relieves tension in the outer portion of the staple material in these regions and helps reduce or eliminates the need for overbending helping to eliminate micro fractures that may occur. A general relation for the radius (S) of setting radius 97 is: $S=1.4(WD)+(BR)$ where (WD) is the wire diameter shown in FIG. 6 and (BR) is the inside bend radius of the staple which is defined by the anvil geometry.

Following formation of staple 10, the squeezing pressure on primary trigger 180 is released. As primary trigger 180 is released, former bushing spring 154 propels former bushing 150 and the primary trigger lobes proximally within handle 42. As former bushing 150 moves proximally, compressing spreader spring 164 between the bushing and spreader driver 160, the bushing draws former 70 away from the formed staple, as shown in FIGS. 36-39. As former 70 retracts, anvil stop 92 moves back from between anvil bosses 90. After the actuator assembly is released, and former 70 retracted, locking member 170 can be reset via button 176 to eject the formed staple from the stapler.

As button 176 is pressed down, the tip of locking member 170 disengages from the proximal end of spreader driver 160, allowing the driver to retract proximally under the force of spreader spring 164. The retracting driver 160 pushes against the upper lobes of secondary trigger 182, resetting the trigger. As spreader driver 160 moves proximally, the driver also retracts spreader 110 from the formed staple. Spreader 110 retracts just ahead of anvil base 82, due to the proximal position of anvil peg 102 within spreader slot 122. As spreader 110 retracts, spreader apex 114 moves out from between anvils 86, enabling anvil arms 84 to pull back inward, disengaging the anvils from the inside edges of the formed staple. As spreader 110 retreats from the inwardly retracting anvils, spreader hook 120 flips the back span of the formed staple from the anvils, thereby ejecting the staple from the stapler. The retracting differential between the spreader 110 and anvil base 82 enables the spreader hook 120 to release and eject the formed staple prior to the proximal movement of the anvil base. After the staple is ejected, as spreader 110 continues to retract from beneath shoe 140, load spring 142 pushes the distal-most staple in stack 124 down onto the now narrowed anvils 86. As anvil peg 102 is released within spreader slot 122 by the moving spreader 110, anvil base 82 springs back in conjunction with the spreader to its initial deployment position (shown in FIGS. 20 and 21), in which anvil peg 102 is reset at the distal end of the spreader. With the actuator assembly 46, spreader 110, former 70 and anvil base 82 reset to their initial deployment positions, and a new staple staged on the anvils 86, stapler 40 is ready to be re-fired to deploy the next staple.

Figure 40:
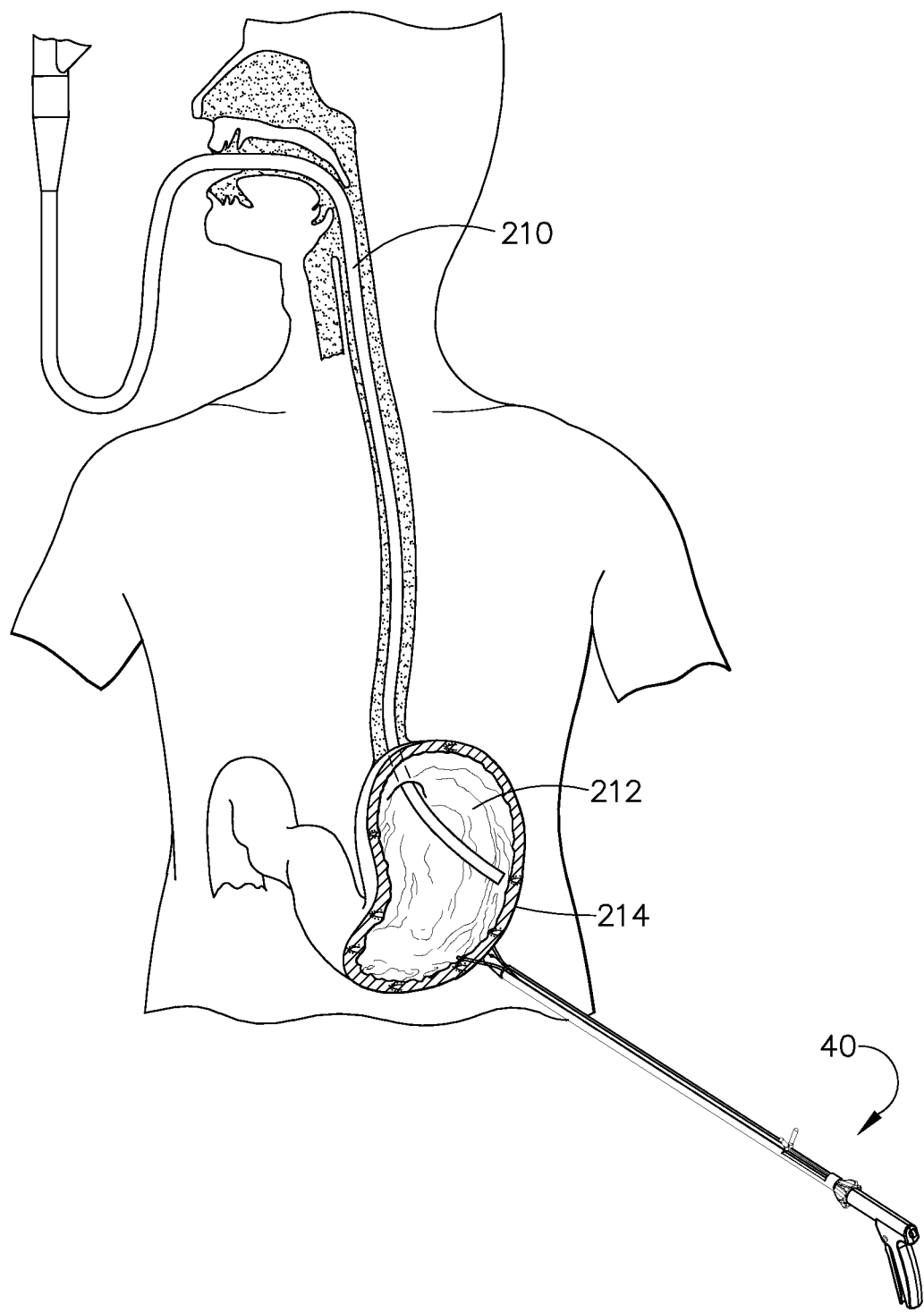
FIG. 40 is a schematic view of a patient during a hybrid endoscopic-laparoscopic procedure.

As mentioned above, one of the many applications for stapler 40 is in a gastric volume reduction (GVR) procedure. FIG. 40 is a diagrammatic view of a patient during a GVR procedure, in which a fold is formed in the wall of the gastric cavity. During the GVR procedure, a flexible endoscope 210 may be passed transesophageally into the interior of the gastric cavity 212 to provide insufflation, illumination, and/or visualization of the cavity. Gastric cavity 212 can be insufflated through endoscope 210 to create a more rigid working surface. Insufflation of the gastric cavity also allows the boundaries of the cavity and the desired location for a fold to be mapped out by external palpation of the abdomen. Alternatively, the GVR procedure can be performed solely laparoscopically, using a plurality of trocar ports inserted into the abdominal wall to provide access to the peritoneal cavity. Alternatively, a bougie may be introduced into the gastric cavity to ensure there is no obstruction of the lumen at the completion of the procedure.

Figure 41A:
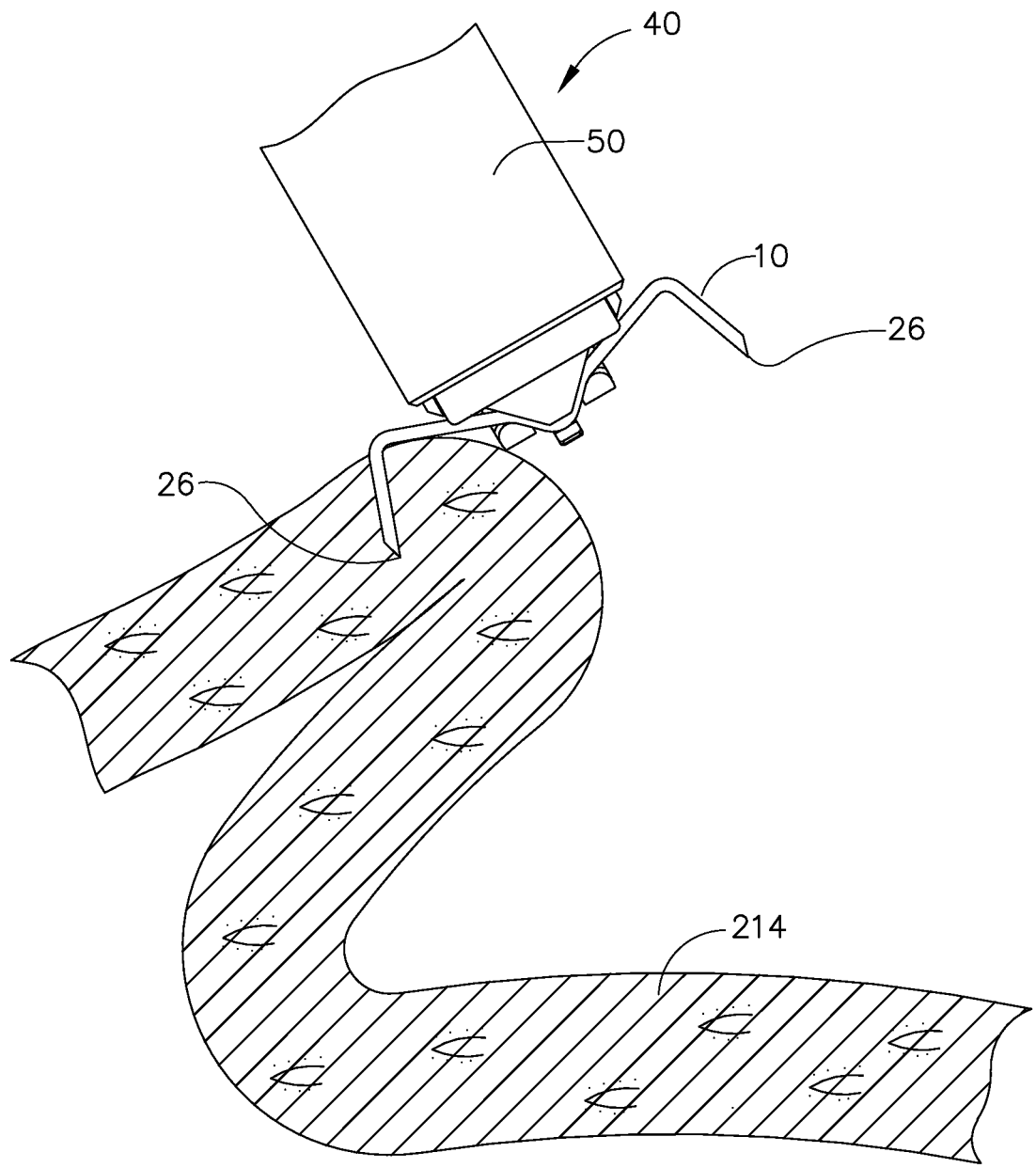
FIG. 41A is a schematic view of a cavity wall section being grabbed by a stapler prong.
Figure 41B:
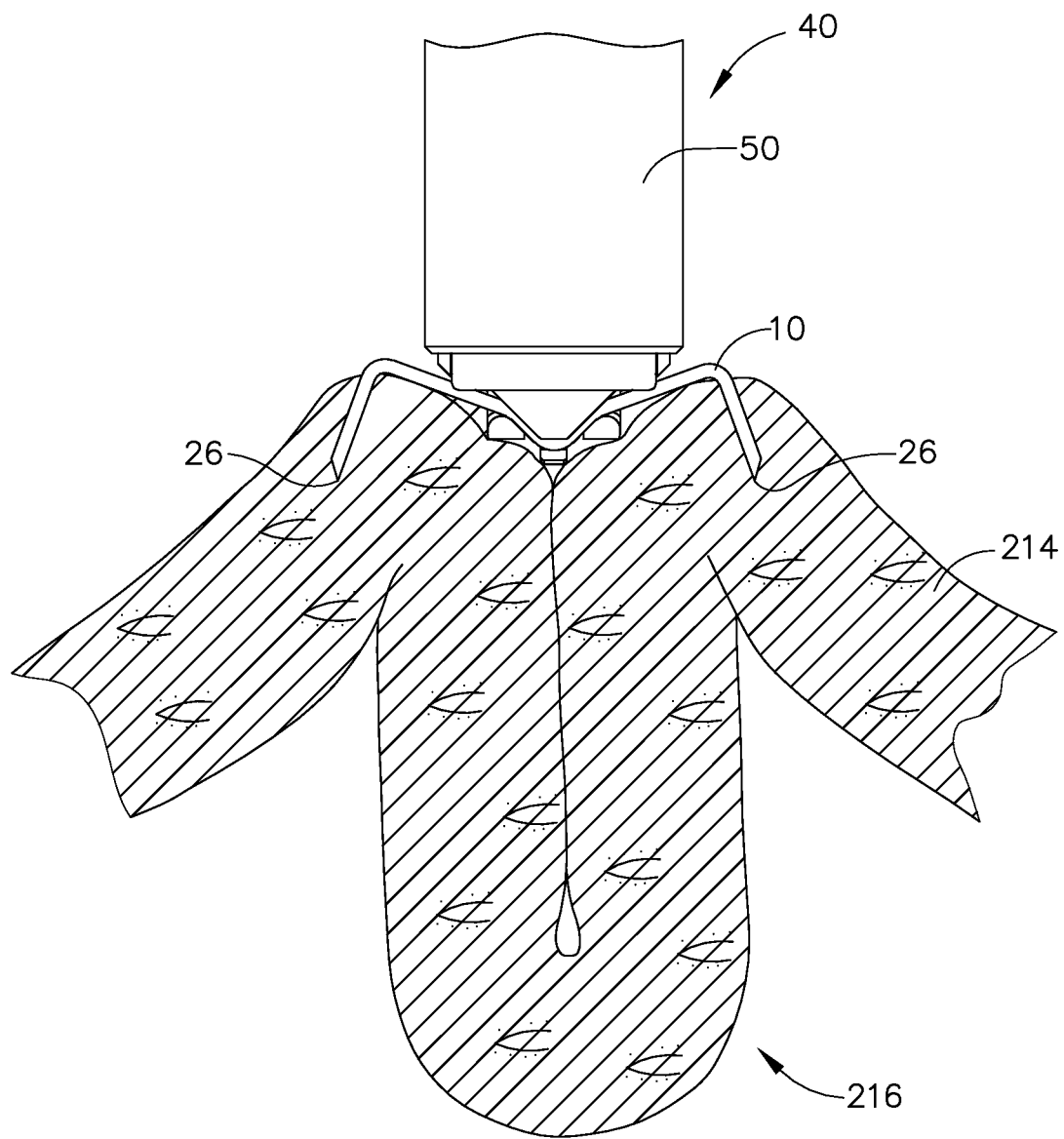
FIG. 41B is a schematic view similar to FIG. 41A showing the cavity wall section drawn together into a fold by the stapler prongs.
Figure 42:
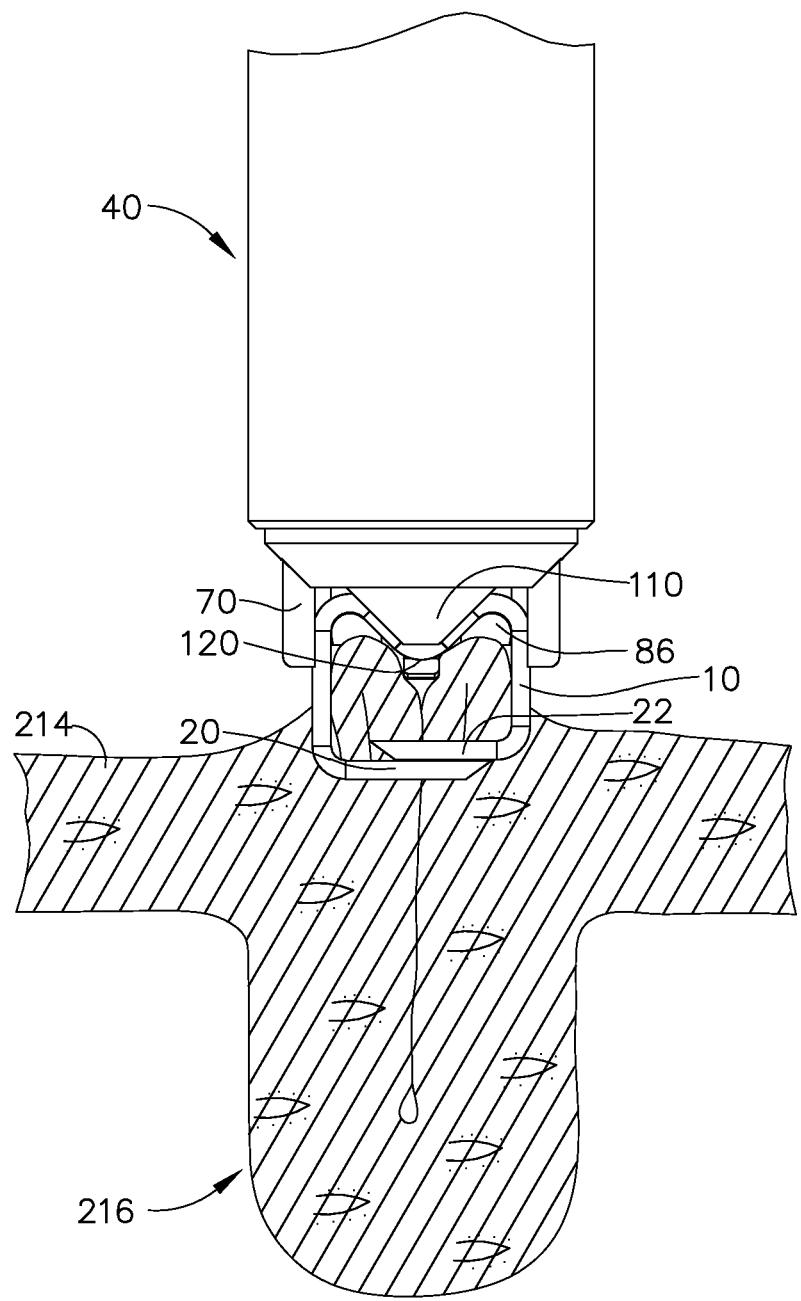
FIG. 42 is a schematic view of a staple being formed through an approximated section of the cavity wall.

To perform the GVR procedure, a trocar port is inserted through an incision in the abdominal wall. Stapler 40 of the present invention is passed through the trocar and into the peritoneal cavity. In addition to stapler 40, other instruments including, for example, cameras and retractors (not shown), may be inserted through the abdominal wall or other access means (e.g., transgastric, transvaginal, etc.) as necessary to facilitate the GVR procedure. Multiple trocars may be used to accomplish this aim; however, in an alternative embodiment a single trocar with multiple ports may be placed to facilitate this procedure. In a preferred embodiment, the single trocar with multiple ports is place in the vicinity of the umbilicus of the patient. With stapler 40 inside the cavity, pressure is applied to actuator assembly 46 to advance a staple 10 outside the open end of the stapler. Staple legs 14, 16 are expanded open outside the stapler, so that prongs 26 face forward towards the cavity wall. With staple legs 14, 16 open, stapler 40 can be manipulated to grab sections of the cavity wall 214 with prongs 26 as shown in FIG. 41A. As stated above, prongs 26 may have features facilitating secure grasping of tissue. As the staple prongs grab onto separate wall sections, the sections are drawn together, as shown in FIG. 41B, to appose the serosal tissue between the staple legs. As the sections are drawn together, the tissue involutes inward into cavity 212 forming a fold 216. With the tissue sections folded and held by prongs 26, additional pressure can be applied to actuator assembly 46 to form the staple 10 through the tissue. As staple 10 is being closed by former 70, as shown in FIG. 42, prongs 26 and staple end segments 20, 22 draw together within the cavity wall to secure the tissue sections together. After the staple 10 is formed through the tissue to hold fold 216 in place, actuator assembly 46 is released to eject the staple from the stapler. Although FIG. 42 depicts staple 10 as only partially penetrating the gastric wall, it will be recognized that the staple could also penetrate the entire wall thickness of the gastric cavity. In an alternative embodiment, treatments to promote healing (e.g., tissue abrasion, sclerosants, etc.) may be applied to the surface (e.g., serosal surface of the stomach, etc.) to be infolded that promote beneficial outcomes (e.g., healing of apposed surfaces, integration of a tissue surface to prosthetic surface, reduced short term edema in the fold, etc.) as well as tissue treatment in the vicinity of the staple (i.e. injecting polymethylmethacrelate commonly known as PMMA, etc.) to increase the strength of the tissue local to the fastener.

After the first staple is deployed, stapler 40 is preferably moved to a second location on the cavity wall along the intended fold line. Additional staples are preferably deployed along the cavity wall to extend the length of the fold. The trocars may be flexed within the abdominal wall, or removed and repositioned within the abdominal wall as necessary, in order to reach all of the desired staple locations. The number of staples used to form a fold will depend upon the desired length for the fold, and the desired spacing between the staples. Preferably, staples 10 are evenly spaced apart along the length of the fold line. Likewise, staple legs 14, 16 are preferably evenly spaced apart across the fold line, so that a uniform tissue fold is formed without distortion or bunching. Housing 50 may be rotated (or flexed) as needed in order to align the staple prongs on opposite sides of the tissue fold. The proper relative spacing of the staples can be ascertained through laparoscopic visualization. After an initial row of staples has been deployed along the length of the fold line 216, a second row of staples can be deployed about the first row in order to increase the depth of the fold. In a preferred embodiment, stapler 40 may be used to form a large fold apposing the greater curvature of the stomach to the lesser curvature thereby completely infolding the anterior surface of the stomach. In an alternative embodiment, the greater curvature of the stomach is freed from its attachments (e.g., short gastric arteries, omentum, etc.) and is infolded by apposing the anterior and posterior walls about the greater curvature of the gastric cavity. However, combinations of these procedures and other alternative locations can also be chosen for the cavity wall fold depending upon the particular objectives of the procedure and the desired impact on satiety and/or satiation.

Figure 43:
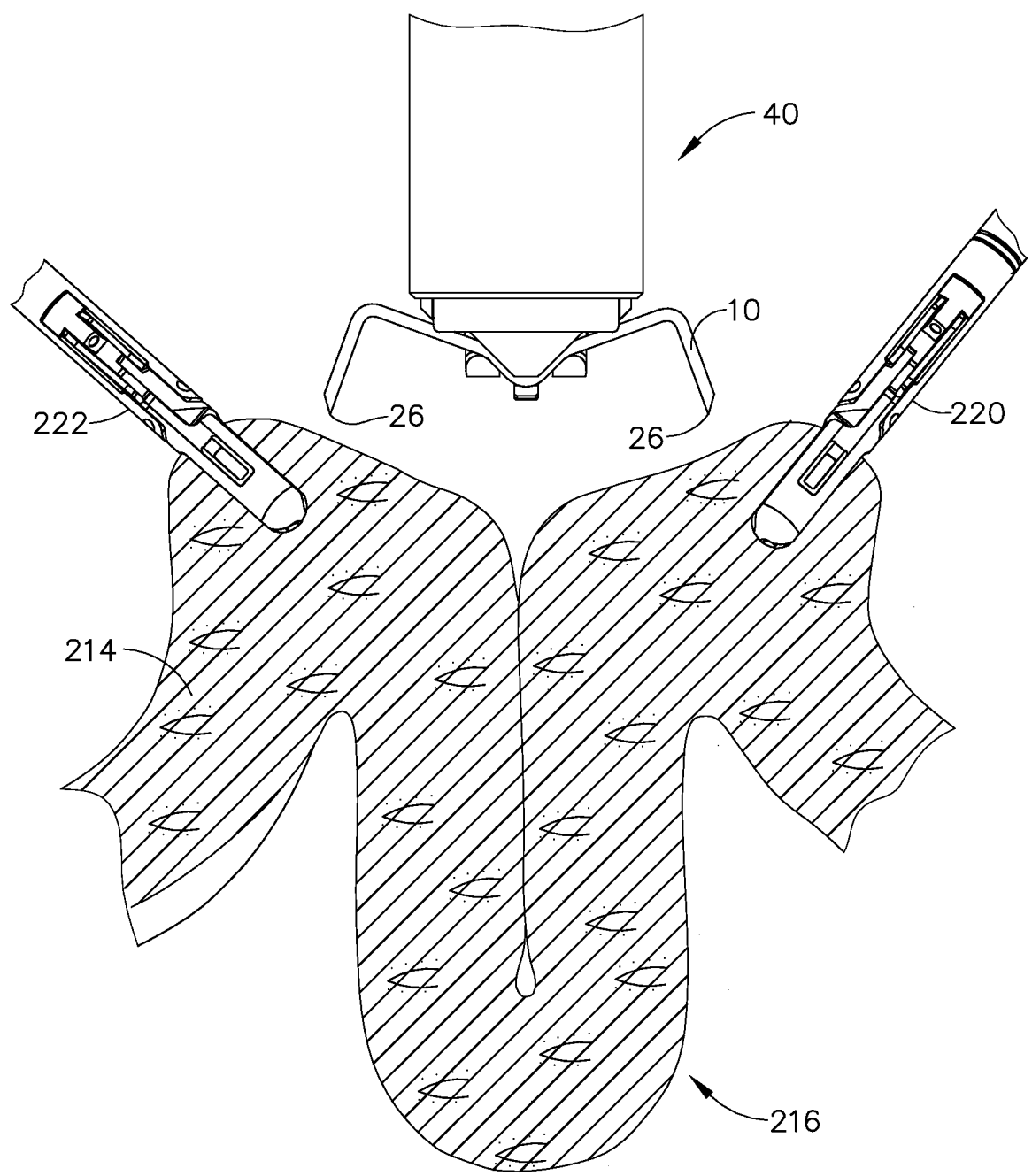
FIG. 43 is a schematic view of a cavity wall section being approximated by a set of graspers prior to deployment of a staple into the apposed tissue sections.

In an alternative scenario, shown in FIG. 43, tissue graspers 220, 222 may be inserted into the peritoneal cavity and used to draw spaced sections of the cavity wall 214 together to form a fold 216. With graspers 220, 222 holding the two tissue sections together, the distal end of stapler 40 is pressed against the approximated tissue to bridge the crease between the sections. Laparoscopic visualization may be used to determine the correct stapler location along the tissue crease. After the proper insertion location is determined, actuator assembly 46 is depressed to expose and expand a staple 10 outside of the stapler as shown. With staple 10 exposed, the cavity wall 214 is punctured on opposite sides of the fold 216 by prong tips 26. Primary trigger 180 is then depressed further to close and form staple 10 through the tissue held between the prongs.

After the first staple is deployed, graspers 220, 222 are moved to a second location on the cavity wall along the intended fold line. At this second location, the graspers are again used to draw different sections of tissue together to involute the tissue into cavity 212. With graspers 220, 222 holding the tissue sections together, stapler 40 is again placed across the crease between the sections, and assembly 46 actuated to expose and expand staple 10 outside the open distal end of the stapler. After staple prongs 26 are inserted on opposite sides of the tissue fold, additional pressure is applied to the actuator assembly to close and form the staple through the tissue. As in the previous example, additional staples may be deployed along the cavity wall to extend the fold to the desired length. The trocars may be flexed within the abdominal wall, or removed and repositioned within the abdominal wall as necessary, in order to reach all of the desired staple locations. After an initial row of staples has been deployed along the length of the fold line, a second row of staples can be deployed above the first row in order to increase the depth of the fold. Additional details regarding the GVR procedure are described in co-pending U.S. patent application Ser. Nos. 11/779,314 and 11/779,322, which have been previously incorporated herein by reference in their entirety.

Figure 44:
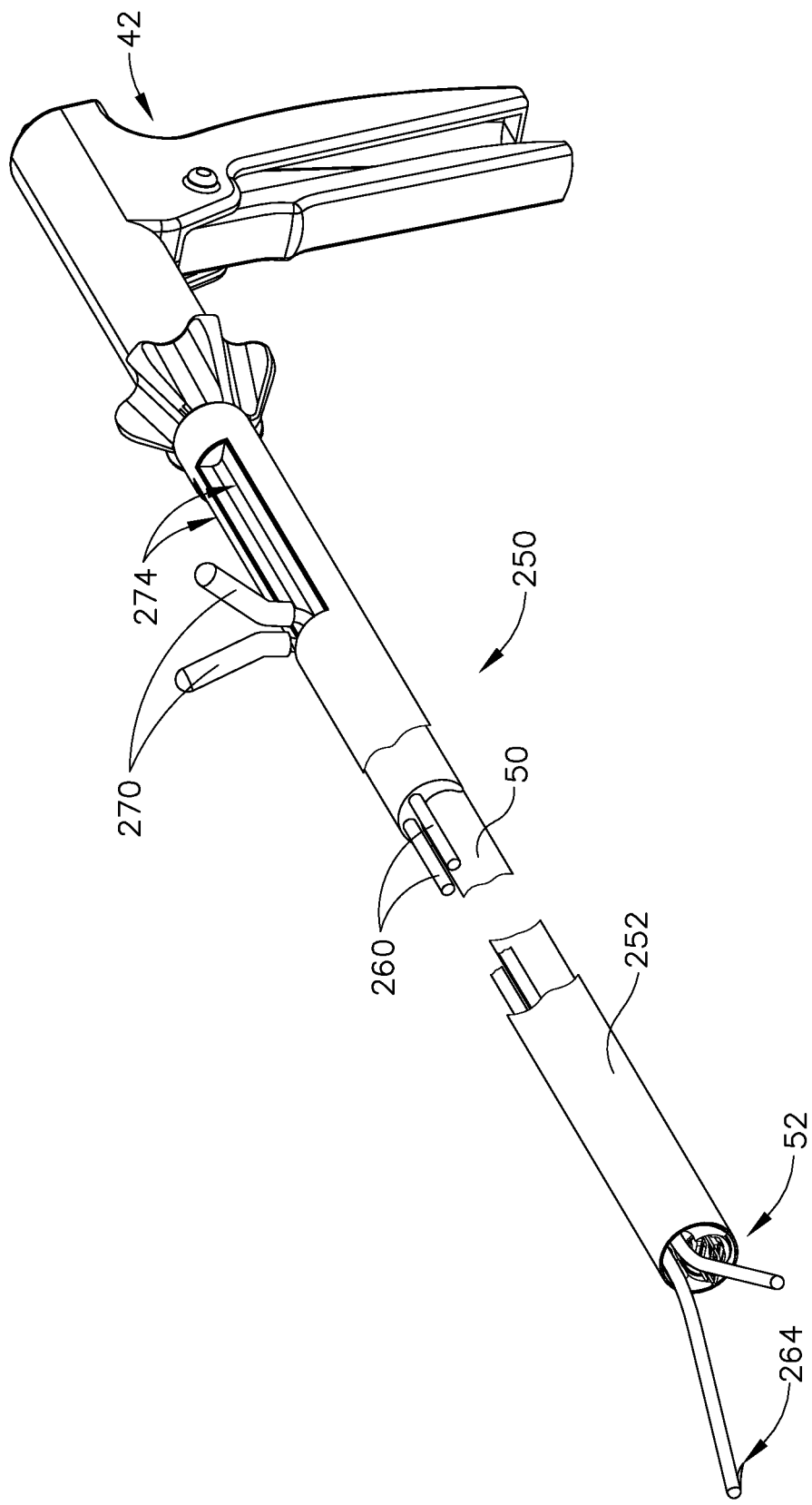
FIG. 44 is an isometric view of the stapler inserted into a tissue grasping device.

FIG. 44 depicts an exemplary tissue grasping device 250 which can be added on to stapler 40 to combine the stapler and tissue grasping members into a single instrument. Combining tissue graspers with the stapler 40 in a single instrument can reduce the number of required trocars, as well as the need to adjust and control separate instruments during a procedure. In the embodiment shown in FIG. 44, the tissue grasping device 250 comprises a cylindrical sleeve 252 having a longitudinally extending bore that is open at both sleeve ends. The sleeve bore is sized to accommodate fastener housing 50, so that the housing can be slid through the sleeve from the proximal to distal ends. When fully inserted into sleeve 252, the open distal end of stapler 40 protrudes just beyond the distal sleeve opening. Sleeve 252 also includes longitudinal openings for reciprocally retaining tissue grasping wires. In the embodiment shown in FIG. 44, a pair of grasping wires 260 is retained within sleeve 252. Grasping wires 260 extend longitudinally through sleeve 252, with the distal ends of the wires projecting outside the sleeve opening. A tissue hook 264 is provided on the distal end of each wire 260 for gripping and holding tissue. Preferably, hooks 264 extend at a proximal angle from the underside of wires 260 to aid in drawing the gripped tissue towards the open stapler end. A pull lever 270 is connected to the proximal end of each wire 260 for manipulating the position of the wire. A slot 274 is formed in the outer periphery of sleeve 252 for each of the wires 260. Levers 270 project from wires 260 through slots 274 to enable the wires to be easily manipulated through the sleeve.

Figure 45:
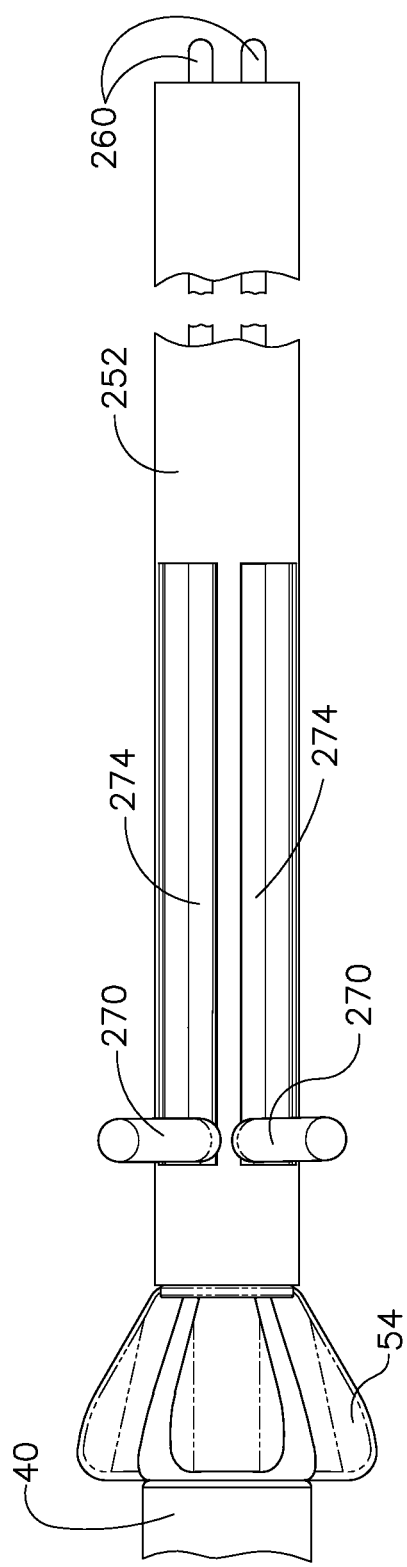
FIG. 45 is a top view of the distal end of the tissue grasping device and stapler, showing the grasping wires in a proximal position.
Figure 46:
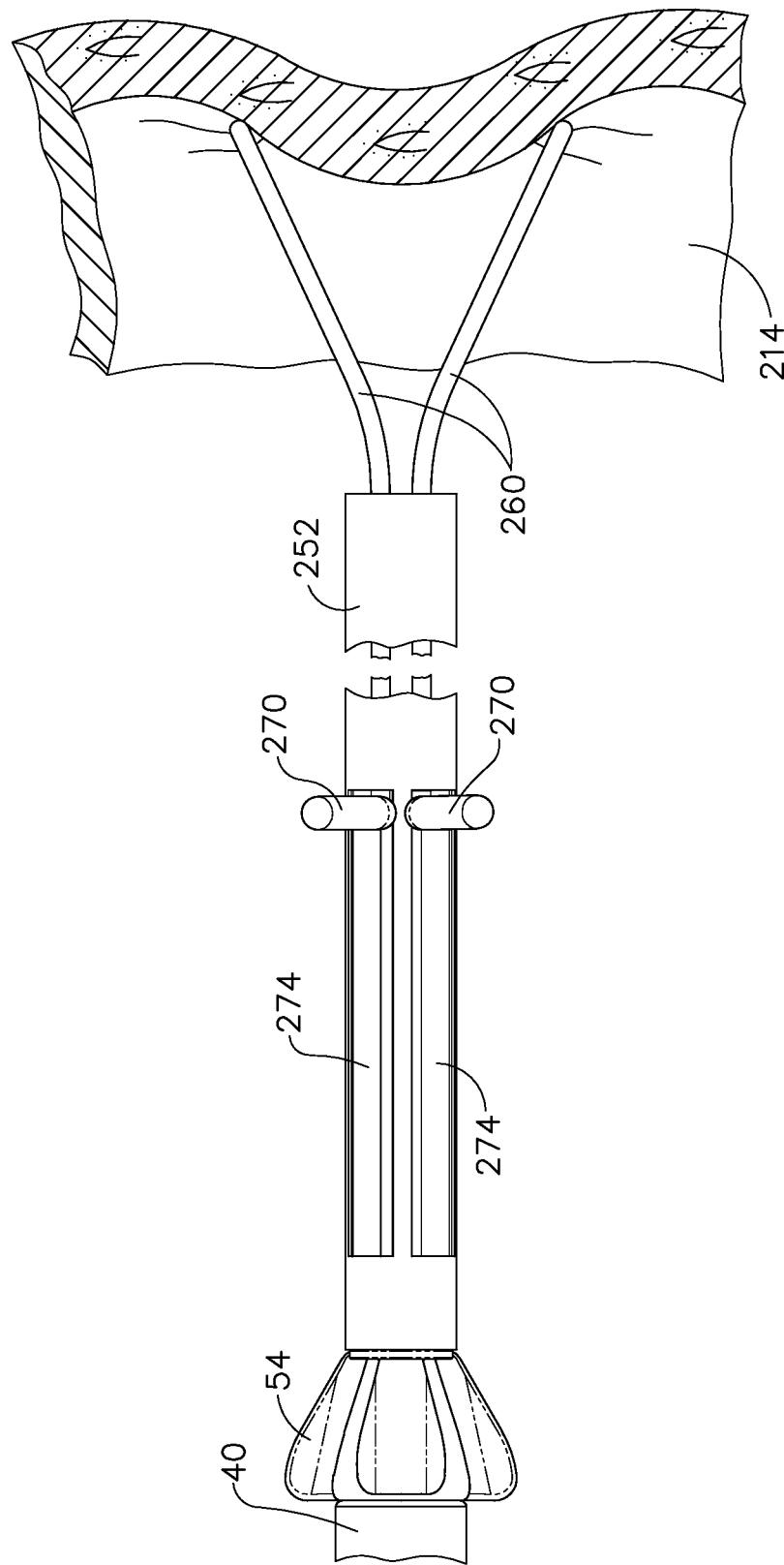
FIG. 46 is a top view of the distal end of the tissue grasping device and stapler, showing the grasping wires in a distal position.

Using levers 270, wires 260 can be individually drawn back and forth within slots 274 to advance or retract the distal wire ends. In addition to longitudinal reciprocation, levers 270 can be rotated up to 90° within slots 274 in order to rotate the distal tips of wires 260. It will be appreciated by one skilled in the art that a wider range of rotation is possible however. Levers 270 can be individually pivoted in different directions, from a substantially center, 12 o'clock position, to lateral positions at 3 o'clock and 9 o'clock. When levers 270 are in a proximal position, as shown in FIG. 45, grasping hooks 264 are drawn back adjacent the open end of sleeve 252. As levers 270 slide distally through slots 274, as shown in FIG. 46, the hooked tips of wires 260 advance out the distal end of the device.

Figure 47:
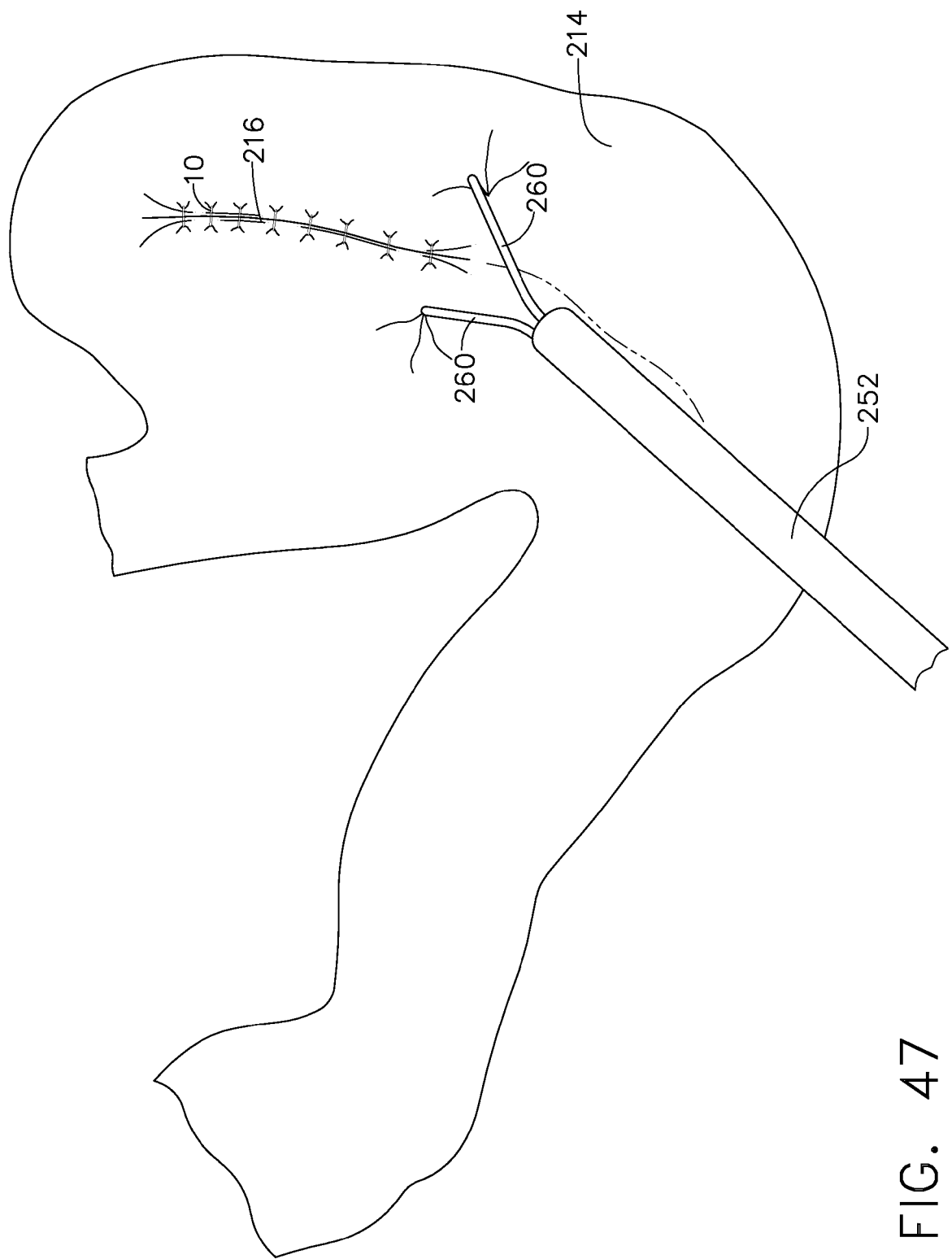
FIG. 47 is a diagrammatic view showing a pair of tissue grasping wires gripping onto spaced sections of a gastric cavity wall.
Figure 48:
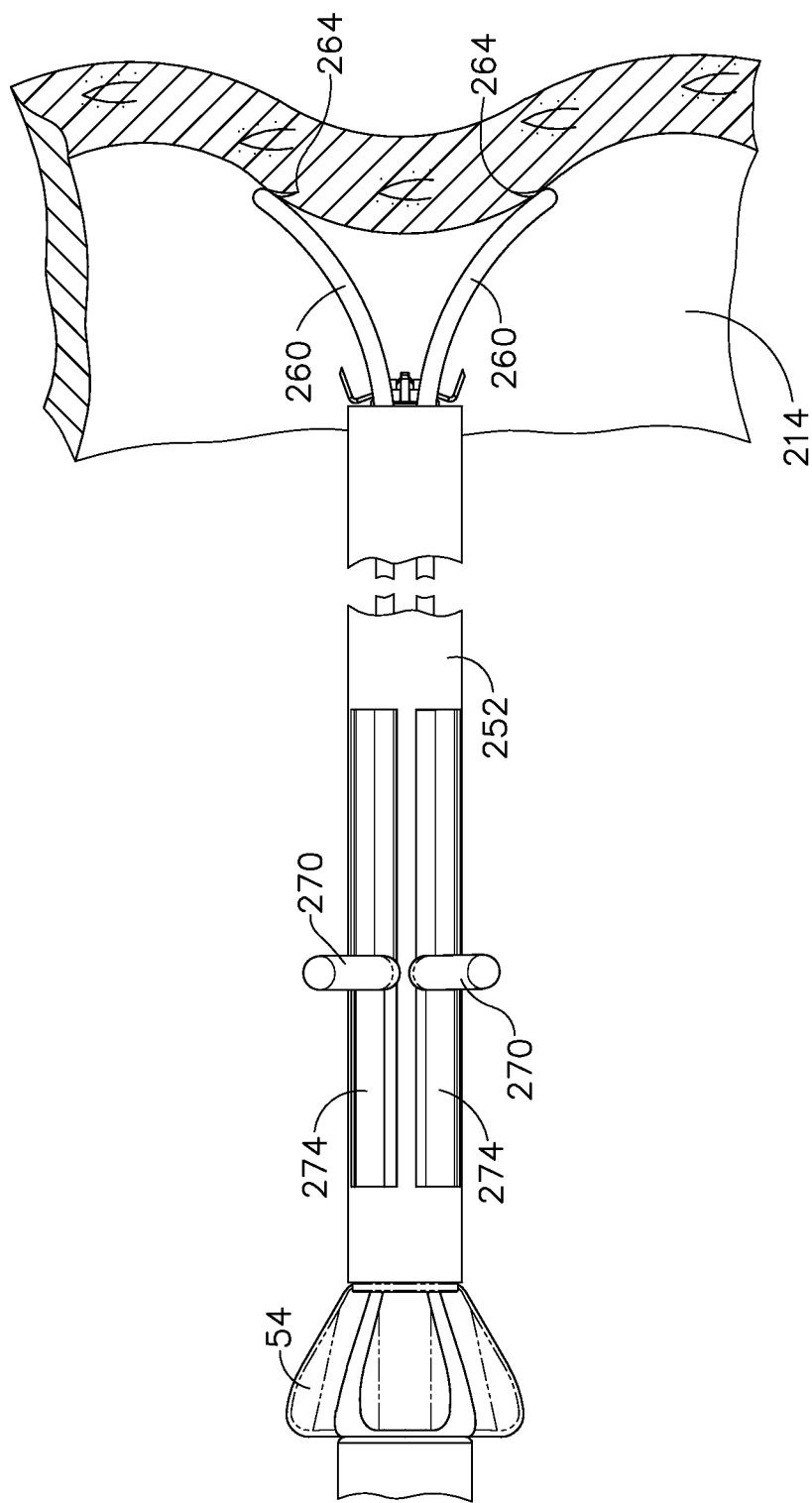
FIG. 48 is a top view of the distal end of the tissue grasping device and stapler, showing the grasping wires being retracted into the device to pull the gripped tissue sections together.
Figure 49:
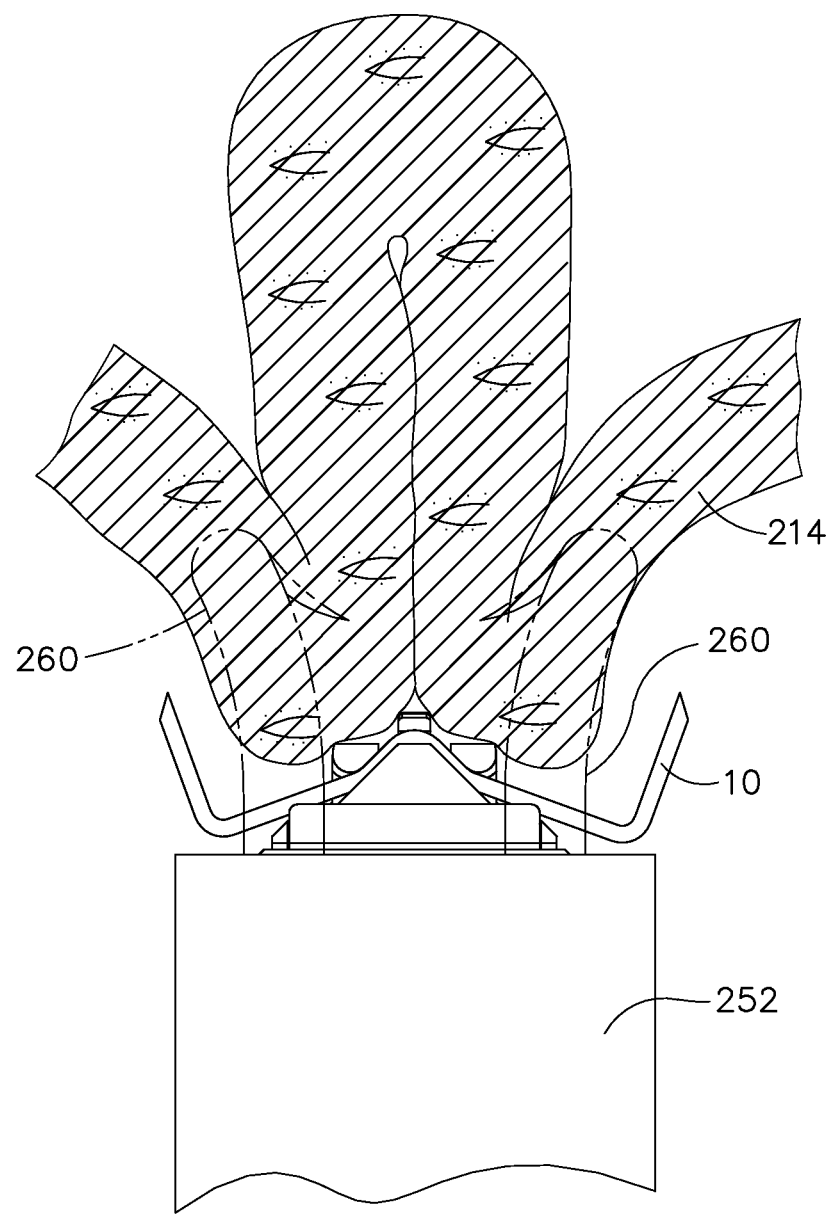
FIG. 49 is a top view of the distal end of the tissue grasping device and stapler, showing the grasping wires retracted to pull the gripped tissue sections against the open distal end of the stapler.

Wires 260 are preferably elastic material stainless steel with a prebent shape which enables the wires to expand apart outside of sleeve 252, yet be retractable back together within the sleeve without taking a permanent set. Material geometry and properties (e.g., yield strength, etc.) Super elastic or shape memory materials such as nitinol may also be used. Wires 260 include a slight outward bend proximal of hooks 264 that produces an outward bias in the wires. The outward bias enables the distal ends of the wires 260 to expand apart as the wires are pushed out of sleeve 252. As wires 260 expand outward, downwardly extending hooks 264 grab onto spaced sections of tissue, such as the cavity wall 214 shown in FIGS. 46-47, as the wires are moved along the surface of the wall. With the tissue sections held by hooks 264, the distal ends of wires 260 can be drawn together to appose the tissue by either rotating the wires downward, retracting the wires back into sleeve 252, or a combination of the two. The distal ends of wires 260 are rotated downward by individually pivoting levers 270 from a center to a side position. As levers 270 pivot downward, the ends of the wires are drawn together. As the ends of wires 260 are brought together, the tissue sections gripped by hooks 264 are also drawn together to create a fold 216 between the sections. In addition to pivoting, levers 270 can be drawn proximally within slots 274, as shown in FIG. 48, to draw the gripped tissue sections into a fold against the open end of stapler 40. Once the folded tissue has been pulled by wires 260 against the distal end of stapler 40, as shown in FIG. 49, actuator assembly 46 is squeezed to advance a staple 10 towards the tissue. With the staple advanced out the open end of stapler 40, the staple placement can be adjusted relative to the crease between the tissue sections. Once the correct staple placement is obtained, trigger 180 is fully actuated to form the staple through the tissue.

After the staple 10 is formed through the tissue, the staple is ejected from stapler 40 by first releasing actuator assembly 46 and then locking member 170. After the staple is ejected, device 250 can be moved to a new location and grasping wires 260 again advanced out from the device to grab additional sections of tissue. These additional sections of tissue can be stapled together to increase the length and depth of the fold, as described above.

Figure 50:
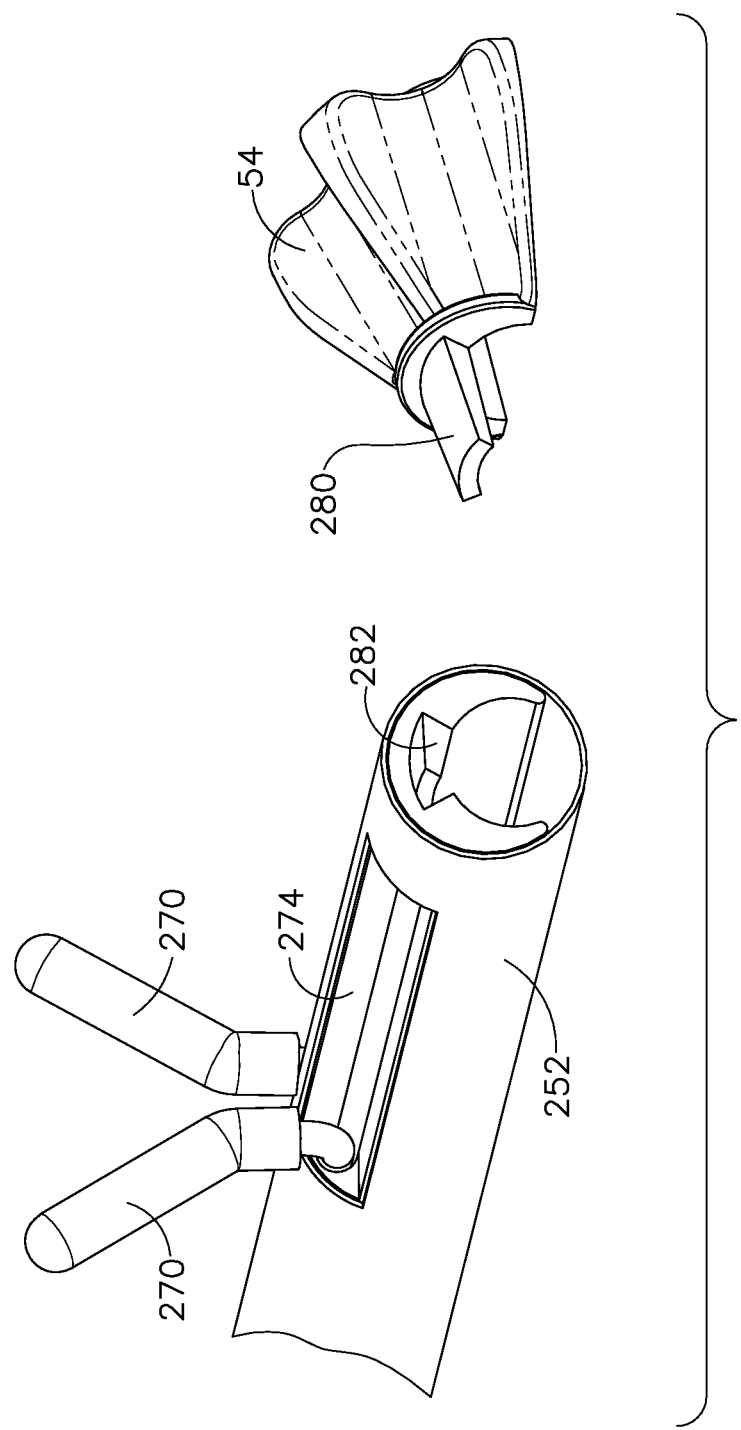
FIG. 50 is an isometric view showing an exemplary connection for the stapler and tissue grasping device.

FIG. 50 shows an exemplary modification to rotating knob 54 for connecting tissue grasping device 250 to stapler 40. In this modification, a taper lock wedge 280 is provided on the distal end of rotating knob 54. Wedge 280 is insertable into a corresponding notch 282 formed into the proximal end of sleeve 252. Notch 282 and wedge 280 have complementary tapered sides to enable the parts to be slid together. Once connected, the tapered sides of wedge 280 and notch 282 resist separation other than from a proximal pulling force along the longitudinal axis of the stapler. The taper lock connection permits tissue grasping device 250 and stapler 40 to be attached or detached as necessary, yet maintains a secure connection between the two devices during use. In addition to the taper lock shown, alternative types of connectors can also be used for attaching tissue grasping device 250 to stapler 40 without departing from the scope of the invention.

Another application of the surgical stapler of the present invention is the repair of a tissue defect, such as an inguinal hernia, located in inguinal tissue such as the inguinal floor. An inguinal hernia is a condition where a small loop of bowel or intestine protrudes through a weak place or defect within the lower abdominal muscle wall or groin of a patient. With this condition, the patient can be left with an unsightly bulge of intestinal tissue protruding through the defect, pain, reduced lifting abilities, and in some cases, impaction of the bowel, or possibly other complications if the flow of blood is cut off to the protruding tissue. As disclosed in greater detail in commonly assigned U.S. Pat. Nos. 6,572,626, 6,551,333, and 6,447,524, which are hereby incorporated herein by reference in their entirety, an inguinal hernia repair can involve closure of the defect with sutures or fasteners, but generally involves placing a surgical prosthetic, such as a mesh patch, over the open defect and attaching the patch to the inguinal floor. Traditionally, the mesh patch has been attached with suture or surgical fasteners. Stapler 40 of the present invention provides an alternative method for attaching the mesh patch to the inguinal floor. Using stapler 40, the patch can be affixed through a smaller (5 mm) access port than is possible when using suture or traditional types of surgical fasteners.

To tack the patch to the inguinal tissue, the stapler is advanced into the lower abdomen to place the distal stapler end in the area of the hernia defect. The trigger assembly is actuated to advance a staple 10 outside the open end of the stapler, with prongs facing forward, as shown in FIG. 28. With staple 10 exposed outside of stapler 40, the staple can be used to probe the tissue to determine the appropriate tacking point. Probing with the staple prongs prior to tacking down the mesh patch enables the surgeon to better detect ligaments, as opposed to the surrounding bone, so that the staple accurately penetrates the desired tissue and/or ligaments. Once the appropriate location is determined, stapler 40 is manipulated to place prongs 26 through or into openings in the prosthetic mesh. In a preferred embodiment for this application open angle 209 is approximately zero degrees to facilitate piercing of prosthetic tissues. With the staple in the desired position in the mesh, additional pressure is applied to primary trigger 180 to drive the staple through the mesh and into the tissue below, forming and closing the staple as it moves through the tissue. Following staple release, stapler 40 can be moved to additional locations on the mesh patch, via the access port, to fully tack down the patch. One skilled in the art will recognize that based on the above description and methods for mesh fixation, the present invention may similarly be applied for ventral hernia repair.

A further application of the stapler of the present invention is the reinforcement of a staple line in a gastric restructuring procedure. An example of a gastric restructuring procedure in which staple line reinforcement would be advantageous is vertical sleeve gastrectomy. In a vertical sleeve gastrectomy, the stomach is divided and simultaneously stapled shut so that the left side or greater curvature of the stomach is surgically removed. The staple line runs the length of the stomach generally starting approximately 4 cm proximal from the pylorus and running to the Angle of His, resulting in a "new" tubular stomach that is roughly the size and shape of a banana. There is a non-zero leak rate associated with this procedure that left untreated can pose a significant risk to the patient. As such surgeons routinely oversew this staple line infolding the staple line within a tissue fold. This is a time consuming process. The stapler and staples of the present invention can be used to reinforce the staple line of the newly formed stomach by infolding the staple line in a similar manner resulting in a serosa-to-serosa tissue bond.

Figure 51:
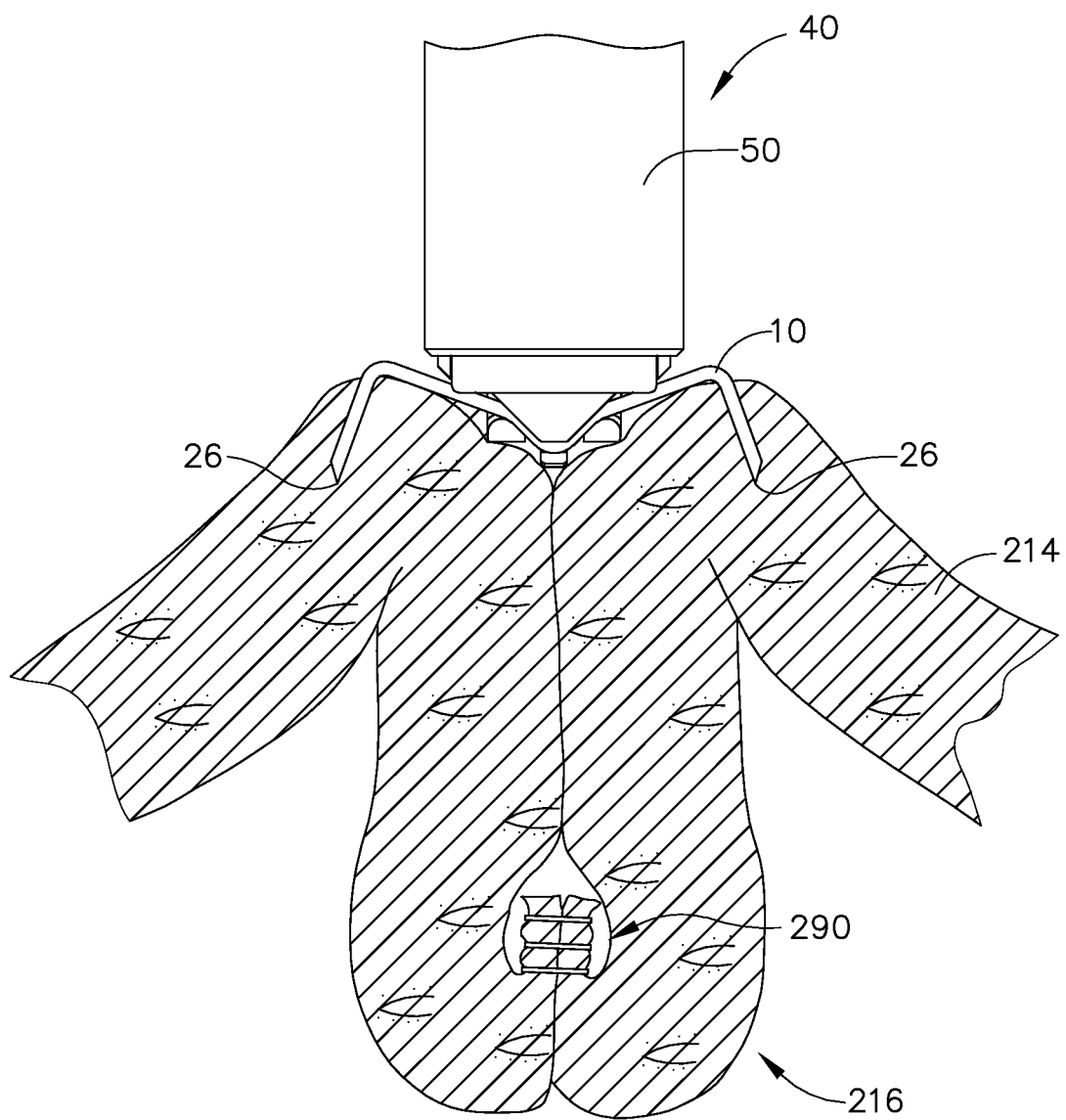
FIG. 51 is a schematic view showing the stapler approximating the cavity wall tissue on opposite sides of the staple line.
Figure 52:
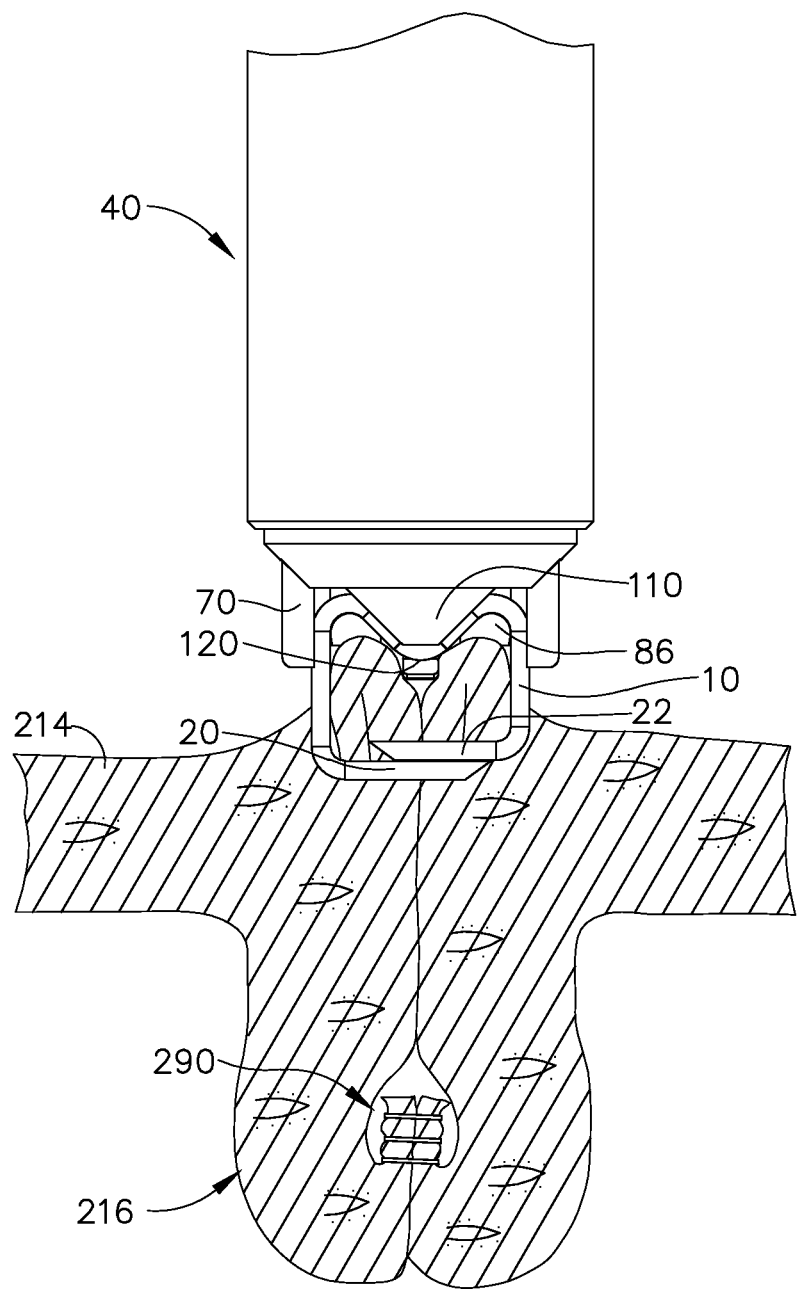
FIG. 52 is a schematic view similar to FIG. 51 showing the stapler forming a staple through the approximated tissue to reinforce the staple line.

As shown in FIG. 51, after the severed stomach portion has been removed, and the remaining stomach stapled closed along a staple line 290, stapler 40 can be used to draw tissue on opposite sides of the staple line together and invaginate the staple line therebetween. With a staple 10 advanced out the open end of stapler 40, the stapler can be manipulated to grab separate sections of the serosal tissue on opposite sides of the staple line 290 and pull the sections together. With the tissue sections pulled together by staple 10, the stapler is fully actuated to form the staple through the tissue, as shown in FIG. 52. After the staple is released from the stapler, the stapler can be moved to a second location along the gastrectomy or other gastric staple line to extend the length of the invaginated tissue. The stapling process can be repeated along the full length of the gastrectomy staple line to reinforce the entire line.

As discussed, the present invention also pertains to the closure of defects on or within the body through secure tissue apposition. A non-limiting list of examples includes closure of gastrotomies, mesenteric defects during Roux-En-Y gastric bypass (RYGB), etc. The present invention also pertains to the reinforcement of fastened tissues through imbrication of the fastened region secured with the low profile stapler. Discussed in detail above is the example of staple line reinforcement during vertical sleeve gastrectomy. A non-limiting list of other opportunities for fastener reinforcement includes RYGB, Billroth I and II, gasgtrogastric anastomosis, gastrojejunostomy anastomosis, and jejunojenostomy anastomosis. By way of a non-limiting list of examples, the present invention also pertains to the temporary or permanent apposition of tissues during procedures such as the management of the roux limb during RYGB, hiatal hernia repair, bladder neck suspension, securement of gastric-gastric wraps during gastric banding, and Nissen fundoplication.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, ethylene oxide (EtO) gas, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam, etc.

Any patent, publication, application or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The foregoing description of preferred embodiments of the invention has been presented for purposes of illustration and description. It is not intended to be exhaustive or to limit the invention to the precise form disclosed. Obvious modifications or variations are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed:

1. A method of deploying a surgical fastener comprising the steps of:
 a. introducing said fastener into a body of a patient while said fastener is in a first shape, said fastener comprising: a base, and two legs extending away from said base, said legs having distal end segments said first shape comprising said distal end segments bending towards and across each other and contacting each other along substantially an entire length of said end segments so that they are adjacent and form said fastener into a first closed-form loop;
 b. moving end segments of said fastener away from said first closed-form loop removing said end segments from contacting each other along substantially said entire length of said end segments and into a second shape wherein said distal end segments are spaced apart from each other along substantially an entire length thereof; and
 c. moving said fastener into a third shape wherein said distal end segments bend towards each other in so that they are adjacent and form said fastener into a second closed-form loop, said second loop having a width greater than a width of said first loop.

2. The method of claim 1 wherein said fastener approximates tissue locations separated by a distance larger than a maximum width between said end segments of said fastener.

3. The method of claim 2 wherein said tissue locations are moved by said end segments of said fastener.

4. The method of claim 2 wherein said tissue locations are moved by at least one additional tissue manipulator.

5. The method of claim 1 wherein said fastener approximates gastrointestinal tissue.

6. The method of claim 5 wherein said fastener creates a plication comprised of gastric tissue thereby reducing a stomach capacity.

7. The method of claim 6 wherein said plication prolongs satiety within a patient.

8. The method of claim 6 wherein said plications decreases the time for a patient to reach satiation.

9. The method of claim 1 wherein said fastener secures an implantable material to a tissue of a patient.

10. The method of claim 1 further comprising the step of introducing a therapeutic agent into a patient via said fastener.

11. The method of claim 1 wherein said fastener is at least partially absorbed.

* * * * *